US007511039B2

(12) United States Patent
Kahn et al.

(10) Patent No.: US 7,511,039 B2
(45) Date of Patent: Mar. 31, 2009

(54) β-SHEET MIMETICS AND USE THEREOF AS INHIBITORS OF BIOLOGICALLY ACTIVE PEPTIDES OR PROTEINS

(75) Inventors: Michael Kahn, Kirkland, WA (US);
Cyprian O. Ogbu, Durham, NC (US);
Masakatsu Eguchi, Seattle, WA (US);
Hwa-Ok Kim, Lexington, MA (US);
Patrick D. Boatman, Jr., San Diego, CA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 11/448,412

(22) Filed: Jun. 7, 2006

(65) Prior Publication Data
US 2006/0276408 A1 Dec. 7, 2006

Related U.S. Application Data

(60) Continuation of application No. 10/745,471, filed on Dec. 22, 2003, now Pat. No. 7,125,872, which is a continuation of application No. 09/561,107, filed on Apr. 28, 2000, now Pat. No. 6,699,869, which is a division of application No. 09/009,665, filed on Jan. 20, 1998, now Pat. No. 6,245,764, which is a continuation of application No. 08/725,073, filed on Oct. 2, 1996, now abandoned, which is a continuation-in-part of application No. 08/624,690, filed on Mar. 25, 1996, now abandoned, which is a continuation-in-part of application No. 08/549,006, filed on Oct. 27, 1995, now abandoned, which is a continuation-in-part of application No. 08/410,518, filed on Mar. 24, 1995, now abandoned.

(51) Int. Cl.
*A01N 43/58* (2006.01)
(52) U.S. Cl. .................. 514/248; 514/19; 514/221; 514/405; 548/356
(58) Field of Classification Search .................. 514/248, 514/19, 221, 405; 548/356
See application file for complete search history.

(56) References Cited

U.S. PATENT DOCUMENTS

| | | | |
|---|---|---|---|
| 4,307,094 | A | 12/1981 | Hassall et al. |
| 4,479,937 | A | 10/1984 | Sato |
| 4,704,359 | A | 11/1987 | Matsuo |
| 5,552,400 | A | 9/1996 | Dolle et al. |
| 5,756,466 | A | 5/1998 | Bemis et al. |
| 6,034,066 | A | 3/2000 | Johnson |

FOREIGN PATENT DOCUMENTS

| | | |
|---|---|---|
| EP | 743319 | 11/1996 |
| WO | WO 93/16103 | 8/1993 |
| WO | WO 93/23403 | 11/1993 |
| WO | WO 94/10193 | 5/1994 |
| WO | WO 95/33751 | 12/1995 |
| WO | WO 95/35308 | 12/1995 |
| WO | WO 96/19483 | 11/1996 |

OTHER PUBLICATIONS

Adam et al., "Determination of the Triplet Lifetimes of 1,3-Cyclopentadiyl Biradicals Derived from the Photodenitrogenation of Azoalkanes with Time-Resolved Photoacoustic Calorimetry," *J. Org. Chem.* 58: 1477-1482, 1993.
Allen et al., "Molecular Modeling Of γ-Lactam Analogues Of β-Lactam Antibacterial Agents: Synthesis And Biological Evaluation Of Selected Penem And Carbapenem Analogues," *Tetrahedron* 45(7): 1905-1928, 1989.
Baldwin et al., "A γ-Lactam Analogue Of Penems Possessing Antibacterial Activity," *Tetrahedron Letters* 27(30): 3461-3464, 1986.
Baldwin et al., "A γ-Lactam Analogue Of The Penems Possessing Antibacterial Activity," *Tetrahedron* 45(14): 4537-4550, 1989.
Baldwin et al., "Synthesis Of A Novel Bicyclic γ-Lactam Analogue Of The 1-Oxapenams," *Tetrahedron* 30(30) : 4019-4020, 1989.
Baldwin et al., "Synthesis Of Bicyclic γ-Lactams Via Oxazolidinones," *Tetrahedron* 42(23): 6551-6554, 1986.
Baldwin et al., "Synthesis of Potential β-Turn Bicyclic Dipeptide Mimetics," *J. Chem. Soc., Chem. Commun.* (11) : 935-936, 1993.
Baldwin et al., "γ-Lactam Analogues Of β-Lactam Antibiotics," *The Journal of Antibiotics* 44(1): 1-24, 1991.
Baldwin et al., "γ-Lactam Analogues of Penicillanic and Carbapenicllanic Acids," *J. Chem. Soc., Chem. Commun.* 5: 250-252, 1983.
Baldwin et al., "γ-Lactam Analogues Of Penicillanic and Carbapenicillanic Acids," *Tetrahedron* 40(21): 4513-4525, 1984.
Baldwin et al., "γ-Lactam Formation from Tripeptides with Isopenicillin N Synthase," *J. Chem. Soc. Commun.* (16): 1128-1130, 1988.
Bastin et al., "Salt Selection and Optimisation Procedures for Pharmaceutical New Chemical Entities", *Organic Process Research & Development*, 2000, 4(5), 427-435.
Bauer et al., "Mehrfach ungesättigte Radikalkationen: Regio- und Stereochemie der oxidativen Dimerisierung von Heptafulvenen," *Chem. Ber.* 117: 809-826, 1984.
Baydar et al., "Acyl Analogues of the Ene Reaction," *J. Chem. Soc. Chem. Comm.* pp. 650-652, 1976.
Belshaw et al., "Synthesis, Structure and Mechanism in Immunophilin Research," *Synlett*: 381-392, 1994.

(Continued)

*Primary Examiner*—David Lukton
(74) *Attorney, Agent, or Firm*—Andrew Gibbs; Jay Z. Zhang; Myriad IP Department

(57) ABSTRACT

There are disclosed β-sheet mimetics and methods relating to the same for imparting or stabilizing the β-sheet structure of a peptide, protein or molecule. In one aspect, β-sheet mimetics are disclosed having utility as protease inhibitors in general and, more specifically, as serine protease inhibitors such as thrombin, elastase and Factor X inhibitors. In one embodiment, the β-sheet mimetic is a thrombin inhibitor.

28 Claims, 4 Drawing Sheets

OTHER PUBLICATIONS

Benvegnu et al., "Diels-Alder Reactions on Linear Polyenes, Selectively Protected as Their Tricarbonyl-Iron Complexes", *Tetrahedron Letters*, 1990, 31(22):3145-3148.

Bernabeu et al., "(2E)-4-Methoxy-2,4-pentadienamides as New Dienes in the Diels-Alder Reaction", *Tetrahedron Letters*, 1996, 37(20):3595-3598.

Boyd et al., "The Chemistry of N-Substituted 3-Amino-1H-2-benzopyran-1-ones and 5-Amino-2,3-dihydrofuran-2-ones. Ene-type Reactions involving Transfer of Acyl Groups. X-Ray Crystal Structure of cis-3,4-Dihydro-4-morpholinocarbonyl-3-p-nitrophenyl-1H-2-benzopyran-1-one," *J. Chem Soc. Perkin Trans.* 1: pp. 1351-1360, 1978.

Boyd et al., "γ-Lactam Analogues Of Carbapenems," *Tetrahedron Letters* 27(30): 3457-3460, 1986.

Boyd et al., "γ-Lactam Analogues Of The Penems," *Tetrahedron Letters* 27(30): 3453-3456, 1986.

Claridge et al., "Synthesis And Analysis Of Leu-Enkephalin Analogues Containing Reverse Turn Peptidomimetics," *Bioorganic & Medicinal Chemistry Letters* 6(4): 485-490, 1996.

Cornille et al., "Anodic Amide Oxidations: Conformationally Restricted Peptide Building Blocks From The Direct Oxidation Of Dipeptides," *Tetrahedron Letters* 35(38): 6989-6992, 1994.

Cornille et al., "Electrochemical Cyclization of Dipeptides toward Novel Bicyclic, Reverse-Turn Peptidomemetics. 1. Synthesis and Conformational Analysis of 7,5-Bicyclic Systems," *J. Am. Chem. Soc.* 117: 909-917, 1995.

Cowley et al., "Regio- and Stereo-selective Intermolecular Interceptions of a Conjugated N-Acylhydrazonium Ion," *Tetrahedron Letters* 35(42): 7853-7856, 1994.

Etzkorn et al., "Cyclic Hexapeptides and Chimeric Peptides as Mimics of Tendamistat," *J. Am. Chem. Soc.* 116: 10412-10425, 1994.

Fersht, "Enzyme Structure and Mechanism", MRC Laboratory of Molecular Biology, WH Freeman & Co., 1977, pp. 18-28 and 302-324.

Fobian et al., "New Routes To Conformationally Restricted Peptide Building Blocks: A Convenient Preparation Of Bicyclic Piperazinone Derivatives," *Bioorganic & Medicinal Chemistry Letters* 6(3): 315-318, 1996.

Gilbert et al., "Nuclear Magnetic Resonance Studies and Conformations of Bicyclic Inhibitors of Angiotensin-converting Enzyme. Part 1. Octahydropyridazo[1,2-a]-pyridizanediones as Models for Alanylproline and Captopril," *J. Chem. Soc. Perkin Trans.* 11(7): 1077-1082, 1985.

Goldschmidt et al., "Activation Of Electron Deficient Cycloheptatrienes By Tricarbonyliron Complexation," *Tetrahedron Letters* 31(46): 6711-6712, 1990.

Grangier et al., "Reactivity of Nucleophilic Uracil Derivatives," *J. Heterocyclic Chem.* 31: 1707-1714, 1994.

Hanessian et al., "Design And Synthesis Of A Prototype Model Antagonist Of Tachykinin NK-2 Receptor," *Bioorganic & Medicinal Chemistry Letters* 4(11): 1397-1400, 1994.

Hashiguchi et al., "Synthesis of γ-Lactam Analogues of Carbapenems with Substituted-thio Groups at the C-3 Position," *J. Chem. Soc. Perkin Trans.* 1(8): 2345-2532, 1988.

Hassall et al., "The Design and Synthesis of New Triazolo, Pyrazolo-, and Pyridazo-pyridazine Derivatives as Inhibitors of Angiotensin Converting Enzyme," *J. Chem. Soc. Perkin Trans.* 1: 155-164, 1984.

Jungeheim et al., "1,3-Dipolar Cycloaddition Reactions of Pyrazolidinium Ylides with Acetylenes. Synthesis of a New Class of Antibacterial Agents," *J. Org. Chem.* 52: 4007-4013, 1987.

Jungheim et al., "1,3-Dipolar Cycloaddition Reactions Of Pyrazolidinium Ylides With Vinyl Sulfones. A Regioselective Synthesis Of Bicyclic Pyrazolidinone Antibacterial Agents," *Tetrahedron* 44(11): 3119-3126, 1988.

Jungheim et al., "Bicyclic Pyrazolidinones, A New Class Of Antibacterial Agent Based On The β-Lactam Model," *Tetrahedron Letters* 28(3): 285-288, 1987.

Krishnan et al., "Structure of thrombin complexed with selective non-electrophilic inhibitors having cyclohexyl moieties at P1", *Acta Crystallographica*, 2000, D56:294-303.

Li et al., "Conformationally Restricted Peptide Mimetics: The Incorporation of 6,5-Bicyclic Lactam Ring Skeletons into Peptides," *J. Org. Chem.* 60: 8155-8170, 1995.

Marchand-Brynaert et al., "New γ-Lactam Homologs Of Penems," *Bioorganic & Medicinal Chemistry Letters* 3(11): 2303-2308, 1993.

Mathew et al., "Asymmetric synthesis and conformational analysis of the two enantiomers of the saturated analog of the potent thrombin inhibitor MOL-376", *Tetrahedron Letters*, 2003, 44:583-586.

Nagai et al., "Bicyclic Turned Dipeptide (BTD) as a β-Turn Mimetic; its Design, Synthesis and Incorporation into Bioactive Peptides," *Tetrahedron* 49(17): 3577-3592, 1993.

Nagai et al., "Synthesis Of A Bicyclic Dipeptide With The Shape of β-Turn Central Part," *Tetrahedron Letters* 26(5): 647-650, 1985.

Nagai et al., "Synthesis of Phenyl-substituted BTD (bicyclic-turned dipeptide) and its incorporation into bioactive peptides," *Peptides* Proceedings of the 11th American Peptide Symposium, J.E. Rivier and G.R. Marshall (eds.), 1990, pp. 653-654.

Oh et al., "Tryptase Inhibition Blocks Airway Inflammation in a Mouse Asthma Model", *The Journal of Immunology*, 2002, 168:1992-2000.

Robl et al., "Dual Metalloprotease Inhibitors. III. Utilization Of Bicyclic And Monocyclic Diazepinone Based Mercaptoacetyls", *Bioorganic & Medicinal Chemistry Letters*, 1994, 35(3):494-502.

Robl et al., "Dual Metalloprotease Inhibitors. 6. Incorporation of Bicyclic and Substituted Monocyclic Azepinones as Dipeptide Surrogates in Angiotensin-Converting Enzyme/Neutral Endopeptidase Inhibitors," *J. Med. Chem.* 39: 494-502, 1996.

Slomcyznska et al., "Electrochemical Cyclization of Dipeptides To Form Novel Bicyclic, Reverse-Turn Peptidomimetics. 2. Synthesis and Conformational Analysis of 6,5-Bicyclic Systems," *J. Org. Chem.* 61(4): 1198-1204, 1996.

Slusarchyk et al., "Dual Metalloprotease Inhibitors.V. Utilization Of Bicylilc Azepinonethiazlidines And Azepinonetetrahydrothiazines In Constrained Peptidomimetics Of Mercaptoacyl Dipeptides," *Bioorganic & Medicinal Chemistry Letters* 5(7): 753-758, 1995.

Storer et al., "Recent insights into cysteine protease specificity: Lessons for drug design", Perspectives in Drug Discovery and Design, 1996, 6:33-46.

Subasinghe et al., "Bicyclic Thiazolidine Lactam Peptidomimetics of the Dopamine Receptor Modulating Peptide Pro-Leu-Gly-NH$_2$," *J. Med. Chem.* 36: 2356-2361, 1993.

Ternansky et al., "[4.3.0] Pyrazolidinones As Potential Antibacterial Agents," *Tetrahedron Letters* 29(50): 6569-6572, 1988.

Ternansky et al., "Structure-Activity Relationship within a Series of Pyrazolidinone Antibacterial Agents. 1. Effect of Nuclear Modification on In Vitro Activity," *J. Med. Chem.* 36(22): 3219-3223, 1993.

Ternansky et al., "Structure-Activity Relationship within a Series of Pyrazolidinone Antibacterial Agents. 2. Effect of Side-Chain Modification on In Vitro Activity and Pharmacokinetic Parameters," *J. Med. Chem.* 36: 3224-3229, 1993.

Ternansky et al., "The Chemistry of Substituted Pyrazolidinones; Applications to the Synthesis of Bicyclic Derivatives," *Tetrahedron* 48(5): 777-796, 1992.

Ternansky et al., "The Synthesis and Biological Evaluation of Pyrazolidinone Antibacterial Agents," in *Recent Advances in the Chemistry of β-Lactam Antibiotics*, Bentley and Southgate (eds.), Royal Society Of Chemistry, Cambridge, England, Jul. 3-6, 1998, Special Publication No. 70, Chapter 9, "The Synthesis and Biological Evaluation of Pyrazolidinone Antibacterial Agents," pp. 139-156.

Thomas et al., "Nuclear Magnetic Resonance Studies and Conformational Analysis of Bicyclic Inhibitors of Angiotensin-converting Enzyme. Part 2. The Octahydro-6H-pyridazo[1,2-a][1,2]diazepines," *J. Chem. Soc. Perkin Trans.* 11(5): 747-755, 1986.

Thompson et al., Section VI. Topics in Drug Design and Discovery, Chapter 24. Pharmacokinetics and Design of Aspartyl Protease Inhibitors, Annual Reports in Medicinal Chemistry, 2001, 36:247-256.

Wyvratt et al., "Bicyclic Inhibitors Of Angiotensin-Converting Enzyme," in *Peptides Structure and Function*, Proceedings of the Eighth American Peptide Symposium, Hruby and Rich (eds.), Pierce Chemical Company, Rockford, Illinois, 1983, pp. 551-554.

Wyvratt et al., "Recent Developments in the Design of Angiotensin-Converting Enzyme Inhibitors," *Medicinal Research Reviews* 5(4): 483-531, 1985.

Attwood et al., "The Design and Synthesis of the Angiotensin Converting Enzyme Inhibitor Cilazapril and Related Bicyclic Compounds", *J. Chem. Soc. Perkin Trans* 1, 1986, 1011-1019.

Baldwin et al., "Synthesis of a Bicyclic γ-Lactam Dipeptide Analogue", *Heterocycles*, 1992, 34(5):903-906.

Colombo et al., "Conformationally Constarined Dipeptides: Synthesis of 7,5- and 6,5-Fused Bicyclic Lactams by Stereoselective Radical Cyclizations", *Tetrahedron Letters*, 1995, 36(4):625-628.

Colombo et al., "Synthesis of 7,5-Fused Bicyclic Lactams by Stereoselective Radical Cyclization[1]", *Tetrahedron Letters*, 1994, 35(23):4031-4034.

Du Vigneaud et al., "The γ-Lactam of Benzylhomopenicilloic Acid and Related Compounds", in *The Chemistry of Penicillin*, Clarke et al. (eds.), Princeton University Press, Princeton, New Jersey, USA, 1949, pp. 1004-1017.

Jungheim et al., "Bicyclic Pyrazolidinones, Steric and Electronic Effects on Antibacterial Activity", *Tetrahedron Letters*, 1987, 28(3):289-292.

Lombart et al., "A Claisen condensation approach to prepare azabicycloalkane amino acid β-turn mimetics", *Peptides 1994, Proceeding of the Twenty-Third European Peptide Symposium*, Edited by H.L.S. Maia, Sep. 4-10, 1994, 696-697.

Lombart et al., "Synthesis of Enantiopure α,w-Diamino Dicarboxylates and Azabicycloalkane Amino Acids by Claisen Condensation of α-[N-(Phenylfluorenyl)amino] Dicarboxylates", *Journal of Organic Chemistry*, 1994, 59(21):6147-6149.

Mueller et al., "Synthesis of 6,5-Fused bicyclic Lactams as Potential Dipeptide β-Turn Mimetics", *Tetrahedron Letters*, 1994, 35(24):4091-4092.

Robl, "Peptidomimetic Synthesis: Utilization of N-Acyliminium Ion Cyclization Chemistry in the Generation of 7,6- and 7,5-Fused Bicyclic Lactams", Tetrahedron Letters, 1994, 35(3):393-396.

Seguchi et al., "Ready Alcoholysis of the Cycloadducts (Urazole) of 4-Phenyl-1,2,4-triazole-3,5-dione by Solvent-assisted Backbone Participation", *J. Chem. Soc. Perkin. Trans.* 1, 1991:2883-2884.

SEQUENCE LISTING

<160> NUMBER OF SEQ ID NOS: 12

<210> SEQ ID NO 1
<211> LENGTH: 4
<212> TYPE: PRT
<213> ORGANISM: Unknown
<220> FEATURE:
<223> OTHER INFORMATION: Serine Kinase

<400> SEQUENCE: 1

-continued

```
Ile Glu Gly Arg
1

<210> SEQ ID NO 2
<211> LENGTH: 7
<212> TYPE: PRT
<213> ORGANISM: Unknown
<220> FEATURE:
<223> OTHER INFORMATION: Tyrosine Kinase

<400> SEQUENCE: 2

Leu Arg Arg Ala Ser Leu Gly
1               5

<210> SEQ ID NO 3
<211> LENGTH: 4
<212> TYPE: PRT
<213> ORGANISM: Unknown
<220> FEATURE:
<223> OTHER INFORMATION: CAAX INHIBITOR

<400> SEQUENCE: 3

Leu Pro Tyr Ala
1

<210> SEQ ID NO 4
<211> LENGTH: 4
<212> TYPE: PRT
<213> ORGANISM: Unknown
<220> FEATURE:
<223> OTHER INFORMATION: CAAX INHIBITOR

<400> SEQUENCE: 4

Cys Val Ile Met
1

<210> SEQ ID NO 5
<211> LENGTH: 4
<212> TYPE: PRT
<213> ORGANISM: Unknown
<220> FEATURE:
<223> OTHER INFORMATION: CAAX Inhibitor

<400> SEQUENCE: 5

Cys Val Phe Met
1

<210> SEQ ID NO 6
<211> LENGTH: 10
<212> TYPE: PRT
<213> ORGANISM: Unknown
<220> FEATURE:
<223> OTHER INFORMATION: X = SH2 Peptide analogue - IRS 1 analog
<220> FEATURE:
<221> NAME/KEY: PHOSPHORYLATION
<222> LOCATION: (1)..(1)
<220> FEATURE:
<221> NAME/KEY: MISC_FEATURE
<222> LOCATION: (2)..(2)
<223> OTHER INFORMATION: Xaa = norleucine
<220> FEATURE:
<221> NAME/KEY: MISC_FEATURE
<222> LOCATION: (4)..(4)
<223> OTHER INFORMATION: Xaa = norleucine
<220> FEATURE:
<221> NAME/KEY: PHOSPHORYLATION
<222> LOCATION: (6)..(6)
<220> FEATURE:
<221> NAME/KEY: MISC_FEATURE
```

```
<222> LOCATION: (7)..(7)
<223> OTHER INFORMATION: Xaa = norleucine
<220> FEATURE:
<221> NAME/KEY: MISC_FEATURE
<222> LOCATION: (9)..(9)
<223> OTHER INFORMATION: Xaa = norleucine

<400> SEQUENCE: 6

Tyr Xaa Pro Xaa Ser Tyr Xaa Pro Xaa Ser
1               5                   10

<210> SEQ ID NO 7
<211> LENGTH: 11
<212> TYPE: PRT
<213> ORGANISM: Unknown
<220> FEATURE:
<223> OTHER INFORMATION: SH2 Peptide Analog - Src SH2 binding motif
<220> FEATURE:
<221> NAME/KEY: PHOSPHORYLATION
<222> LOCATION: (3)..(3)

<400> SEQUENCE: 7

Glu Pro Gln Tyr Glu Glu Ile Pro Ile Tyr Leu
1               5                   10

<210> SEQ ID NO 8
<211> LENGTH: 9
<212> TYPE: PRT
<213> ORGANISM: Unknown
<220> FEATURE:
<223> OTHER INFORMATION: Class MCH I Peptides - Influenza Nulcoprotein

<400> SEQUENCE: 8

Thr Tyr Gln Arg Thr Arg Ala Leu Val
1               5

<210> SEQ ID NO 9
<211> LENGTH: 8
<212> TYPE: PRT
<213> ORGANISM: Unknown
<220> FEATURE:
<223> OTHER INFORMATION: Class MCH I Peptides - VSV

<400> SEQUENCE: 9

Arg Gly Tyr Val Tyr Gln Gly Leu
1               5

<210> SEQ ID NO 10
<211> LENGTH: 15
<212> TYPE: PRT
<213> ORGANISM: Unknown
<220> FEATURE:
<223> OTHER INFORMATION: Beta Sheet Modified Peptide

<400> SEQUENCE: 10

Thr Thr Tyr Ala Asp Phe Ile Ala Ser Gly Arg Thr Gly Arg Arg
1               5                   10                  15

<210> SEQ ID NO 11
<211> LENGTH: 11
<212> TYPE: PRT
<213> ORGANISM: Unknown
<220> FEATURE:
<223> OTHER INFORMATION: Beta Sheet Modified Peptide

<400> SEQUENCE: 11

Tyr Val Lys Gln Asn Thr Leu Lys Leu Ala Thr
1               5                   10
```

```
<210> SEQ ID NO 12
<211> LENGTH: 7
<212> TYPE: PRT
<213> ORGANISM: Unknown
<220> FEATURE:
<223> OTHER INFORMATION: Beta Sheet Modified Peptide

<400> SEQUENCE: 12

Tyr Asp Glu Glu Ala Arg Arg
1               5
```

β-SHEET MIMETICS AND USE THEREOF AS INHIBITORS OF BIOLOGICALLY ACTIVE PEPTIDES OR PROTEINS

CROSS-REFERENCE TO PRIOR APPLICATIONS

This application is a continuation of U.S. patent application Ser. No. 10/745,471 filed Dec. 22, 2003, now U.S. Pat. No. 7,125,872; which is a continuation of U.S. patent application Ser. No. 09/561,107 filed Apr. 28, 2000, now U.S. Pat. No. 6,699,869; which is a divisional of U.S. patent application Ser. No. 09/009,665 filed Jan. 20, 1998, now U.S. Pat. No. 6,245,764; which is a continuation of U.S. patent application Ser. No. 08/725,073 filed Oct. 2, 1996, now abandoned; which is a continuation-in-part of U.S. patent application Ser. No. 08/624,690, filed Mar. 25, 1996, now abandoned; which is a continuation-in-part of U.S. patent application Ser. No. 08/549,006, filed Oct. 27, 1995, now abandoned; which is a continuation-in-part of U.S. patent application Ser. No. 08/410,518, filed Mar. 24, 1995, now abandoned.

TECHNICAL FIELD

This invention relates generally to β-sheet mimetics and, more specifically, to β-sheet mimetics which inhibit biologically active peptides or proteins.

BACKGROUND OF THE INVENTION

The β-sheet conformation (also referred to as a β-strand conformation) is a secondary structure present in many polypeptides. The β-sheet conformation is nearly fully extended, with axial distances between adjacent amino acids of approximately 3.5 Å. The β-sheet is stabilized by hydrogen bonds between NH and CO groups in different polypeptide strands. Additionally, the dipoles of the peptide bonds alternate along the strands which imparts intrinsic stability to the β-sheet. The adjacent strands in the β-sheet can run in the same direction (i.e., a parallel β-sheet) or in opposite directions (i.e., an antiparallel β-sheet). Although the two forms differ slightly in dihedral angles, both are sterically favorable. The extended conformation of the β-sheet conformation results in the amino acid side chains protruding on alternating faces of the β-sheet.

The importance of β-sheets in peptides and proteins is well established (e.g., Richardson, *Nature* 268:495-499, 1977; Halverson et al., *J. Am. Chem Soc.* 113:6701-6704, 1991; Zhang, *J. Biol. Chem.* 266:15591-15596, 1991; Madden et al., *Nature* 353:321-325, 1991). The β-sheet is important in a number of biological protein-protein recognition events, including interactions between proteases and their substrates, protein kinases and their substrates or inhibitors, the binding of SH2 domain containing proteins to their cognate phosphotyrosine containing protein targets, farnesyl transferase to its protein substrates, and MHC I and II and their antigenic peptides, and has been implicated in many disease states.

Inhibitors that mimic the β-sheet structure of biologically active proteins or peptides would have utility in the treatment of a wide variety of conditions. For example, Ras, the protein product of the ras oncogene, is a membrane bound protein involved in signal transduction regulating cell division and growth. Mutations in the ras gene are among the most common genetic abnormalities associated with human cancers (Barbacid, M. "ras genes," 56:779-827, 1987). These mutations result in a growth signal which is always "on," leading to a cancerous cell. In order to localize to the cell membrane, Ras requires prenylation of the cysteine within its C-terminal CaaX sequence by farnesyl transferase (FTase). (In the sequence CaaX "a" is defined as an amino acid with a hydrophobic side chain and "X" is another amino acid.) This post-translational modification is crucial to its activity. Peptidyl inhibitors of FTase with the sequence CaaX have been shown to block or slow the growth of tumors in cell culture and in whole animals (Kohl et al., "Selective inhibition of ras-dependent transformation by a farnesyltransferase inhibitor," *Science* 260:1934-1937, 1993; Buss, J. E. & Marsters, Jr., J. C. "Farnesyl transferase inhibitors: the successes and surprises of a new class of potential cancer chemotherapeutics," *Chemistry and Biology* 2:787-791, 1995).

SH2 domains, originally identified in the src subfamily of PTKs, are noncatalytic sequences and consist of about 100 amino acids conserved among a variety of signal transducing proteins (Cohen et al., *Cell* 80:237-248, 1995). SH2 domains function as phosphotyrosine-binding modules and mediate critical protein-protein associations (Pawson, *Nature* 573-580, 1995). In particular, the role of SH2 domains has been clearly defined as critical signal transducers for receptor tyrosine kinases (RTKs such as EGF-R, PDGF, insulin receptor, etc.). Phosphotyrosine-containing sites on autophosphorylated RTKs serve as binding sites for SH2-proteins and thereby mediate the activation of biochemical signaling pathways (Carpenter, G., *FAESEB J.* 6:3283-3289, 1992; Sierke, S. and Koland, J., *Biochem.* 32:10102-10108, 1993). The SH2 domains are responsible for coupling the activated growth-factor receptors to cellular responses which include alterations in gene expression, cell proliferation, cytoskeletal architecture and metabolism.

At least 20 cytosolic proteins have been identified that contain SH2 domains and function in intracellular signaling. The distribution of SH2 domains is not restricted to a particular protein family, but is found in several classes of proteins, protein kinases, lipid kinases, protein phosphatases, phospholipases, Ras-controlling proteins and some transcription factors. Many of the SH2-containing proteins have known enzymatic activities while others (Grb2 and Crk) function as "linkers" and "adapters" between cell surface receptors and downstream effector molecules (Marengere, L., et al., *Nature* 369:502-505, 1994). Examples of proteins containing SH2 domains with enzymatic activities that are activated in signal transduction include, but are not limited to, the src subfamily of protein tyrosine kinases (src (pp60$^{c\text{-}src}$), abl, lck, fyn, fgr and others), phospholipase-C-γ (PLC-γ), phosphatidylinositol 3-kinase (PI-3-kinase), p21-ras GTPase activating protein (GAP) and SH2 containing protein tyrosine phosphatases (SH-PTPase) (Songyang et al., *Cell* 72:767-778, 1993). Intracellular tyrosines are phosphorylated when surface receptors are engaged by diverse ligands for growth factor receptors, cytokine receptors, insulin receptor, and antigen-mediated signaling through T- or B-cell receptors. The phosphorylation of proteins at tyrosine residues is critical in the cellular signal transduction, neoplastic transformation and control of the cell cycle. Due to the central role these various SH2-proteins occupy in transmitting signals from activated cell surface receptors into a cascade of additional molecular interactions that ultimately define cellular responses, inhibitors which block specific SH2-protein binding are desirable as agents for a variety of potential therapeutic applications.

Disease areas in which tyrosine phosphorylation and inhibition of SH2 binding represent targets for drug development include the following:

Cancer: SH2 domains which mediate signaling are clearly significant elements in the regulation of oncogene and protooncogene tyrosine kinase activity and cellular proliferation (Carpenter, *Fed. Am. Soc. Exp. Biol. J.* 6:3283-3289, 1992). The SH2 domains define an important set of substrates through which activated RTKs mediate signaling and through which nonreceptor tyrosine kinases associate with RTKs and are thus targets for anticancer drug development. The ability to block interaction of the RTK with the SH2-containing substrate using a mimetic inhibitor provides a means to abrogate signaling and thereby eliminate oncogenic activity. The biological significance is also illustrated by the v-crk oncogene, a protein composed almost entirely of SH domains, which is able to bring about cellular transformation by interacting with phosphotyrosine containing proteins. As above, the ability of inhibitors to block v-crk binding via its SH2 domain to other proteins would be expected to be effective as an anticancer agent.

Immune Regulation: Regulation of many immune responses is mediated through receptors that transmit signals through tyrosine kinases containing SH2 domains. T-cell activation via the antigen specific T-cell receptor (TCR) initiates a signal transduction cascade leading to lymphokine secretion and cell proliferation. One of the earliest biochemical responses following TCR activation is an increase in tyrosine kinase activity. In particular, T-cell activation and proliferation is controlled through T-cell receptor mediated activation of $p56^{lck}$ and $p59^{fyn}$ tyrosine kinases, as well as ZAP-70 and Syk (Weiss and Litman, *Cell* 76:263-274, 1994) which contain SH2 domains. Additional evidence indicates that several src-family kinases (lck, blk, fyn) participate in signal transduction pathways leading from B-cell antigen receptors and hence may serve to integrate stimuli received from several independent receptor structures. Thus, inhibitors that block interactions of these SH2 domain kinases with their cognate receptors could serve as immunosuppressive agents with utility in autoimmune diseases, transplant rejection or as anti-inflammatory agents as well as anticancer drugs in cases of lymphocytic leukemias.

Additionally, non-transmembrane PTPase containing SH2 domains are known and nomenclature refers to them as SH-PTP1 and SH-PTP2 (Neel, *Cell Biology* 4:419-432, 1993) SH-PTP1 is identical to PTP1C, HCP or SHP and SH-PTP2 is also known as PTP1D or PTP2C. SH-PTP1 is expressed at high levels in hematopoietic cells of all lineages and all stages of differentiation. Since the SH-PTP1 gene was identified as responsible for the motheaten (me) mouse phenotype, this provides a basis for predicting the effects of inhibitors that would block its interaction with its cellular substates. Thus, inhibition of SH-PTP1 function would be expected to result in impaired T-cell responses to mitogenic stimulation, decreased NK cell function, and depletion of B-cell precursors with potential therapeutic applications as described above.

Diabetes: In Type 2 (non-insulin dependent) diabetes, tyrosine phosphatases (SH-PTP2) counter-balance the effect of activated insulin-receptor kinases and may represent important drug targets. In vitro experiments show that injection of PTPase blocks insulin stimulated-phosphorylation of tyrosyl residues on endogenous proteins. Thus, inhibitors could serve to modulate insulin action in diabetes.

Neural Regeneration: Glial growth factors are ligands that are specific activators of erb-B2 receptor tyrosine kinase ($p185^{erbB2}$) to promote tyrosine phosphorylation and mitogenic responses of Schwann cells. Consequently, regulation of tyrosine phosphorylation by altering activity in Schwann cells following nerve injury could be an important therapeutic strategy. Inhibitors of erb-B2 signaling activity could have a significant role in treatment of tumors of glial cell origin.

Another class of β-sheet mimetics are inhibitors of protein kinases, which include the protein tyrosine kinases and serine/threonine kinases.

A wide variety of cellular substrates for polypeptide growth factor receptors that possess intrinsic tyrosine kinase activity have now been characterized. Although there is a tremendous diversity among the numerous members of the receptors tyrosine-kinases (RTK) family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain. The increased activity results in tyrosine-specific phosphorylation of a number of intracellular substrates which contain a common sequence motif. Consequently, this causes activation of numerous downstream signaling molecules and a cascade of intracellular pathways that regulate phospholipid metabolism, arachidonate metabolism, protein phosphorylation (involving other protein kinases), calcium mobilization and transcriptional regulation. The growth-factor-dependent tyrosine kinase activity of the RTK cytoplasmic domain is the primary mechanism for generation of intracellular signals that initiate multiple cellular responses. Thus, inhibitors which would serve as alternate substrates or inhibitors of tyrosine kinase activity have the potential to block this signaling.

Many of the RTK subfamilies are recognizable on the basis of architectural similarities in the catalytic domain as well as distinctive motifs in the extracellular ligand binding regions. Based upon these structural considerations, a nomenclature defining several subfamilies of RTKs, each containing several members, has been developed (Hanks, *Curr. Opin. Struc. Biol.* 1:369-383, 1991; Ullrich, A., and Schlessinger, *J. Cell* 61:203-212, 1990). Examples of receptor subfamilies referred to on the basis of their prototypic members include: EGF-receptor, insulin receptor, platelet-derived growth factor (PDGF-receptor), fibroblast growth factor receptors (FGFRs), TRK receptor and EPH/ECK receptors. Members in each of these subfamilies represent molecular targets for the development of mimetic inhibitors that would block tyrosine kinase activity and prevent intracellular signal transduction. Several therapeutic areas in which these targets have value are identified below.

Cancer: In addition to mediating normal cellular growth, members of the EGFR family of RTKs are frequently overexpressed in a variety of aggressive epithelial carcinomas and this is thought to directly contribute to malignant tumor development. A number of studies have shown that the EGFR is frequently amplified in certain types of tumors, including glioblastomas, squamous carcinomas, and brain tumors (Wong et al., *Proc. Natl. Acad Sci USA* 84:6899-6903, 1987). Additionally, HER2/$p185^{erbB2}$ (alternatively referred to as "neu" in the rat), HER3/$p160^{erbB3}$, HER4/$p180^{erbB4}$ (Plowman, G. et al., *Proc. Natl. Acad. Sci. USA* 90:1746-1750 (1993) are three RTKs which have extensive amino acid sequence homology to the EGFR. HER2/$p185^{erbB2}$ is frequently amplified and overexpressed in human breast tumors and ovarian carcinomas (Wong et al., *Proc. Natl. Acad. Sci. USA* 84:6899-6903, 1987), and this amplification is correlated with poor patient prognosis. Simultaneous overexpression of $p185^{neu}$ and the EGFR synergistically transforms rodent fibroblasts and this condition is often observed in human cancers. Finally, HER3 expression is amplified in a variety of human adenocarcinomas. Several inhibitors are known which demonstrate inhibitory activity in vitro against the EGFR and block EGF-dependent cell proliferation which indicates therapeutic potential of compounds with this activity. In addition, in human chronic myelogenous leukemia, enhanced tyrosine kinase activity underlies the disease as a consequence of activation of the cellular c-abl protooncogene. Inhibitors would function as anticancer agents.

Angiogenesis: Currently, there are at least seven FGFR members which mediate a diverse array of biological responses, including the capacity to induce angiogenesis. In addition, a group of RTKs with seven lgLs has been proposed to represent a separate subfamily. Its known members, FLT1, FLK1 and FLT4 show a similarity of structure and expression. These receptors mediate the actions of Vascular Endothelial Growth Factor (VEGF). Several lines of evidence indicate that this subfamily of growth factor receptors play an important role in the formation of blood vessels. Since blood vessel formation is a process reactivated by tumors in order to supply oxygen to these cells, β-strand mimetics that inhibit these growth factors' kinase activities could serve to suppress tumor growth through inhibition of angiogenesis.

Restenosis: The PDGF receptor is of great interest as a target for inhibition in the cardiovascular field since it is believed to play a significant role in restenosis after coronary balloon angioplasties and also in atherosclerosis. The release of PDGF by platelets at damaged surfaces of blood vessels results in stimulation of PDGF receptors on vascular smooth muscle cells, and eventual neointimal thickening. A mimetic inhibitor of kinase activity would prevent proliferation and lead to greater successful outcomes from this surgical procedure.

Many components of signal transduction pathways involve phosphorylation of serine/threonine (ser/thr) residues of protein substrates. Some of these substrates are themselves protein kinases whose activity is modulated by phosphorylation. Two prominent ser/thr-specific protein kinases play a central role in signal transduction: cyclic AMP-dependent protein kinase A (PKA) and the protein kinase C (PKC family). Numerous other serine/threonine specific kinases, including the family of mitogen-activated protein (MAP) kinases serve as important signal transduction proteins which are activated in either growth-factor receptor or cytokine receptor signaling. Other protein ser/thr kinases important for intracellular signaling are Calcium-dependent protein kinase (CaM-kinase II) and the c-raf-protooncogene.

PKC plays a crucial role in cell-surface signal transduction for controlling a variety of physiological processes (Nishizuka, *Nature* 334:661-665, 1988) and represents a large family of isoenzymes which differ in their structure and expression in different tissues, as well as their substrate specificity (Hug and Sarre, *Biochem J.* 291:329-343, 1993). Molecular cloning has demonstrated at least 8 isoenzymes. Due to this diversity and differential expression, activation of individual isoenzymes produces differing cell-specific responses: stimulation of growth, inhibition of differentiation, or induction of differentiation. Due to its ability to stimulate cellular proliferation, it represents a target for anticancer drug development (Powis, *Trends in Pharm. Sci.* 12:188-194, 1991). Overexpression of PKC isoenzymes in mammalian cells is correlated with enhanced expression of early protooncogenes such as c-jun, c-fos, c-myc and one overexpressing cell line gives rise to tumors in nude mice.

Therapeutic applications within the area of immune regulation are evident since activation of T-cells by antigens involves activation of PKC. Activated PKC subsequently activates a branch of the signal cascade that is necessary for transcriptional activation of NF-κB, production of IL-2, and ultimately, T-cell proliferation. Inhibitors that block signaling through this branch pathway have been shown to prevent T-cell activation. Thus, mimetics that would function as inhibitors of PKC in T-cells would block signaling and serve as possible immunosuppressants useful in transplant rejection or as anticancer agents for lymphocytic leukemias. Activators of PKC cause edema and inflammation in mouse skin (Hennings et al., *Carcinogenesis* 8:1342-1346, 1987) and thus inhibitors are also expected to serve as potent anti-inflammatory compounds. Such anti-inflammatory activates would find use in asthma, arthritis and other inflammatory mediated processes. In addition, staurosporine and its analogs, UCN01 and CGP4125, which have been characterized as potent PKC inhibitors in vitro, have anti-tumor activity in animal models (Powis, *Trends in Pharm. Sci.* 12:188-194, 1991), and related compounds are being considered for clinical trials.

With regard to protease inhibition, Cathepsin B is a lysosomal cysteine protease normally involved in proenzyme processing and protein turnover. Elevated levels of activity have been implicated in tumor metastasis (Sloane, B. F. et al., "Cathepsin B and its endogenous inhibitors: the role in tumor malignancy," *Cancer Metastasis Rev.* 9:333-352, 1990), rheumatoid arthritis (Werb, Z. "Proteinases and matrix degradation," in Textbook of Rheumatology, Keller, W. N.; Harris, W. D.; Ruddy, S.; Sledge, C. S., Eds., 1989, W.B. Saunder Co., Philadelphia, Pa., pp. 300-321), and muscular dystrophy (Katunuma N. & Kominami E., "Abnormal expression of lysosomal cysteine proteinases in muscle wasting diseases," *Rev. Physiol. Biochem. Pharmacol.* 108:1-20, 1987).

Calpains are cytosolic or membrane bound Ca++-activated proteases which are responsible for degradation of cytoskeletal proteins in response to changing calcium levels within the cell. They contribute to tissue degradation in arthritis and muscular dystrophy (see Wang K. K. & Yuen P. W., "Calpain inhibition: an overview of its therapeutic potential," *Trends Pharmacol. Sci.* 15:412-419, 1994).

Interleukin Converting Enzyme (ICE) cleaves pro-IL-1 beta to IL-1 beta, a key mediator of inflammation, and therefore inhibitors of ICE may prove useful in the treatment of arthritis (see, e.g., Miller B. E. et al., "Inhibition of mature IL-1 beta production in murine macrophages and a murine model of inflammation by WIN 67694, an inhibitor of IL-1 beta converting enzyme," *J. Immunol.* 154:1331-1338, 1995). ICE or ICE-like proteases may also function in apoptosis (programmed cell death) and therefore play roles in cancer, AIDS, Alzheimer's disease, and other diseases in which disregulated apoptosis is involved (see Barr, P. J.; Tomei, L. D., "Apoptosis and its Role in Human Disease," *Biotechnol.* 12:487-493, 1994).

HIV protease plays a key role in the life cycle of HIV, the AIDS virus. In the final steps of viral maturation it cleaves polyprotein precursors to the functional enzymes and structural proteins of the virion core. HIV protease inhibitors were quickly identified as an excellent therapeutic target for AIDS (see Huff, J. R., "HIV protease: a novel chemotherapeutic target for AIDS," *J. Med. Chem.* 34:2305-2314) and have already proven useful in its treatment as evidenced by the recent FDA approval of ritonavir, Crixivan, and saquinavir.

Angiotensin converting enzyme (ACE) is part of the renin-angiotensin system which plays a central role in the regulation of blood pressure. ACE cleaves angiotensin I to the octapeptide angiotensin II, a potent pressor agent due to its vasoconstrictor activity. Inhibition of ACE has proved therapeutically useful in the treatment of hypertension (Williams, G. H., "Converting-enzyme inhibitors in the treatment of hypertension," *N. Engl. J. Med.* 319:1517-1525, 1989.

Collegenases cleave collagen, the major constituent of the extracellular matrix (e.g., connective tissue, skin, blood vessels). Elevated collagenase activity contributes to arthritis (Krane S. M. et al., "Mechanisms of matrix degradation in rheumatoid arthritis," *Ann. N.Y. Acad. Sci.* 580:340-354, 1990.), tumor metastasis (Flug M. & Kopf-Maier P., "The basement membrane and its involvement in carcinoma cell invasion," *Acta Anat. Basel* 152:69-84, 1995), and other diseases involving the degradation of connective tissue.

Trypsin-like serine proteases form a large and highly selective family of enzymes involved in hemostasis/coagulation (Davie, E. W. and K. Fujikawa, "Basic mechanisms in blood coagulation," Ann. Rev. 799-829, 1975) and complement activation (Muller-Eberhard, H. J., "Complement," *Ann. Rev. Biochem.* 44:697-724, 1975). Sequencing of these proteases has shown the presence of a homologous trypsin-like core with amino acid insertions that modify specificity and which are generally responsible for interactions with other macromolecular components (Magnusson et al., "Proteolysis and Physiological Regulation," *Miami Winter Symposia* 11:203-239, 1976).

Thrombin, a trypsin-like serine protease, acts to provide limited proteolysis, both in the generation of fibrin from fibrinogen and the activation of the platelet receptor, and thus plays a critical role in thrombosis and hemostasis (Mann, K. G., "The assembly of blood clotting complexes on membranes," *Trends Biochem. Sci.* 12:229-233, 1987). Thrombin exhibits remarkable specificity in the removal of fibrinopeptides A and B of fibrinogen through the selective cleavage of only two Arg-Gly bonds of the one-hundred and eighty-one Arg- or Lys-Xaa sequences in fibrinogen (Blomback, H., *Blood Clotting Enzymology*, Seeger, W. H. (ed.), Academic Press, New York, 1967, pp. 143-215).

Many significant disease states are related to abnormal hemostasis, including acute coronary syndromes. Aspirin and heparin are widely used in the treatment of patients with acute coronary syndromes. However, these agents have several intrinsic limitations. For example, thrombosis complicating the rupture of atherosclerotic plaque tends to be a thrombin-mediated, platelet-dependent process that is relatively resistant to inhibition by aspirin and heparin (Fuster et al., "The pathogenesis of coronary artery disease and the acute coronary syndromes," *N. Engl. J. Med.* 326:242-50, 1992).

Thrombin inhibitors prevent thrombus formation at sites of vascular injury in vivo. Furthermore, since thrombin is also a potent growth factor which initiates smooth muscle cell proliferation at sites of mechanical injury in the coronary artery, inhibitors block this proliferative smooth muscle cell response and reduce restenosis. Thrombin inhibitors would also reduce the inflammatory response in vascular wall cells (Harker et al., *Am. J. Cardiol.* 75:12B-16B, 1995).

In view of the important biological role played by the β-sheet, there is a need in the art for compounds which can stabilize the intrinsic β-sheet structure of a naturally occurring or synthetic peptide, protein or molecule. There is also a need in the art for making stable β-sheet structures, as well as the use of such stabilized structures to effect or modify biological recognition events which involve β-sheet structures. The present invention fulfills these needs and provides further related advantages.

SUMMARY OF THE INVENTION

Briefly stated, the present invention is directed to achieving therapeutic affects in a warm-blooded animal through one or more of protease inhibition, kinase inhibition, CAAX inhibition, interference with peptides binding to SH2 domains and inhibition of MCH-I and/or MHC II presentation of peptides to T cell receptors in the warm-blooded animal. The therapeutic effects result from administering to the warm-blooded animal a therapeutically effective amount of a β-sheet mimetic including a bicyclic ring system, wherein the β-sheet mimetic has the general structure (I):

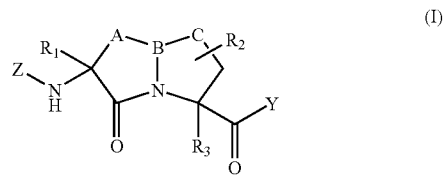

(I)

and pharmaceutically acceptable salts thereof, wherein $R_1$, $R_2$ and $R_3$ are independently selected from amino acid side chain moieties and derivatives thereof; A is selected from —C(=O)—, —(CH$_2$)$_{1-4}$—, —C(=O)(CH$_2$)$_{1-3}$—, —(CH$_2$)$_{1-2}$O— and —(CH$_2$)$_{1-2}$S—; B is selected from N and CH; C is selected from —C(=O)—, —(CH$_2$)$_{1-3}$—, —O—, —S—, —O—(CH$_2$)$_{1-2}$— and —S(CH$_2$)$_{1-2}$—; Y and Z represent the remainder of the molecule; and any two adjacent CH groups of the bicyclic ring may form a double bond.

In one embodiment of structure (I) above β-sheet mimetics are disclosed having the following structure (II):

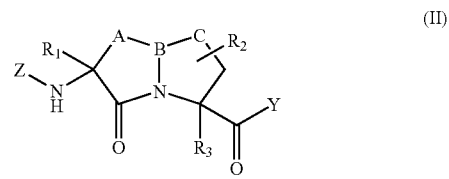

(II)

wherein $R_1$, $R_2$ and $R_3$ are independently selected from amino acid side chain moieties and derivatives thereof; A is selected from —C(=O)—, —(CH$_2$)$_{1-4}$— and —C(=O)(CH$_2$)$_{1-3}$—; B is selected from N and CH; C is selected from —C(=O)— and —(CH$_2$)$_{1-3}$—; Y and Z represent the remainder of the molecule and the bicyclic ring system is saturated (i.e., contains no double bonds between adjacent CH groups of the bicyclic ring system).

In an embodiment of structure (II) where B is CH and $R_3$ is hydrogen, β-sheet mimetics are disclosed having the following structures (III), (IV) and (V):

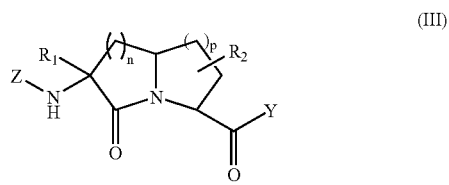

(III)

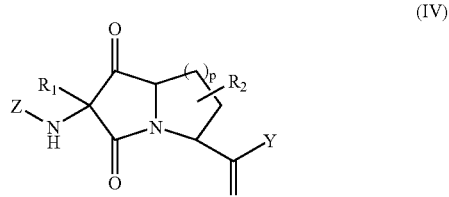

(IV)

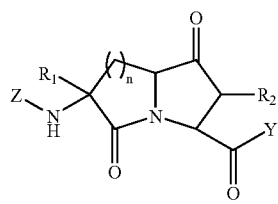
(V)

wherein $R_1$ and $R_2$ are independently selected from amino acid side chain moieties and derivatives thereof; n is an integer from 1 to 4; p is an integer from 1 to 3; and Y and Z represent the remainder of the molecule.

In an embodiment of structure (II) where B is N and $R_3$ is hydrogen, β-sheet mimetics are disclosed having the following structures (VI), (VII) and (VIII):

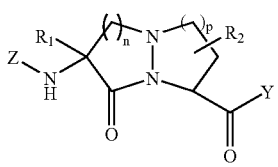
(VI)

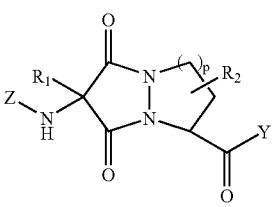
(VII)

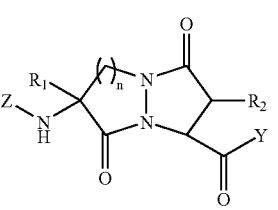
(VIII)

wherein $R_1$ and $R_2$ are independently selected from amino acid side chain moieties and derivatives thereof; n is an integer from 1 to 4; p is an integer from 1 to 3; and Y and Z represent the remainder of the molecule.

In preferred embodiments of this aspect of the invention, β-sheet mimetics are disclosed having the following structures (IX), (X) and (XI):

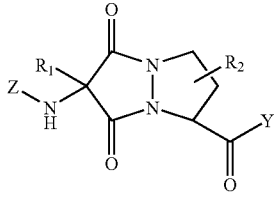
(IX)

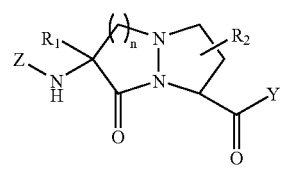
(X)

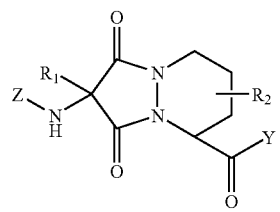
(XI)

wherein $R_1$ and $R_2$ are independently selected from amino acid side chain moieties and derivatives thereof; n is an integer from 1 to 4; and Y and Z represent the remainder of the molecule.

In a further preferred embodiment of this aspect of the invention, a β-sheet mimetic is disclosed of structure (X) above wherein n is 2, and having the following structure (Xa):

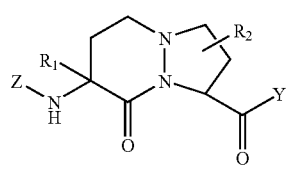
(Xa)

wherein $R_1$ and $R_2$ are independently selected from amino acid side chain moieties and derivatives thereof; and Y and Z represent the remainder of the molecule.

In another embodiment of structure (I) above, β-sheet mimetics are disclosed having the following structure (XII):

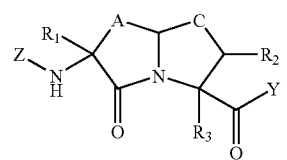
(XII)

wherein $R_1$, $R_2$ and $R_3$ are independently selected from amino acid side chain moieties and derivatives thereof; A is selected from —$(CH_2)_{1-4}$—, —$(CH_2)_{1-2}O$— and —$(CH_2)_{1-2}S$—, C is selected from —$(CH_2)_{1-3}$—, —O—, —S—, —$O(CH_2)_{1-2}$— and —$S(CH_2)_{1-2}$—; Y and Z represent the remainder of the molecule and the bicyclic ring system is saturated.

In an embodiment of structure (XII) where A is —(CH$_2$)$_{1-4}$—, β-sheet mimetics are disclosed having the following structure (XIII):

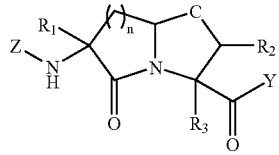

(XIII)

wherein R$_1$, R$_2$ and R$_3$ are independently selected from amino acid side chain moieties and derivatives thereof; n is an integer from 1 to 4; C is selected from —(CH$_2$)$_{1-3}$—, —O—, —S—, —O(CH$_2$)$_{1-2}$— and —S(CH$_2$)$_{1-2}$—; and Y and Z represent the remainder of the molecule.

In an embodiment of structure (XII) where A is —(CH$_2$)$_{1-2}$O— or —(CH$_2$)$_{12}$S—, β-sheet mimetics are disclosed having the following structures (XIV) and (XV):

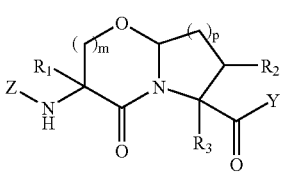

(XIV)

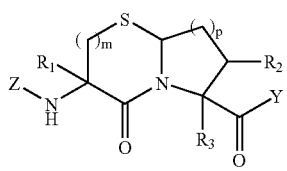

(XV)

wherein R$_1$, R$_2$ and R$_3$ are independently selected from amino acid side chain moieties and derivatives thereof; m is an integer from 1 to 2; p is an integer from 1 to 3; and Y and Z represent the remainder of the molecule.

In an embodiment of structure (XII) where C is —(CH$_2$)$_{1-3}$—, β-sheet mimetics are disclosed having the following structure (XVI):

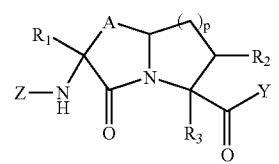

(XVI)

wherein R$_1$, R$_2$ and R$_3$ are independently selected from an amino acid side chain moiety and derivatives thereof; p is an integer from 1 to 3; A is selected from —(CH$_2$)$_{1-4}$—, —(CH$_2$)$_{1-2}$O— and —(CH$_2$)$_{1-2}$S—; and Y and Z represent the remainder of the molecule.

In an embodiment of structure (XII) where C is —O— or —S—, β-sheet mimetics are disclosed having the following structures (XVII) and (XVIII):

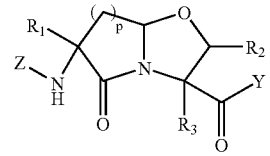

(XVII)

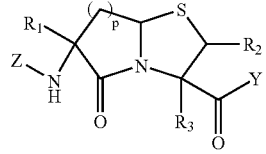

(XVIII)

wherein R$_1$, R$_2$ and R$_3$ are independently selected from amino acid side chain moieties and derivatives thereof; p is an integer from 1 to 3; and Y and Z represent the remainder of the molecule.

In an embodiment of structure (XII) where C is —O(CH$_2$)$_{1-2}$— or —S(CH$_2$)$_{1-2}$—, β-sheet mimetics are disclosed having the following structures (XIX) and (XX):

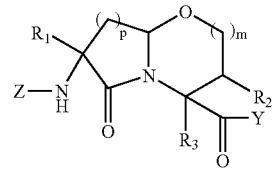

(XIX)

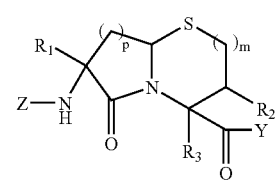

(XX)

wherein R$_1$, R$_2$ and R$_3$ are independently selected from amino acid side chain moieties and derivatives thereof; p is an integer from 1 to 3; m is an integer from 1 to 2; and Y and Z represent the remainder of the molecule.

In a further aspect of the present invention, β-sheet modified peptides or proteins are disclosed wherein a β-sheet mimetic of this invention is covalently attached to at least one amino acid of a naturally occurring or synthetic peptide or protein. In this embodiment, Y and/or Z in the above structures (I) through (XX) represent one or more amino acids of the peptide or protein. In a related embodiment, a method for imparting and/or stabilizing a β-sheet structure of a natural or synthetic peptide or protein is disclosed. This method includes covalently attaching one or more β-sheet mimetics of this invention within, or to the end of, a peptide or protein.

In yet a further embodiment, methods are disclosed for inhibiting a protease, kinase or MHC II in a warm-blooded animal by administering to the animal an effective amount of a compound of this invention.

Other aspects of this invention will become apparent upon reference to the following detailed description.

DETAILED DESCRIPTION OF THE INVENTION

Figure 1:
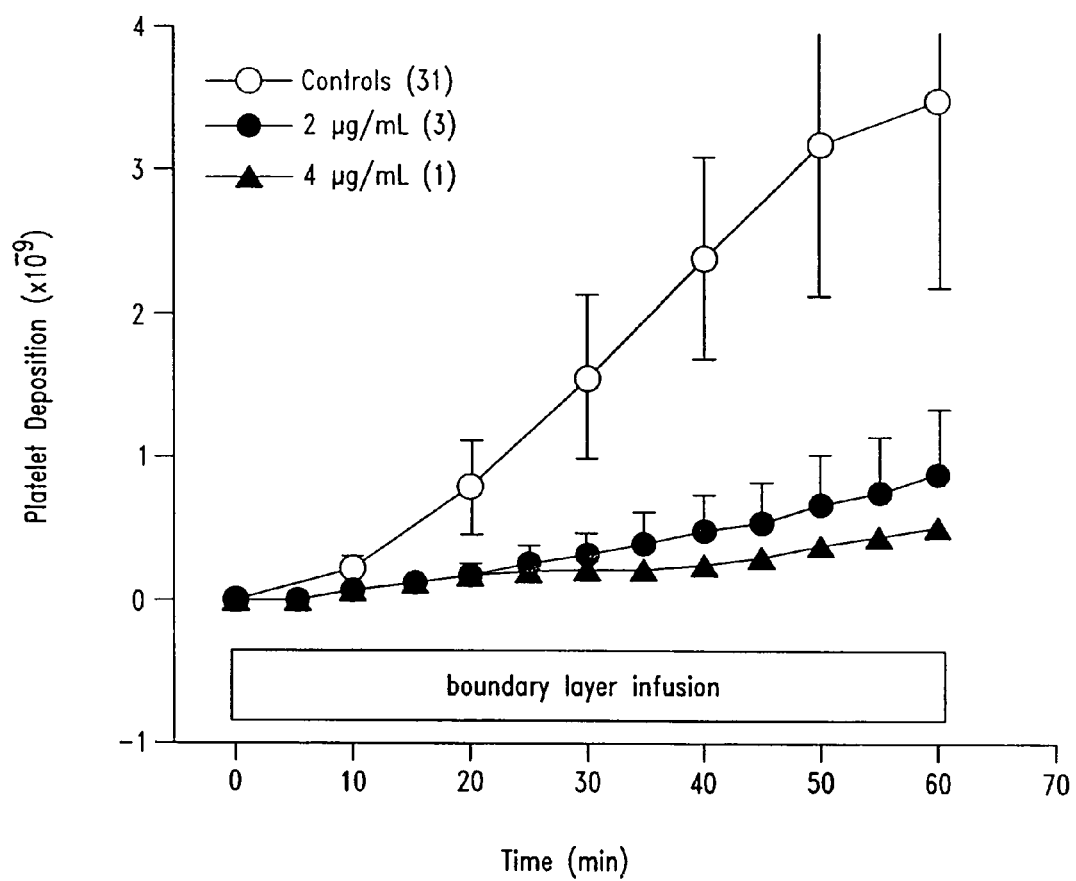
FIG. 1 is a plot showing the effect of various concentrations of structure (20b) on platelet deposition in a vascular graft.

As mentioned above, the β-sheet is an important structural component for many biological recognition events. The β-sheet mimetics of this invention serve to impart and/or stabilize the β-sheet structure of a natural or synthetic peptide, protein or molecule, particularly with regard to conformational stability. In addition, the β-sheet mimetics of this invention are more resistant to proteolytic breakdown, thus rendering a peptide, protein or molecule containing the same more resistant to degradation.

The β-sheet mimetics of this invention are generally represented by structure (I) above, as well as the more specific embodiments represented by structures (II) through (XX), and have stereochemistries represented by structures (I') through (I''''') below:

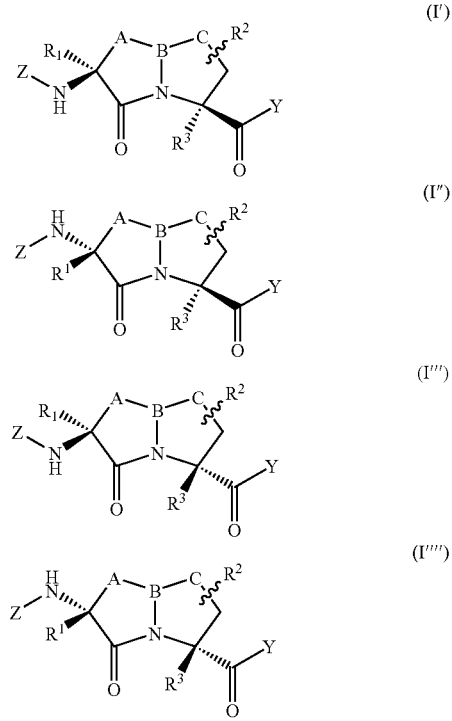

wherein $R_1$, $R_2$, $R_3$, A, B, C, Y and Z are as defined above. In other words, all stereoisomers of structure (I), as well as the more specific embodiments represented by structures (II) through (XX), are included within the scope of this invention. For example, the β-sheet mimetics of this invention may be constructed to mimic the three-dimensional conformation of a β-sheet comprised of naturally occurring L-amino acids, as well as the structure of a β-sheet comprised of one or more D-amino acids. In a preferred embodiment, the β-sheet mimetic has the stereoconformation of structure (I') or (I'').

As used in the context of this invention, the term "remainder of the molecule" (as represented by Y and Z in structures (I) through (XX) above) may be any chemical moiety. For example, when the β-sheet mimetic is located within the length of a peptide or protein, Y and Z may represent amino acids of the peptide or protein. Alternatively, if two or more β-sheet mimetics are linked, the Y moiety of a first β-sheet mimetic may represent a second β-sheet mimetic while, conversely, the Z moiety of the second β-sheet mimetic represents the first β-sheet mimetic. When the β-sheet mimetic is located at the end of a peptide or protein, or when the β-sheet mimetic is not associated with a peptide or protein, Y and/or Z may represent a suitable terminating moiety. Representative terminating moieties for the Z moiety include, but are not limited to, —H, —OH, —R, —C(═O)R and —SO₂R (where R is a C1-C8 alkyl or aryl moiety), or may be a suitable protecting group for protein synthesis, such as BOC, FMOC or CBZ (i.e., tert-butyloxycarbonyl, 9-fluorenylmethoxycarbonyl, and benzyloxycarbonyl, respectively). Similarly, representative terminating moieties for the Y moiety include, but are not limited to, —H, —OH, —R, —NHOH, —NHNHR, —C(═O)OR, —C(═O)NHR, —CH₂Cl, —CF₃, —C₂F₅, —CHN₂,

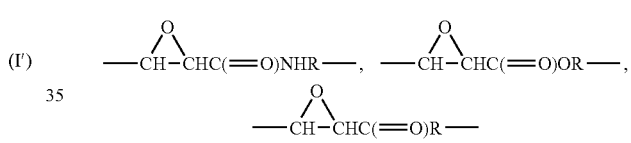

(where R is a C1-C8 alkyl or aryl moiety), or a heterocyclic moiety, such as pyridine, pyran, thiophan, pyrrole, furan, thiophene, thiazole, benzthiazole, oxazole, benzoxazole, imidazole and benzimidazole.

As used herein, the term "an amino acid side chain moiety" represents any amino acid side chain moiety present in naturally occurring proteins, including (but not limited to) the naturally occurring amino acid side chain moieties identified in Table 1 below. Other naturally occurring side chain moieties of this invention include (but are not limited to) the side chain moieties of 3,5-dibromotyrosine, 3,5-diiodotyrosine, hydroxylysine, naphthylalanine, thienylalanine, γ-carboxyglutamate, phosphotyrosine, phosphoserine and glycosylated amino acids such as glycosylated serine, asparagine and threonine.

TABLE 1

| Amino Acid Side Chain Moiety | Amino Acid |
|---|---|
| —H | Glycine |
| —CH₃ | Alanine |
| —CH(CH₃)₂ | Valine |
| —CH₂CH(CH₃)₂ | Leucine |
| —CH(CH₃)CH₂CH₃ | Isoleucine |
| —(CH₂)₄NH₃⁺ | Lysine |
| —(CH₂)₃NHC(NH₂)NH₂⁺ | Arginine |

TABLE 1-continued

| Amino Acid Side Chain Moiety | Amino Acid |
|---|---|
| —CH$_2$—[imidazole ring with HN and NH$^+$] | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
| —CH$_2$—[phenyl] | Phenylalanine |
| —CH$_2$—[phenyl]—OH | Tyrosine |
| —CH$_2$—[indole] | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |

In addition to naturally occurring amino acid side chain moieties, the amino acid side chain moieties of the present invention also include various derivatives thereof. As used herein, a "derivative" of an amino acid side chain moiety includes all modifications and/or variations to naturally occurring amino acid side chain moieties. For example, the amino acid side chain moieties of alanine, valine, leucine, isoleucine and phenylalanine may generally be classified as lower chain alkyl, aryl or aralkyl moieties. Derivatives of amino acid side chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1-12 carbon atoms, "lower chain aryl moieties" contain from 6-12 carbon atoms, and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ aralkyl, and in a more preferred embodiment, from a $C_{1-7}$ alkyl, a $C_{6-10}$ aryl and a $C_{7-11}$ aralkyl.

Amino acid side chain derivatives of this invention further include substituted derivatives of lower chain alkyl, aryl and aralkyl moieties, wherein the substituent is selected from (but are not limited to) one or more of the following chemical moieties: —OH, —OR, —R, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from a lower chain alkyl, aryl or aralkyl moiety. For example, the methylene moiety of the aralkyl moiety benzyl (i.e., —CH$_2$phenyl) may be substituted with phenyl, yielding —CH(phenyl)$_2$. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Bicyclic lactams are known in the art. See, e.g., Columbo, L. et al., *Tet. Lett.* 36(4):625-628, 1995; Baldwin, J. E. et al., *Heterocycles* 34(5):903-906, 1992; and Slomczynska, U. et al., *J. Org. Chem.* 61:1198-1204, 1996. However, the bicyclic lactams of the invention are not disclosed in these references.

As mentioned above, the β-sheet mimetics of this invention serve to impart and/or stabilize the β-sheet structure of a protein, peptide or molecule. The β-sheet mimetic may be positioned at either the C-terminus or N-terminus of the protein, peptide or molecle, or it may be located within the protein, peptide or molecule itself. In addition, more than one β-sheet mimetic of the present invention may be incorporated in a protein, peptide or molecule.

The β-sheet mimetics of this invention may be synthesized by a number of reaction schemes. For example, the various embodiments of structure (I) may be synthesized according to the following reaction schemes (1) through (17).

Reaction Scheme (1)

Structure (III) and representative compounds thereof having structure (IIIA) can be synthesized by the following reaction schemes:

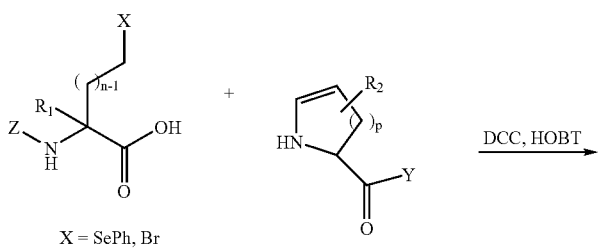

X = SePh, Br

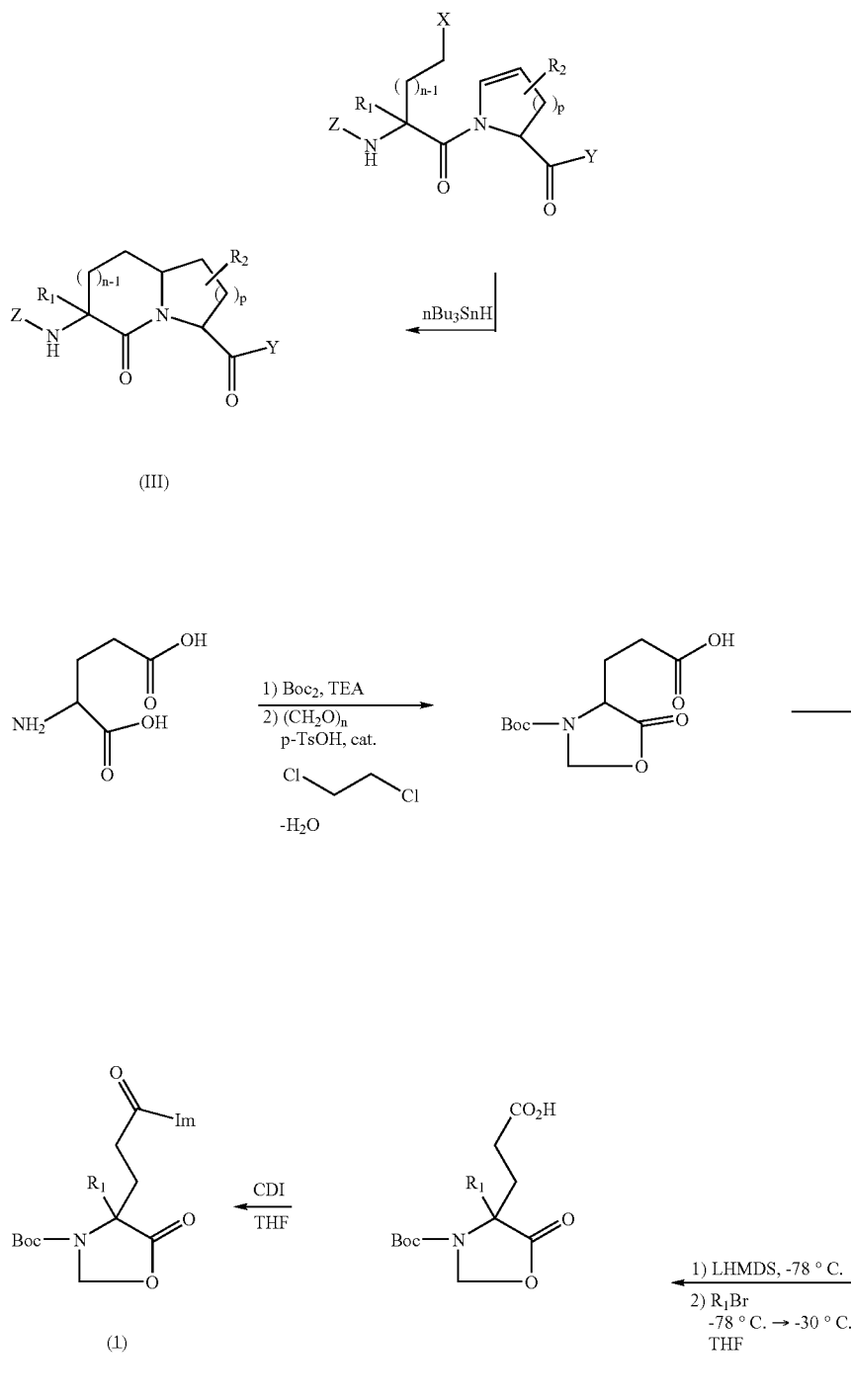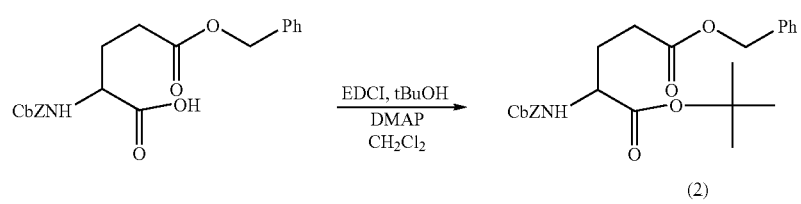

(2) →[1) LHMDS (2.5 eq.)][2) (1)]

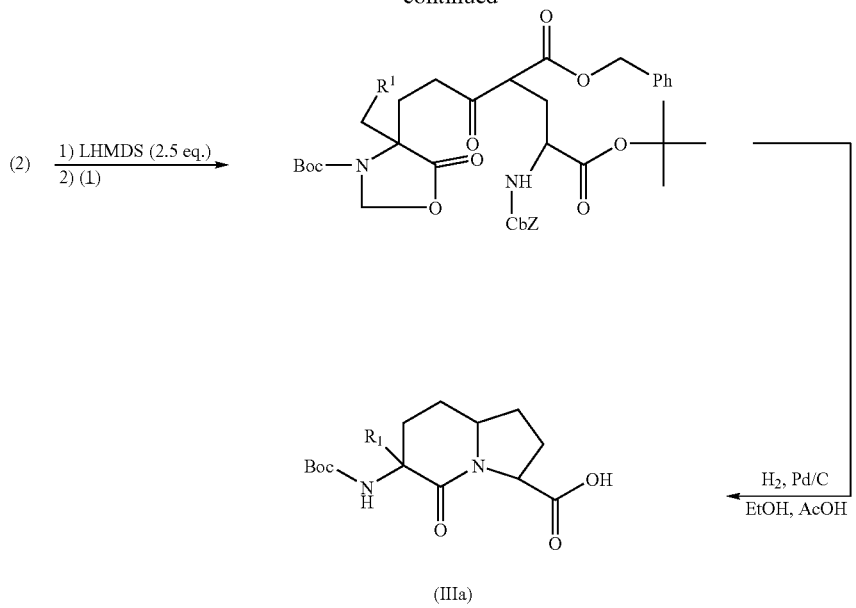

(IIIa)

←[H₂, Pd/C][EtOH, AcOH]

Reaction Scheme (2)

Structure (IV) can be synthesized by the following reaction scheme:

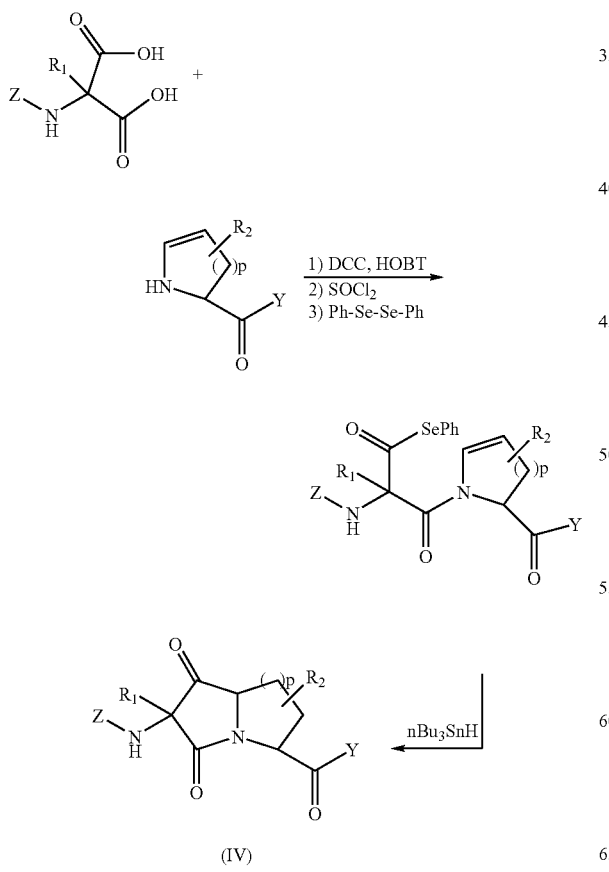

(IV)

Reaction Scheme (3)

Representative compounds of structure (V) having structure (Va) can be synthesized by the following reaction scheme, where structure (Ia) in scheme (3) is a representative structure of the invention having a double bond in the bicyclic ring system:

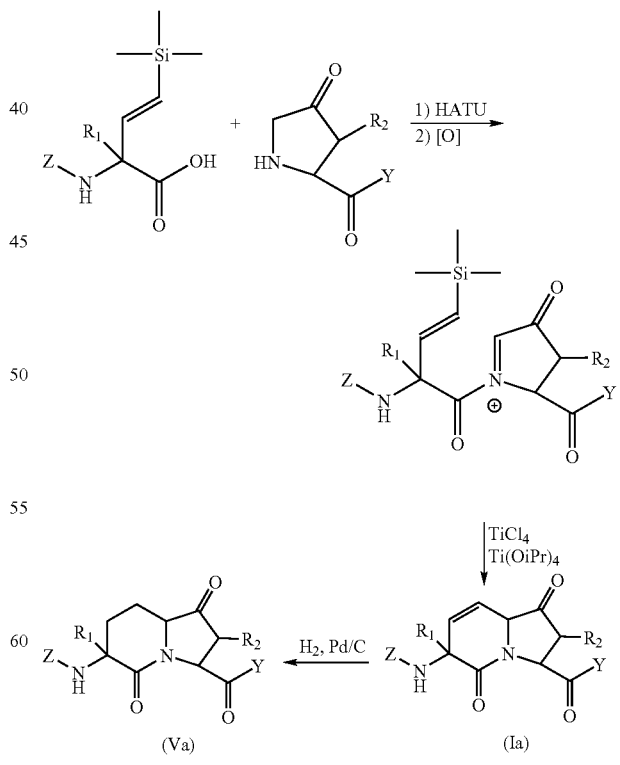

(Va)  (Ia)

In addition, representative compounds of structure (V) having structure (Vb) may be synthesized by the following reaction scheme, and when A of structure (II) is —C(=O)(CH$_2$)$_{1-3}$—, a related compound (designated (IIa) below) can be synthesized by the following reaction scheme:

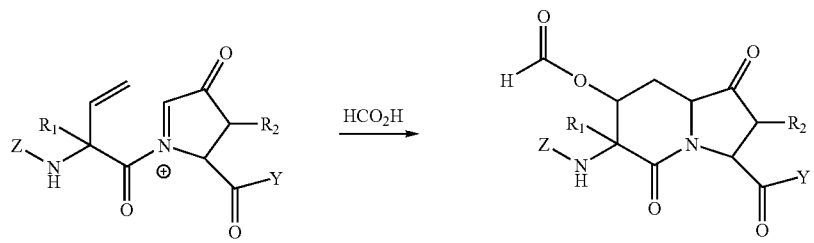

 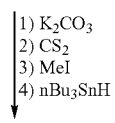

1) OH$^\ominus$
2) [O] (PCC)

1) K$_2$CO$_3$
2) CS$_2$
3) MeI
4) nBu$_3$SnH

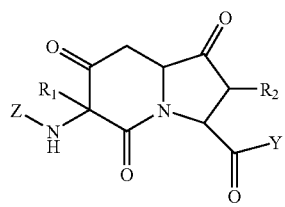 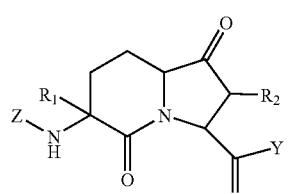

(IIa)            (Vb)

Reaction Scheme (4)

Representative compounds of structure (VI) having structures (VIa) and (VIb) below, wherein R$_3$ is hydrogen, can be synthesized by the following reaction scheme (see Holmes and Neel, Tet. Lett. 31:5567-70, 1990):

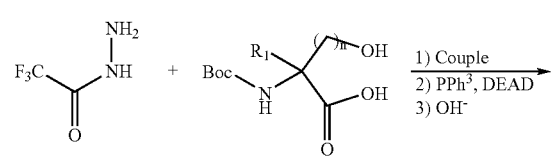

1) Couple
2) PPh$^3$, DEAD
3) OH$^-$

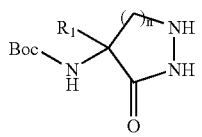

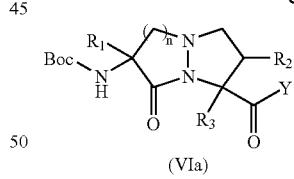
(VIa)

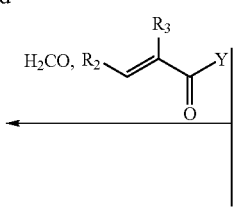

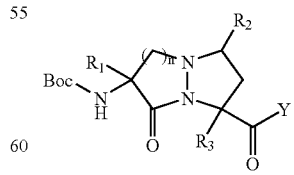
(VIb)

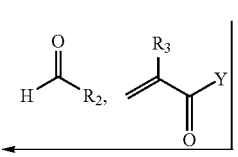

Representative compounds of structure (II) wherein R$_3$ is an amino acid side chain moiety or derivative thereof may also be prepared according to the above scheme (4).

Reaction Scheme (5)
Representative compounds of structure (VII) having structure (VIIa) can be synthesized by the following reaction scheme:
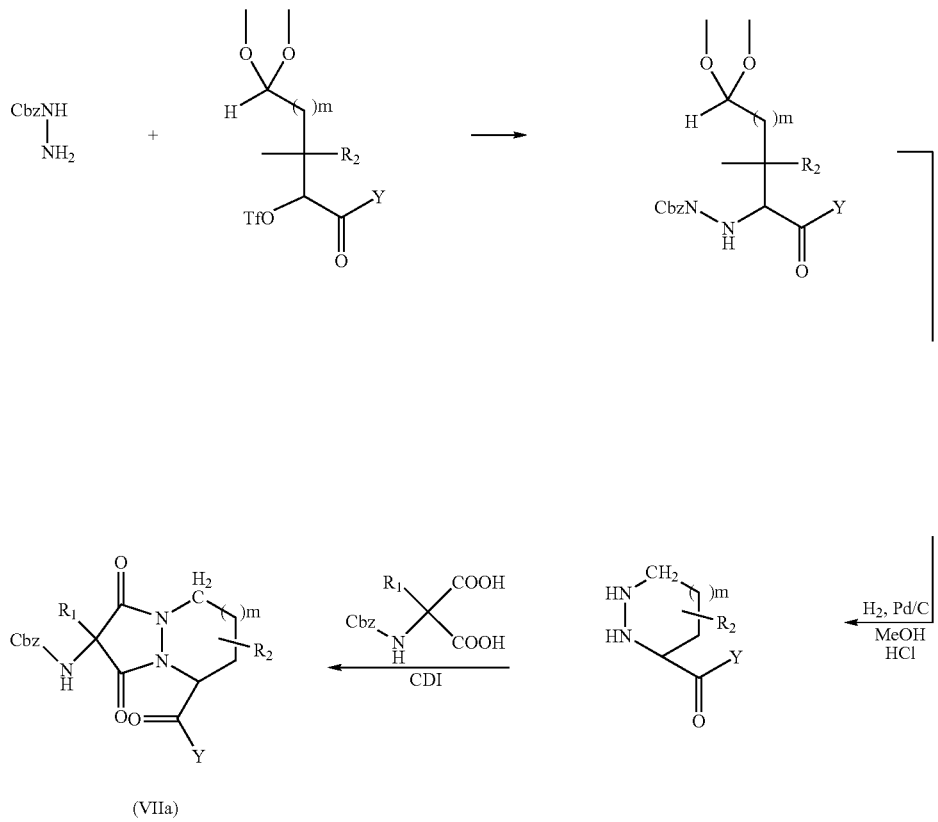
(VIIa)
Reaction Scheme (6)
Structure (VIII) can be synthesized by the following reaction scheme:
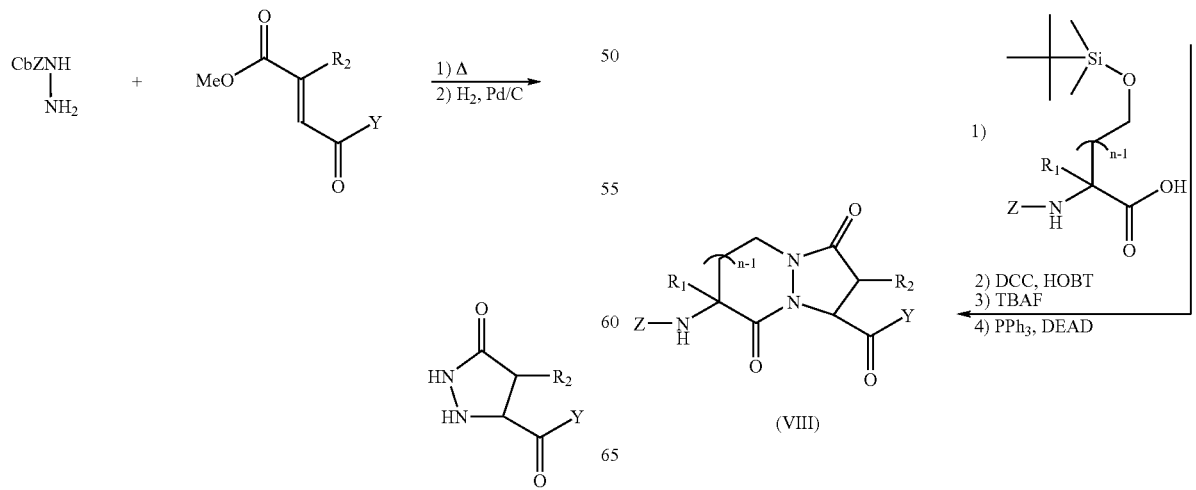
(VIII)
-continued Reaction Scheme (7)
Representative compounds of structure (IX) having structures (IXa) and (IXb) shown below, can be synthesized by the following reaction scheme:
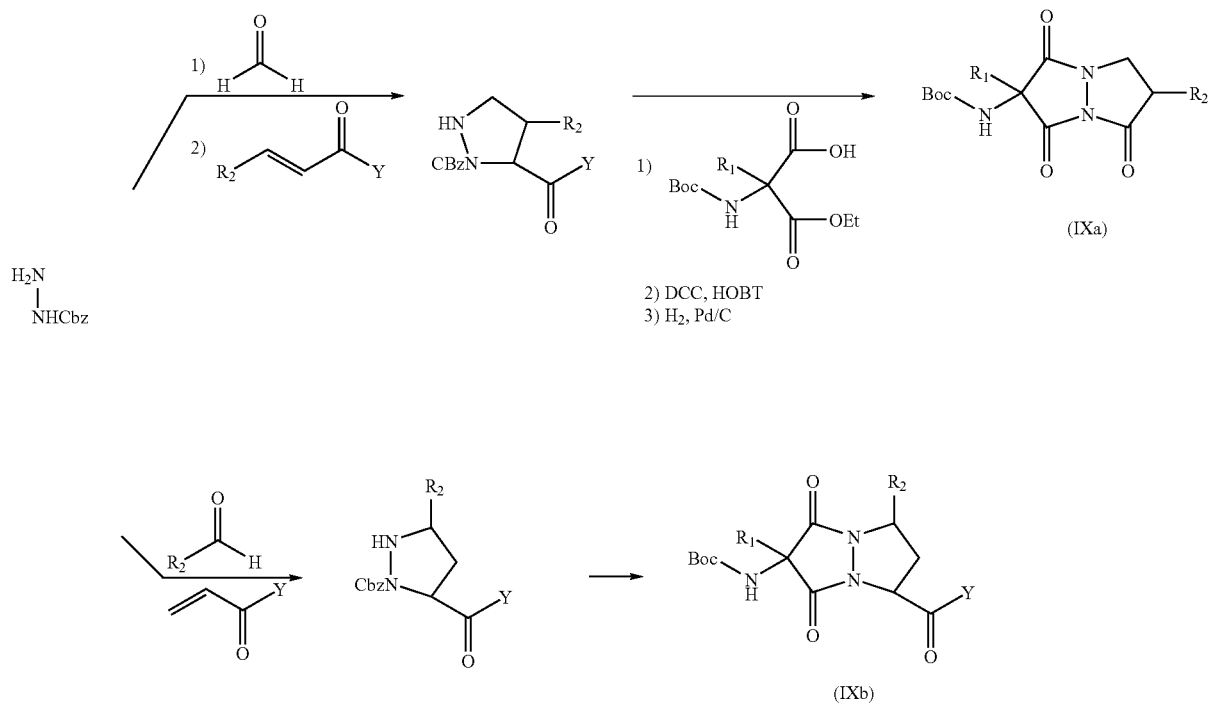
Reaction Scheme (8)
Representative compounds of structure (X) having structures (Xb) and (Xc) can be synthesized by the following reaction scheme (see Jungheim & Sigmund, *J. Org. Chem.* 52:4007-4013, 1987):
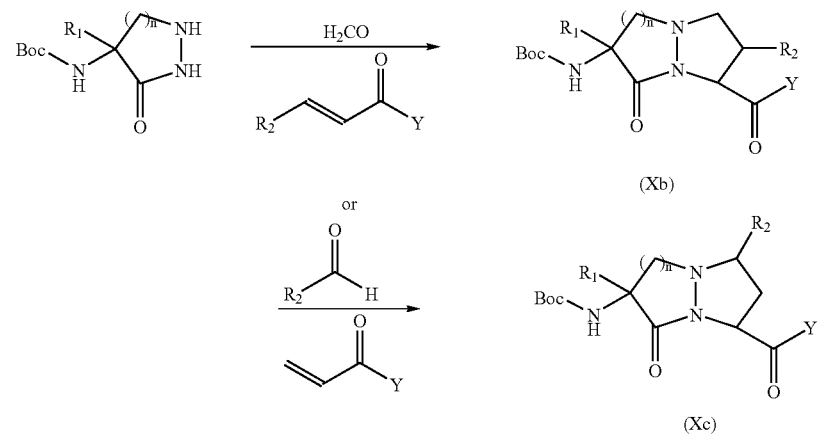

Reaction Scheme (9)
Structure (XI) may be synthesized by the following reaction scheme (see Perkin, *J. Chem. Soc. Perk. Trans.* 1:155-164, 1984):
Reaction Scheme (10)
Structure (XIII) may be synthesized by the following reaction scheme:
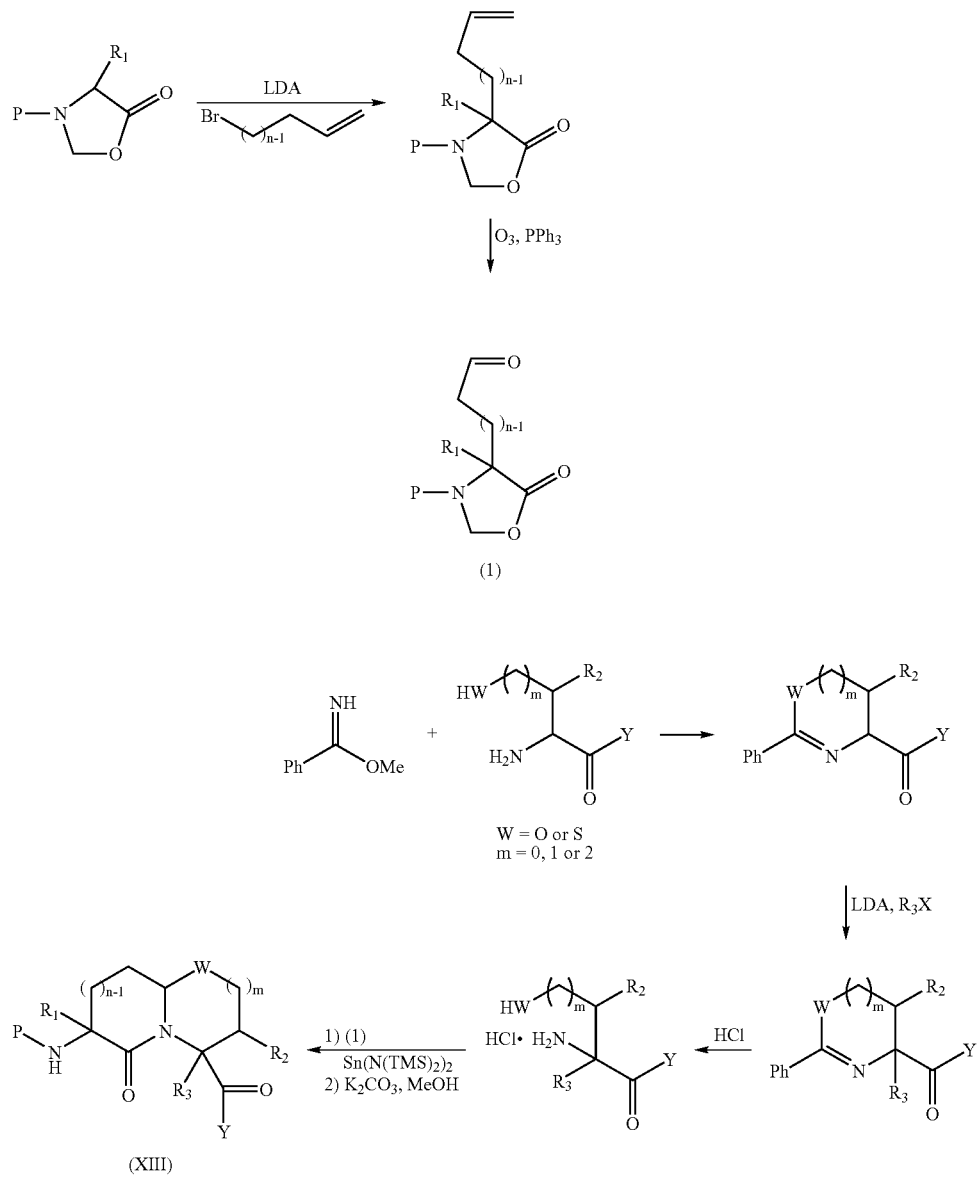
W = O or S
m = 0, 1 or 2

Reaction Scheme (11)
Structures (XIV) and (XV) may be synthesized by the following scheme:
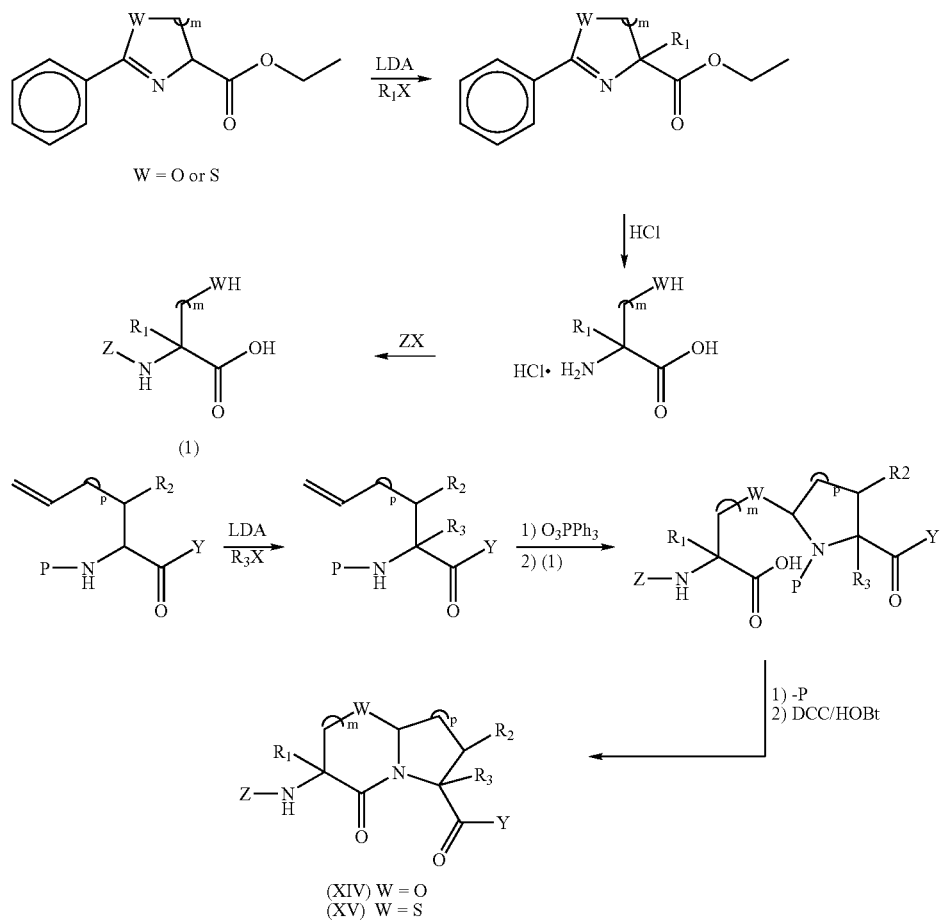
Reaction Scheme (12)
Structure (XVI) may be synthesized by the following reaction scheme:
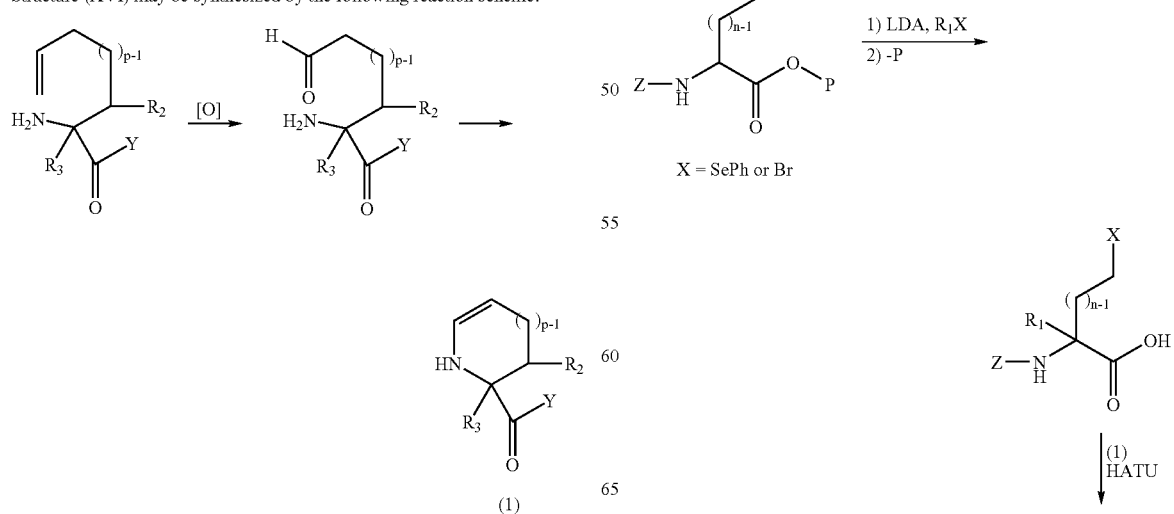

-continued
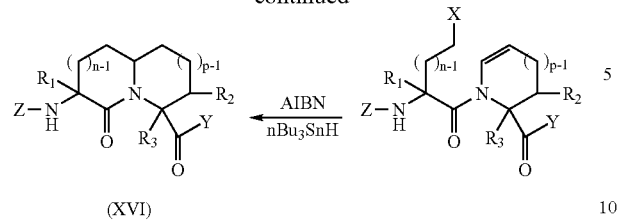
(XVI)
Reaction Scheme (13)
Structures (XVII) and (XVIII) may be synthesized by the following reaction scheme:
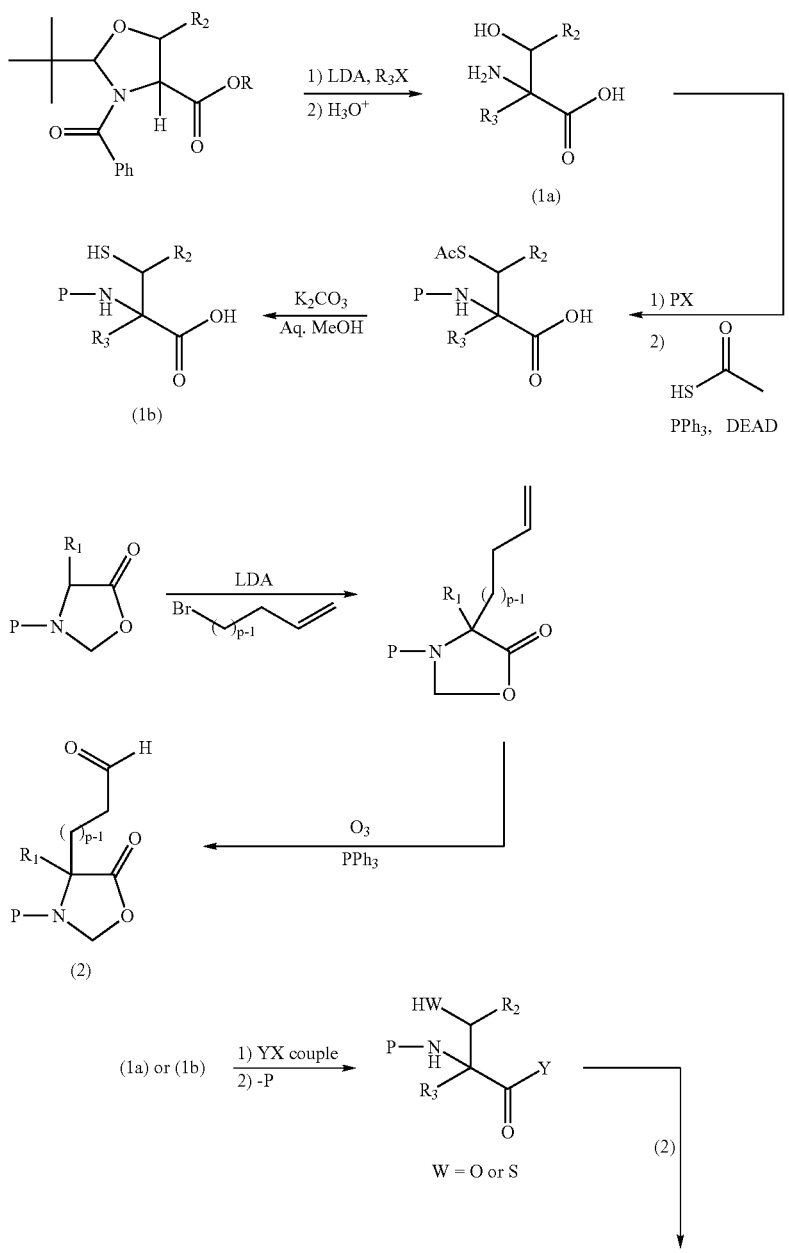

-continued
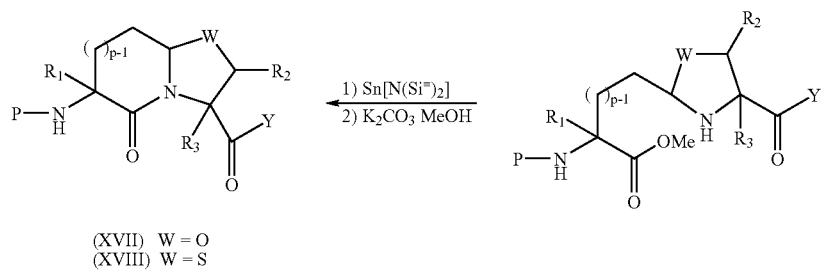
(XVII) W = O
(XVIII) W = S
Reaction Scheme (14)
Structures (XIX) and (XX) may be synthesized by the following reaction scheme:
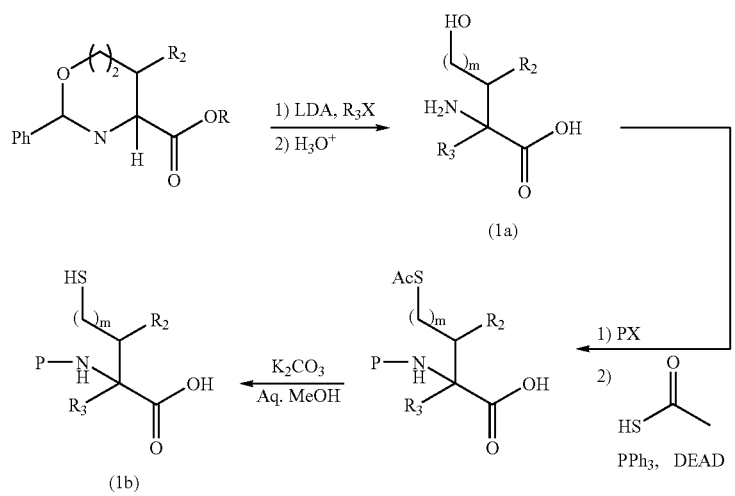
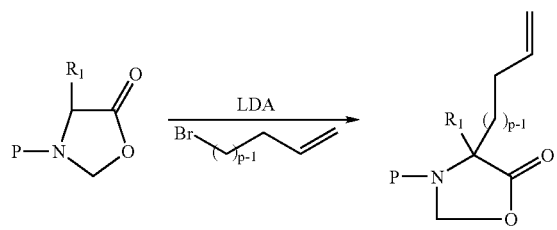
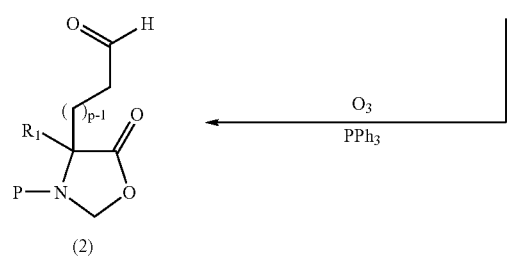

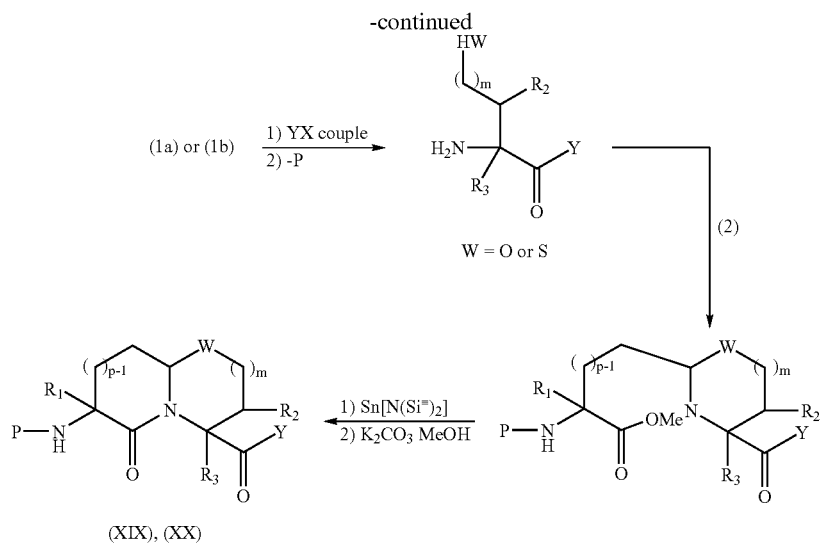

According to the definition of structure (I) above, the bicyclic ring system may contain adjacent CH groups (i.e., the bicyclic ring system may be formed, at least in part, by a —CH—CH— group). Compounds wherein such a —CH—CH— group is replaced with a —C=C— are also included within the scope of structure (I) (i.e., any two adjacent CH groups of the bicyclic ring may together form a double bond).

Reaction Schemes (15), (16) and (17) illustrate synthetic methodology for preparing representative compounds of structure (I) wherein the bicyclic ring system is formed in part by a —C=C— group.

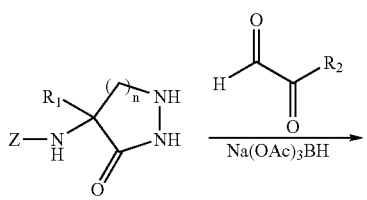

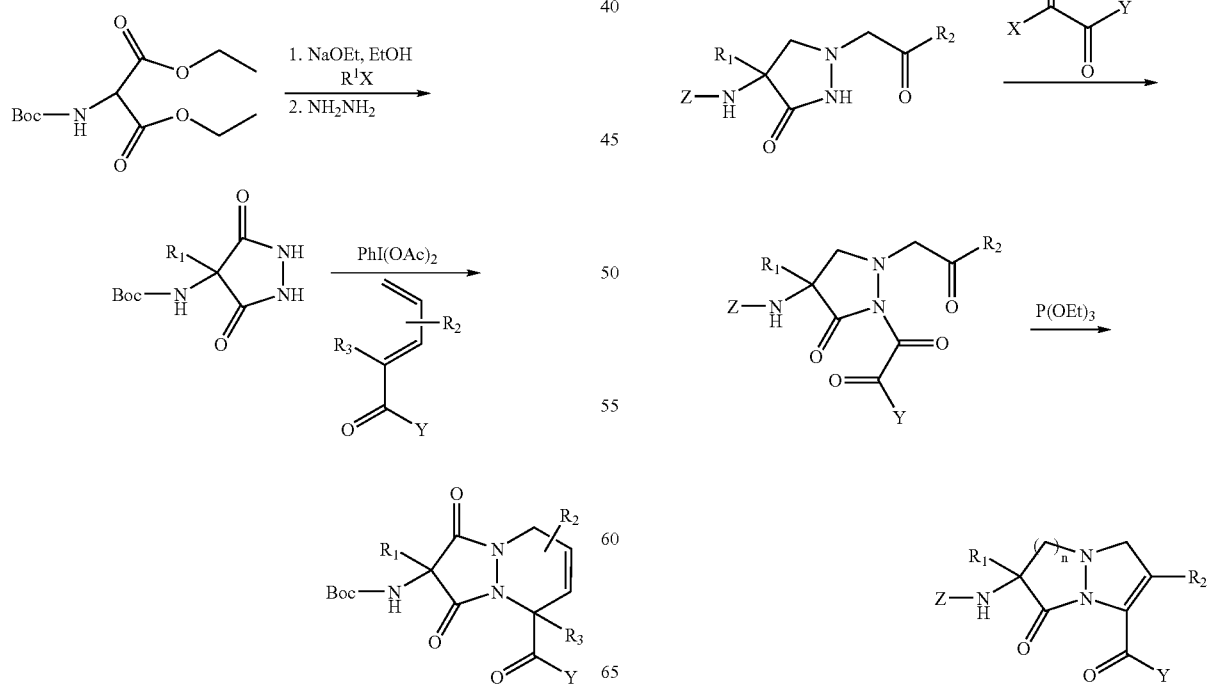

Reaction Scheme (17)

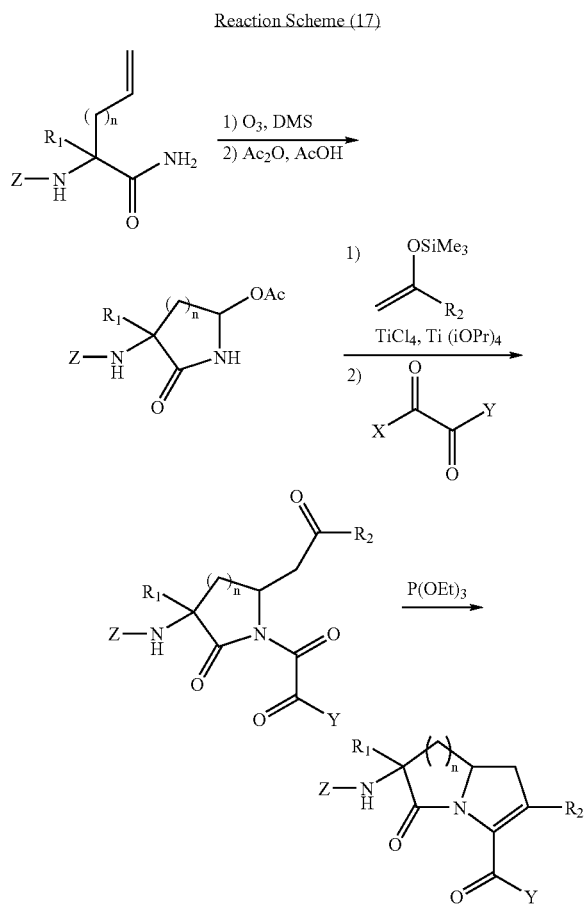

In β-sheet mimetics of the invention, preferred Y groups have the structure:

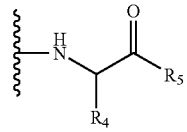

where a preferred stereochemistry is:

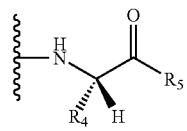

Preferred $R_4$ groups are organoamine moieties having from about 2 to about 10 carbon atoms and at least one nitrogen atom. Suitable organoamine moieties have the chemical formula $C_{2-10}H_{4-20}N_{1-6}O_{0-2}$; and preferably have the chemical formula $C_{3-7}H_{7-14}N_{1-4}O_{0-1}$. Exemplary organoamine moieties of the invention are (wherein R is selected from hydrogen, halogen (e.g., fluorine), lower chain alkyl (e.g., methyl), and hydroxy lower chain alkyl (e.g., hydroxymethyl); and X is selected from $CH_2$, NH, S and O):

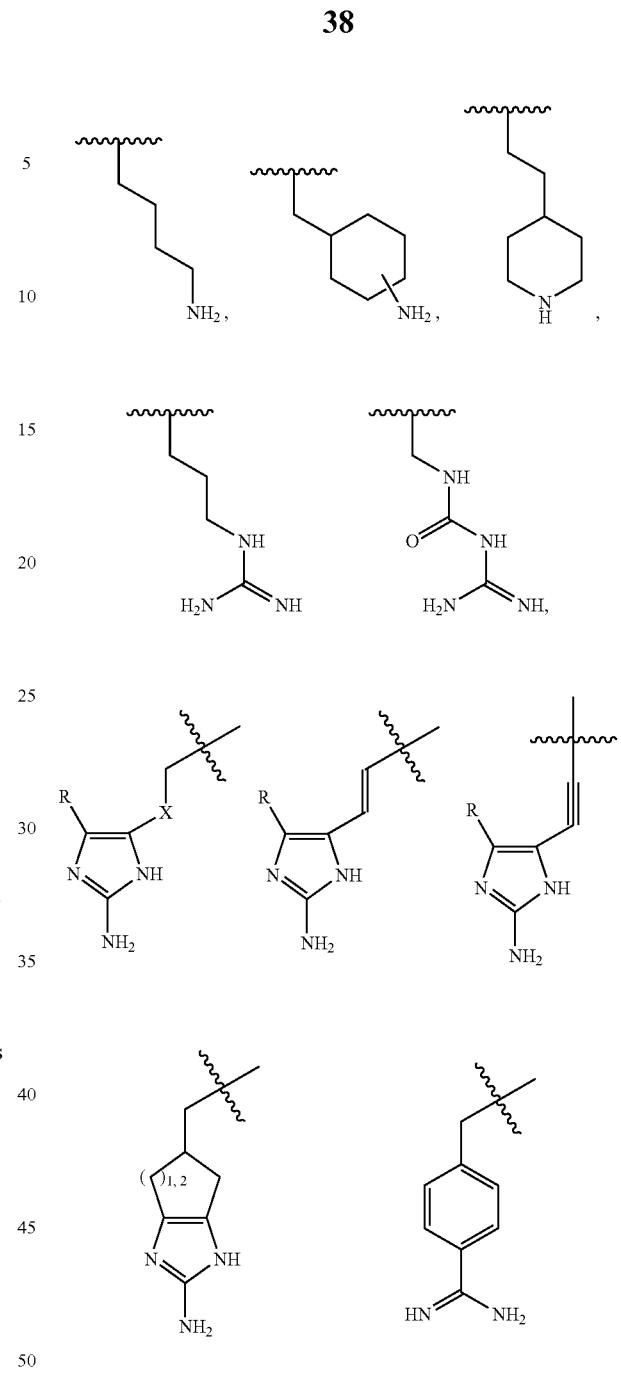

In the above structure, $R_5$ is selected from (a) alkyl of 1 to about 12 carbon atoms, optionally substituted with 1-4 of halide, $C_{1-5}$alkoxy and nitro, (b) —C(=O)NH—$C_{1-5}$alkyl, wherein the alkyl group is optionally substituted with halide or $C_{1-5}$alkoxy, (c) —C(=O)NH—$C_{1-10}$aralkyl where the aryl group may be optionally substituted with up to five groups independently selected from nitro, halide, —NH—(C=O)$C_{1-5}$alkyl, —NH—(C=O)$C_{6-10}$aryl, $C_{1-5}$alkyl and $C_{1-5}$alkoxy, and (d) monocyclic and bicyclic heteroaryl of 4 to about 11 ring atoms, where the ring atoms are selected from carbon and the heteroatoms oxygen, nitrogen and sulfur, and where the heteroaryl ring may be optionally substituted with up to about 4 of halide, $C_{1-5}$alkyl, $C_{1-5}$alkoxy, —C(=O)NH$C_{1-5}$alkyl, —C(=O)NH$C_{6-10}$aryl, amino, —C(=O)O$C_{1-5}$alkyl and —C(=O)O$C_{6-10}$aryl.

Preferred $R_5$ groups are:

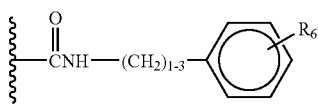

wherein $R_6$ is hydrogen, nitro, halide, NH—C(=O)—$C_{1-5}$alkyl, NH—C(=O)—$C_{6-10}$aryl, $C_1$-$C_5$alkyl and $C_1$-$C_5$alkoxy;

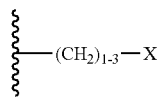

wherein X is halide;

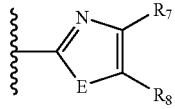

wherein E is —O—, —NH— or —S— and $R_7$ and $R_8$ are independently selected from hydrogen, $C_{1-5}$alkyl, —C(=O)O$C_{1-5}$alkyl, —C(=O)O$C_{6-10}$aryl, —C(=O)NH$C_{1-5}$alkyl and —C(=O)NH$C_{6-10}$aryl; and

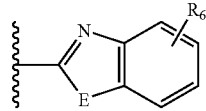

wherein E and $R_6$ are as defined previously.

In a further embodiment of this invention, β-sheet mimetics of the present invention have the following structure (XXI):

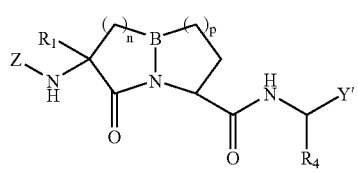

(XXI)

wherein n is an integer from 1 to 4; p is an integer from 1 to 3; B is selected from N and CH; $R_1$ is selected from amino acid side chain moieties and derivatives thereof; $R_4$ is selected from amino acid side chain moieties of arginine and derivatives thereof; and Y' and Z represent the remainder of the molecule. In a preferred aspect of this embodiment, $R_1$ is selected from amino acid side chain moieties and derivatives thereof other than hydrogen. In a further preferred aspect, n is an integer from 1 to 2 and p is an integer from 1 to 2.

In a further aspect of this embodiment n is 2 and p is 1, yielding the following structure (XXII):

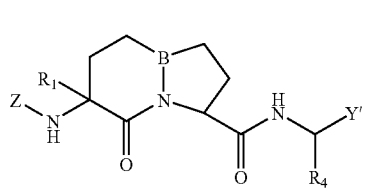

(XXII)

wherein $R_1$, $R_4$, B, Y' and Z are as defined above. In a preferred embodiment, Y' is —C(=O)$R_5$, wherein $R_5$ is as defined above. In a further preferred emdodiment, the above structure has the following stereochemistry (XXII'):

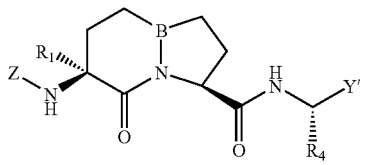

(XXII')

The β-sheet mimetics of the present invention may be used in standard peptide synthesis protocols, including automated solid phase peptide synthesis. Peptide synthesis is a stepwise process where a peptide is formed by elongation of the peptide chain through the stepwise addition of single amino acids. Amino acids are linked to the peptide chain through the formation of a peptide (amide) bond. The peptide link is formed by coupling the amino group of the peptide to the carboxylic acid group of the amino acid. The peptide is thus synthesized from the carboxyl terminus to the amino terminus. The individual steps of amino acid addition are repeated until a peptide (or protein) of desired length and amino acid sequence is synthesized.

To accomplish peptide (or protein or molecule) synthesis as described above, the amino group of the amino acid to be added to the peptide should not interfere with peptide bond formation between the amino acid and the peptide (i.e., the coupling of the amino acid's carboxyl group to the amino group of the peptide). To prevent such interference, the amino groups of the amino acids used in peptide synthesis are protected with suitable protecting groups. Typical amino protecting groups include, for example, BOC and FMOC groups. Accordingly, in one embodiment of the present invention, the β-sheet mimetics of the present invention bear a free carboxylic acid group and a protected amino group, and are thus suitable for incorporation into a peptide by standard synthetic techniques.

The β-sheet mimetics of this invention have broad utility in naturally occurring or synthetic peptides, proteins and molecules. For example, the β-sheet mimetics disclosed herein have activity as inhibitors of kinases and proteases, as well as having utility as MHC II inhibitors. For example, the β-sheet mimetics of this invention have activity as inhibitors of the large family of trypsin-like serine proteases, including those preferring arginine or lysine as a P' substituent. These enzymes are involved in blood coagulation, and include (but are not limited to) Factor VIIa, Factor IXa, Factor Xa, Factor XIa, thrombin, kallikrein, tryptase, urokinase (which is also involved in cancer metastasis) and plasmin. Thus, the ability to selectively inhibit these enzymes has wide utility in therapeutic applications involving cardiovascular disease and oncology.

For example, the following β-sheet mimetics can be synthesized on solid support (e.g., PAM resin):

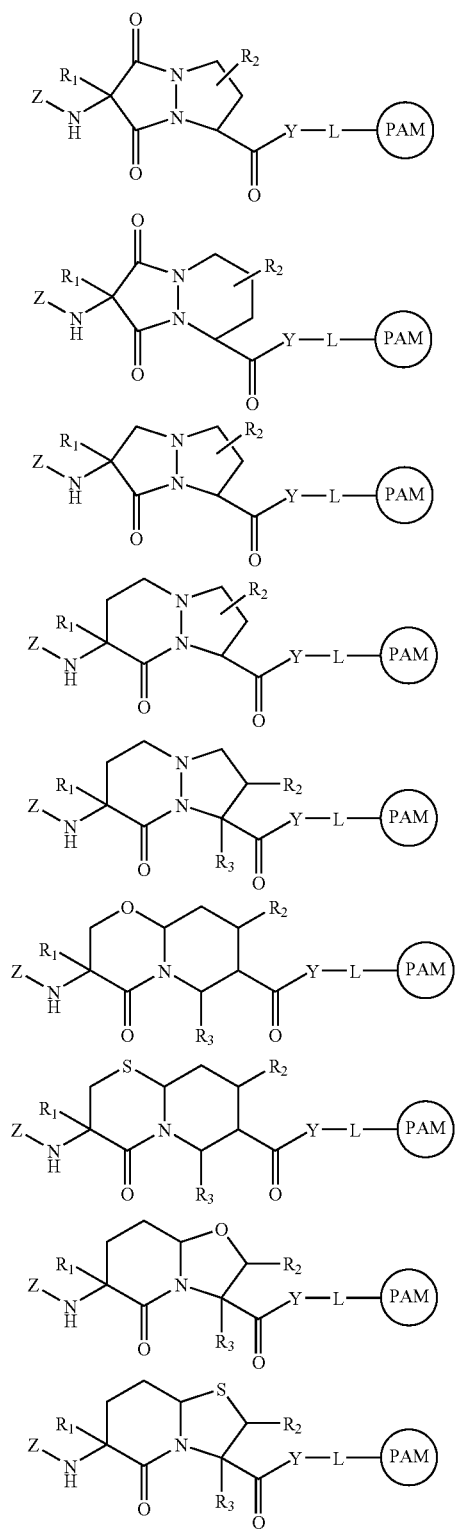

In the above β-sheet mimetics, L is an optional linker.

The β-sheet mimetics may then be cleaved from the solid support by, for example, aminolysis, and screened as competitive substrates against appropriate agents, such as the chromogenic substrate BAPNA (benzyoylarginine paranitroanalide) (see Eichler and Houghten, *Biochemistry* 32:11035-11041, 1993) (incorporated herein by reference). Alternatively, by employing a suitable linker moiety, such screening may be performed while the β-sheet mimetics are still attached to the solid support.

Once a substrate is selected by the above kinetic analysis, the β-sheet mimetic may be converted into an inhibitor by modifications to the C-terminal—that is, by modification to the Y moiety. For example, the terminal Y moiety may be replaced with —CH$_2$Cl, —CF$_3$, —H, or —C(O)NHR. Appropriate R moieties may be selected using a library of substrates, or using a library of inhibitors generated using a modification of the procedure of Wasserman and Ho (*J. Org. Chem.* 59:4364-4366, 1994) (incorporated herein by reference).

Libraries of compounds containing β-strand templates may be constructed to determine the optimal sequence for substrate recognition or binding. Representative strategies to use such libraries are discussed below.

A representative β-sheet mimetic substrate library may be constructed as follows. It should be understood that the following is exemplary of methodology that may be used to prepare a β-sheet mimetic substrate library, and that other libraries may be prepared in an analogous manner.

In a first step, a library of the following type:

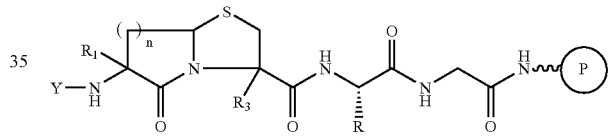

R$_1$, R$_3$, R=amino acid side chain moieities or derivatives thereof; Y=H, Ac, SO$_2$R; and the circled "P" represents a solid support.

may be constructed on a solid support (PEGA resin, Meldal, M. *Tetrahedron Lett.* 33:3077-80, 1992; controlled pore glass, Singh et al., *J. Med. Chem.* 38:217-19, 1995). The solid support may then be placed in a dialysis bag (Bednarski et al., *J. Am. Chem. Soc.* 109:1283-5, 1987) with the enzyme (e.g., a protease) in an appropriate buffer. The bag is then placed in a beaker with bulk buffer. The enzymatic reaction is monitored as a function of time by HPLC and materials cleaved from the polymer are analyzed by MS/MS. This strategy provides information concerning the best substrates for a particular target.

The synthesis of the β-sheet mimetic is illustrated by the retrosynthetic procedure shown next:

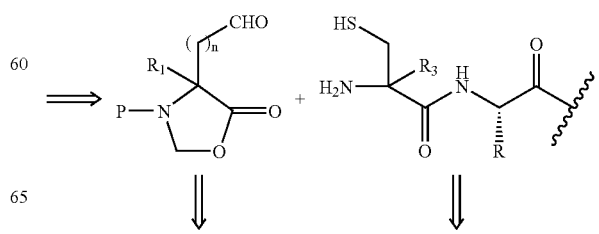

-continued

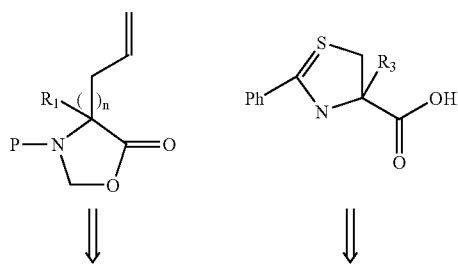

⇓

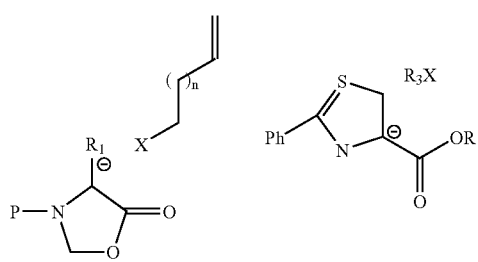

The complexity of the library generated by this technique is $(R_1)$ $(R_3)$ (R) (Y). Assuming $R_1$, $R_3$ and R are selected from naturally occurring amino acid side chains moieties, n is constant, and Y is H, Ac or $-SO_2R$ as defined above, a library having on the order of 24,000 members [(20) (20) (20) (3)] is generated.

After screening the library against a specific target (e.g., enzyme), the library may then recovered and screened with a second target, and so on.

In addition, a library of inhibitors can be constructed and screened in a standard chromogenic assay. For example, the library may be constructed as follows, where the following example is merely representative of the inhibitor libraries that may be prepared in an analogous manner to the specific example provided below.

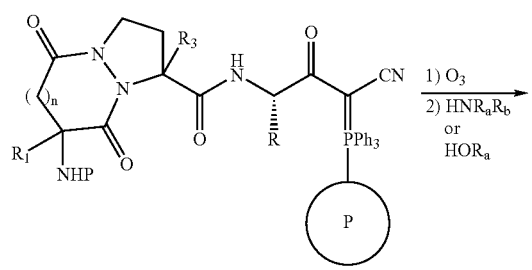

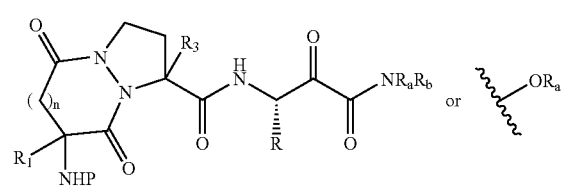

inhibitors of serine or cysteinyl proteases (See Wasserman et al., *J. Org. Chem.* 59:4364-6, 1994.)

A further alternative strategy is to link the library through the sidechain R group as shown below.

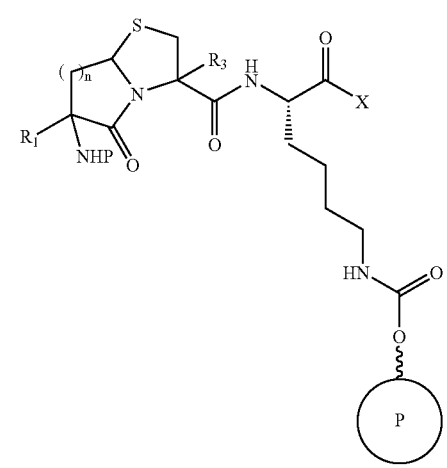

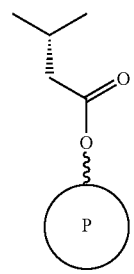 for Asp or Glu  X = $CF_3$, NHOH,

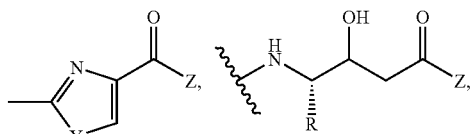

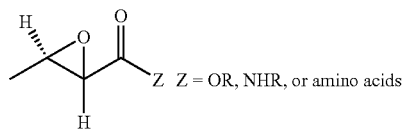 Z = OR, NHR, or amino acids

A library of aspartic protease inhibitors may be constructed having the following exemplary structure, and then cleaved from the resin and screened:

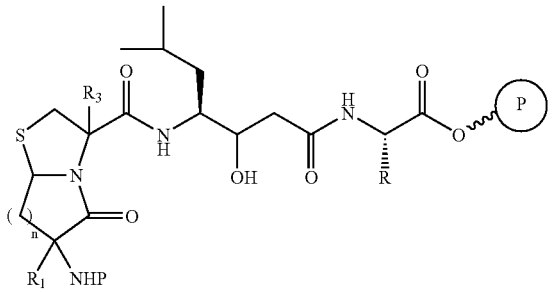

Similarly, for metalloproteases, a library having the exemplary structure shown below may be constructed and then cleaved from the resin to provide a library of hydroxamic acids:

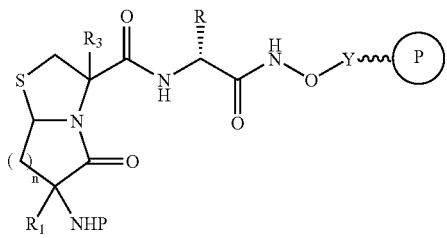

The activity of the β-sheet mimetics of this invention may be further illustrated by reference to Table 2 which lists a number of biologically active peptides. In particular, the peptides of Table 2 are known to have biological activity as substrates or inhibitors.

TABLE 2

Biologically Active Peptides

Protease Inhibitors:

(a) (D)FPR (Thrombin)
Enzyme 40: 144-48, 1988
(b) (D)IEGR (Factor X)
Handbook of Synthetic Substrates for the
Coagulation and Fibronlytic Systems, H. C. Hemker,
pp. 1-175, 1983, Martinus Nijhoff
Publishers, The Hague.

Protein Kinase Substrates and Inhibitors:

(c) LRRASLG (Serine Kinase)
Biochem. Biophys. Res. Commun. 61: 559, 1974
(d) LPYA (Tyrosine Kinase)
J. Bio. Chem. 263: 5024, 1988
(e) PKI (Serine Kinase)
Science 253: 1414-20, 1991

CAAX Inhibitors:

(f) (H)-CVIM-(OH)
Proc. Natl. Acad. Sci. USA 88: 732-36, 1991
(g) (H)-CVFM-(OH)
Bioorg. Med. Chem. Letters 4: 887-92, 1994
(h) (H)-CIT-(homoserine lactone)
Science 260: 1934-37, 1993

SH2 Peptide Analogs:

(i) $^P$YZPZS$^P$YZPZS (IRS 1 analogue)
Biochemistry 33: 9376-81, 1994
(j) EPQ$^P$YEEIPIYL (Src SH$_2$ binding motif)
Cell 72: 767-68, 1993

Class MHC I Peptides:

(k) TYQRTRALV (Influenza nucleoprotein)
J. Exp. Med. 175: 481-87, 1991
(l) RGYVYQGL (VSV)
Ann. Rev. Imm. 11: 211-44, 1993

$^P$Y = phosphorylated Y
Z = norleucine

In view of the above biologically active peptides, β-sheet mimetics of this invention may be substituted for one or more amino acids thereof. For example, the following β-sheet modified peptides may be synthesized:

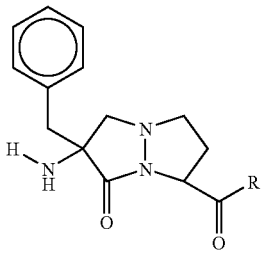
(a')

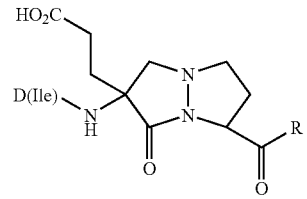
(b')

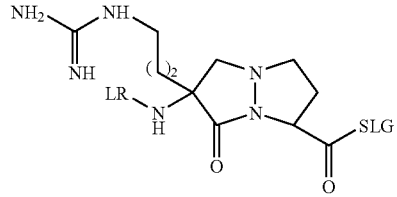
(c')

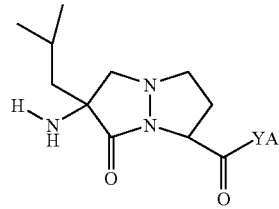
(d')

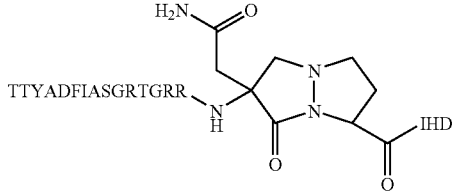
(e')

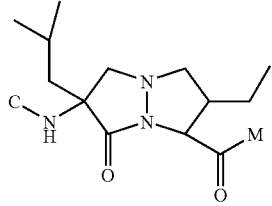
(f')

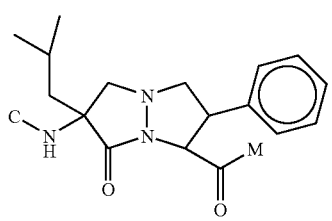
(g')

-continued

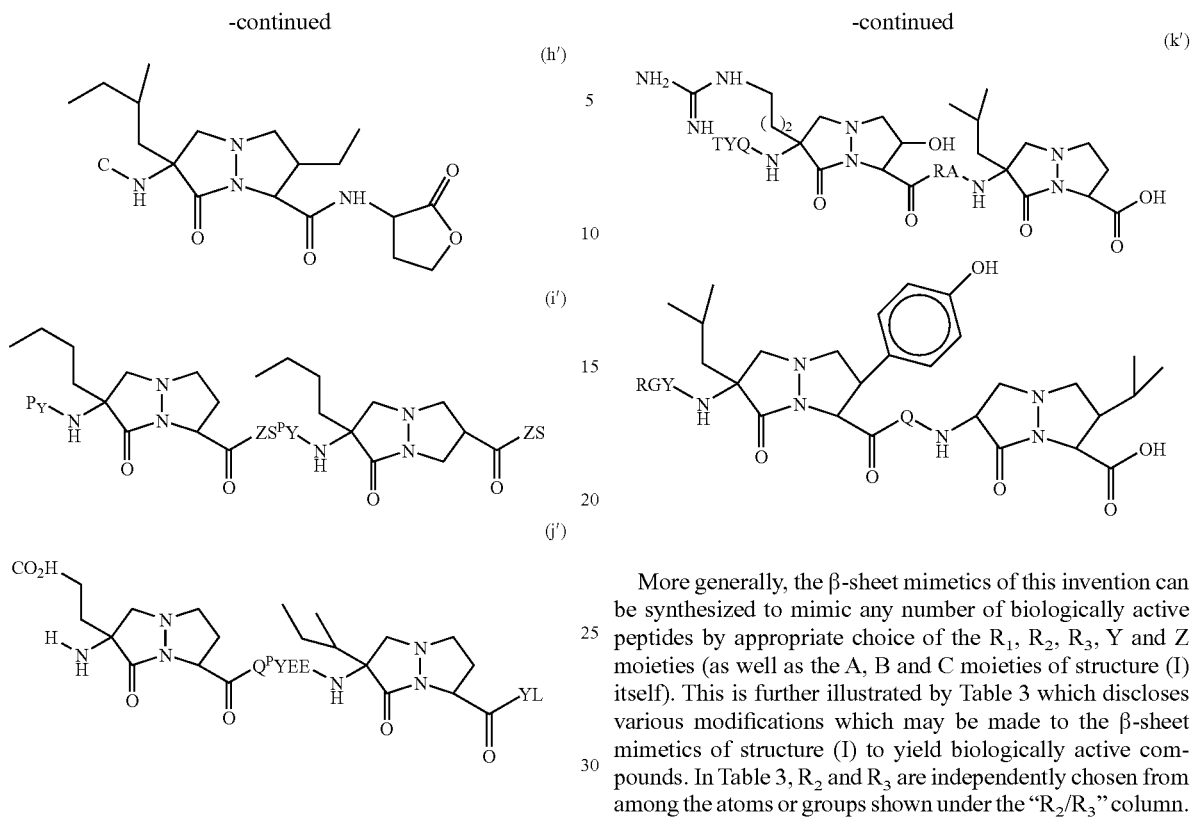

More generally, the β-sheet mimetics of this invention can be synthesized to mimic any number of biologically active peptides by appropriate choice of the $R_1$, $R_2$, $R_3$, Y and Z moieties (as well as the A, B and C moieties of structure (I) itself). This is further illustrated by Table 3 which discloses various modifications which may be made to the β-sheet mimetics of structure (I) to yield biologically active compounds. In Table 3, $R_2$ and $R_3$ are independently chosen from among the atoms or groups shown under the "$R_2/R_3$" column.

TABLE 3

Modifications to Structure (I) to Yield Biological Active Compounds

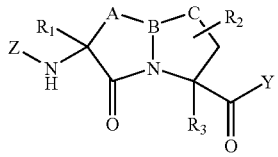

(I)

| | $R_1$ | $R_2/R_3$ | Y | Z |
|---|---|---|---|---|
| I. PROTEASE INHIBITORS | | | | |
| A. Serine | | | | |
| 1. Thrombin | $C_6$-$C_{10}$ aromatic (e.g., phenyl, benzyl, naphthyl), $C_1$-$C_{10}$ aliphatic or cycloaliphatic, substituted $C_6$-$C_{10}$ aromatic, —SiR$_3$, —CO$_2$H, —CO$_2$R | hydrogen | [structures] | hydrogen, alkyl, aryl, [structures] R = aliphatic |

TABLE 3-continued

Modifications to Structure (I) to Yield
Biological Active Compounds $$\text{Structure (I)}$$

(I)

| R₁ | R₂/R₃ | Y | Z |
|----|-------|---|---|

Y structures (column):

- propyl-NH-pyridin-2-yl
- methyl-NH-C(=O)-NH-C(=NH)-NH₂
-

R
  |
  X—⟨imidazole⟩—NH₂
  X = CH₂, NH, S, O
  R = H, CH₃

- dihydropyrimidine-2,4-dione with N-C(=NH)NH₂ substituent and methyl group
- vinyl-imidazol-2-amine with R substituent
- ethynyl-imidazol-2-amine with R substituent
- cyclopenta-fused imidazol-2-amine, (CH₂)₁,₂, methyl substituted ◉ = CH₂Cl
   CF₃

- CH₃-C(=O)-NH-cycloaliphatic

TABLE 3-continued
Modifications to Structure (I) to Yield Biological Active Compounds
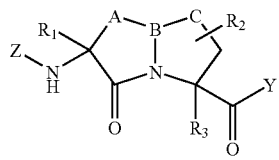
(I)
| $R_1$ | $R_2/R_3$ | Y | Z |
|---|---|---|---|
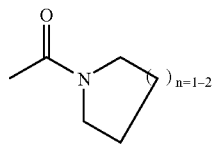
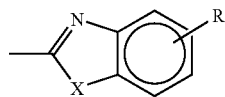
X = O, S, NH
R = $CO_2H$, $CO_2R$,
   $SO_2R$, $COCF_3$
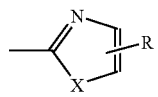
X = O, S, NH
R = $CO_2H$, $SO_2R$,
   $CO_2R$
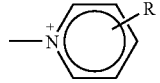
R = $CO_2H$, $CO_2$
   $SO_2R$, $COCF_3$
| 2. Elastase | $C_1$-$C_{10}$ aliphatic | hydrogen or $C_1$-$C_{10}$ heterocyclic | 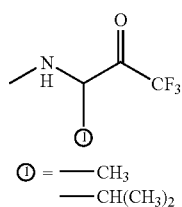 | acyl |
$⊙$ = —$CH_3$
    —$CH(CH_3)_2$
or
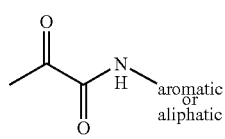
aromatic or aliphatic TABLE 3-continued
Modifications to Structure (I) to Yield Biological Active Compounds
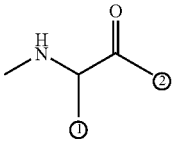
(I)
| | $R_1$ | $R_2/R_3$ | Y | Z |
|---|---|---|---|---|
| 3. Factor X | $C_1$-$C_{10}$ aliphatic carboxylic<br><br>aromatic carboxylate<br><br>$C_1$-$C_{10}$ acidic heterocyclic | hydrogen | 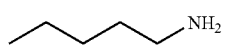 | D(Ile)<br>Acyl<br>Dansyl |
① = 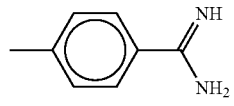
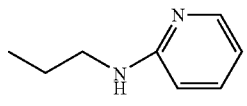
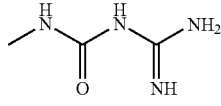
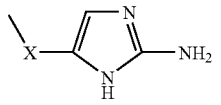
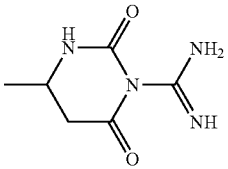
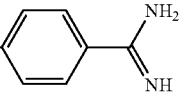
X = $CH_2$, NH
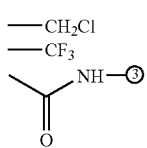
② = —$CH_2Cl$
—$CF_3$
—$\underset{O}{\underset{\|}{C}}-NH-③$ TABLE 3-continued
Modifications to Structure (I) to Yield Biological Active Compounds
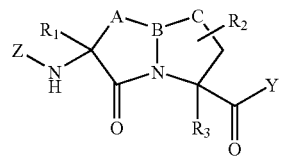
(I)
| $R_1$ | $R_2/R_3$ | Y | Z |
|---|---|---|---|
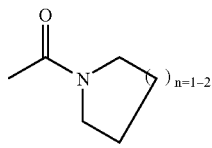
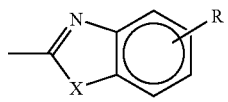
X = O, S, NH
R = $CO_2H$, $CO_2R$,
    $SO_2R$, $COCF_3$
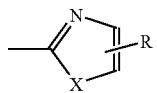
X = O, S, NH
R = $CO_2H$, $SO_2R$,
    $CO_2R$
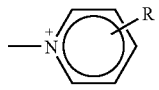
R = $CO_2H$, $CO_2$
    $SO_2R$, $COCF_3$
③ = aliphatic
    cycloaliphatic
    peptide
B. Aspartic
| | | | | |
|---|---|---|---|---|
| 1. HIV1 | $C_1$-$C_{10}$ aliphatic or arginine | $C_1$-$C_{10}$ aliphatic or 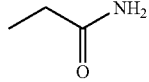 | 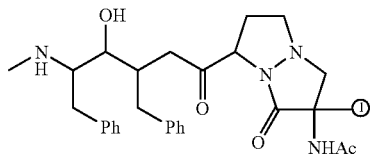<br>① = $C_1$–$C_{10}$ aliphatic arginine | acyl |
or TABLE 3-continued Modifications to Structure (I) to Yield Biological Active Compounds (I)

[Structure (I) showing a bicyclic compound with substituents $R_1$, $R_2$, $R_3$, A, B, C, N, Y, Z, NH, and two C=O groups]

| | $R_1$ | $R_2/R_3$ | Y | Z |
|---|---|---|---|---|

[Y structure: chain with NH—①, OH, O, NH—②]

① = $C_1$–$C_{10}$ aliphatic
    $C_1$–$C_{10}$ aromatic

② = amino acid
    $C_1$–$C_{10}$ alkyl
    $C_1$–$C_{10}$ aryl
    acyl
    hydrogen C. Cysteine 1. Cathepsin B | $C_6$-$C_{10}$ aromatic | $C_1$-$C_{10}$ basic | [structure with NH, C=O, ①, guanidino group $H_2N$-C(=NH)-NH] | benzyl
 | $C_1$-$C_{10}$ aliphatic | aromatic | | acyl
 | hydrogen | hydrophobic | |

① =
—CH$_2$O-C(=O)-Ar
—CH$_2$OAc
—CH$_2$N$_2^+$
—H

[epoxide structure with O, C=O, CH$_2$—NH—②]

② = $C_1$–$C_{10}$ aliphatic

2. Calpain | $C_6$-$C_{10}$ aromatic, | $C_1$-$C_{10}$ | [structure with NH, C=O, ①, ②] | benzyl
 | $C_1$-$C_{10}$ aliphatic, | aliphatic | | acyl
 | hydrophobic | | |

① = $C_1$–$C_{10}$ aromatic,
    hydrophobic

② = —CH$_2$F
    —CH$_2$N$_2$
    —CH$_2$OAc
    —H

TABLE 3-continued

Modifications to Structure (I) to Yield
Biological Active Compounds

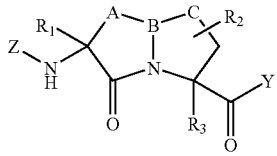

(I)

| | $R_1$ | $R_2/R_3$ | Y | Z |
|---|---|---|---|---|
| 3. ICE | $C_1$-$C_{10}$ aliphatic | hydrogen | 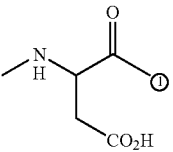 | dihydro-cinnamic, aromatic, aliphatic, acetyl |
| D. Metallo | | | | |
| 1. ACE | $C_1$-$C_{10}$ aliphatic | indoyl $C_1$-$C_{10}$ aromatic | —OH | 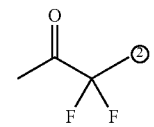 |
| 2. Collagenase | $C_1$-$C_{10}$ alkyl hydrogen | $C_1$-$C_{10}$ aromatic, $C_1$-$C_{10}$ aliphatic, $C_1$-$C_{10}$ basic | 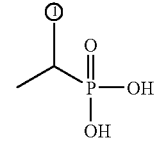 ① = alkyl | hydroxyl  ① = hydrogen $C_1$-$C_{10}$ alkyl |
| or | | | | 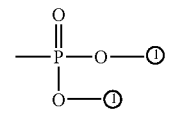 |
| | $C_6$-$C_{10}$ aromatic | $C_1$-$C_{10}$ alkyl $C_1$-$C_{10}$ aliphatic | —NHOH | hydroxyl |

TABLE 3-continued

Modifications to Structure (I) to Yield Biological Active Compounds (I)

| | $R_1$ | $R_2/R_3$ | Y | Z |
|---|---|---|---|---|
| | | | | ![phosphate]  ① = hydrogen, $C_1$–$C_{10}$ alkyl |
| | | | | ethyl phosphonic acid |
| II. KINASE INHIBITORS | | | | |
| A. Serine/Threonine | amino acid side chain | amino acid side chain | Serine, Threonine | amino acid |
| B. Tyrosine | amino acid side chain | amino acid side chain | Tyrosine | amino acid |
| C. Histidine | amino acid side chain | amino acid side chain | Histidine | amino acid |
| III. MHC II INHIBITORS | | | | |
| A. Class I | | | | |
| 1. HIV gp120 | hydrogen | hydrogen | [peptide structure with OH, NH₂] | [peptide structure with OH] |
| B. Class II | | | | |
| 1. HA (306-18) | hydrogen | | [butyl-NH₂]-YVKQNTLKLAT | hydrogen |
| 2. HSP 65 (3-13) | Cl—hydrophobic | hydrogen | -YDEEARR | -TK |

When the β-sheet mimetics of this invention are substituted for one or more amino acids of a biologically active peptide, the structure of the resulting β-sheet modified peptide (prior to cleavage from the solid support, such as PAM) may be represented by the following diagram, where $AA_1$ through $AA_3$ represent the same or different amino acids:

The precise β-sheet mimetic may be chosen by any of a variety of techniques, including computer modeling, randomization techniques and/or by utilizing natural substrate selection assays. The β-sheet mimetic may also be generated by synthesizing a library of β-sheet mimetics, and screening such library members to identify active members as disclosed above.

Once the optimized β-sheet mimetic is chosen, modification may then be made to the various amino acids attached thereto. A series of β-sheet modified peptides having a variety of amino acid substitutions are then cleaved from the solid support and assayed to identify a preferred substrate. It should be understood that the generation of such substrates may involve the synthesis and screening of a number of β-sheet modified peptides, wherein each β-sheet modified peptide has a variety of amino acid substitutions in combination with a variety of different β-sheet mimetics. In addition, it should also be recognized that, following cleavage of the β-sheet modified peptide from the solid support, the Z moiety is $AA_3$ and the Y moiety is $AA_2$ and $AA_1$ in the above diagram. (While this diagram is presented for illustration, additional or fewer amino acids may be linked to the β-sheet mimetic— that is, $AA_3$ may be absent or additional amino acids my be joined thereto; and $AA_2$ and/or $AA_1$ may be omitted or additional amino acids may be joined thereto).

Once a preferred substrate is identified by the procedures disclosed above, the substrate may be readily converted to an inhibitor by known techniques. For example, the C-terminal amino acid (in this case $AA_1$) may be modified by addition of a number of moieties known to impart inhibitor activity to a substrate, including (but not limited to) —$CF_3$ (a known reversible serine protease inhibitor), —$CH_2Cl$ (a known irreversible serine protease inhibitor), —$CH_2N_2^+$ and —$CH_2S(CH_3)_2^+$ (known cysteinyl protease inhibitors), —NHOH (a known metalloprotease inhibitor),

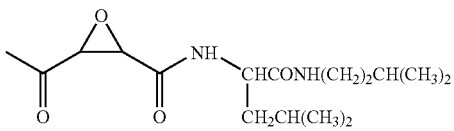

(a known cysteinyl protease inhibitor), and

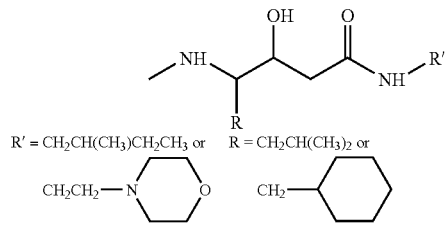

(a known aspartyl protease inhibitor).

While the utility of the β-sheet mimetics of this invention have been disclosed with regard to certain embodiments, it will be understood that a wide variety and type of compounds can be made which includes the β-sheet mimetics of the present invention. For example, a β-sheet mimetic of this invention may be substituted for two or more amino acids of a peptide or protein. In addition to improving and/or modifying the β-sheet structure of a peptide or protein, especially with regard to conformational stability, the β-sheet mimetics of this invention also serve to inhibit proteolytic breakdown. This results in the added advantage of peptides or proteins which are less prone to proteolytic breakdown due to incorporation of the β-sheet mimetics of this invention.

In another aspect, the present invention encompasses pharmaceutical compositions prepared for storage or administration which comprise a therapeutically effective amount of a β-sheet mimetic or compound of the present invention in a pharmaceutically acceptable carrier. Anticoagulant therapy is indicated for the treatment and prevention of a variety of thrombotic conditions, particularly coronary artery and cerebrovascular disease. Those experienced in this field are readily aware of the circumstances requiring anticoagulant therapy.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted hose skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited (e.g., when contacting the mammal's blood with material selected from the group consisting of vascular grafts, stems, orthopedic prosthesis, cardiac prosthesis, and extracorporeal circulation systems).

The thrombin inhibitors can be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent or treating ocular build up of fibrin. The compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydibydropyrans, polycyanoacrylates and cross linked or amphipathic block copolymers of hydrogels.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

Tablets suitable for oral administration of active compounds of the invention, e.g., structures (47), (20b), (37), (39) (29a), (35), (45), (51), (29b), (41) and (13b), can be prepared as follows:

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

An intravenous dosage form of the above-indicated active compounds may be prepared as follows:

| Active Compound | 0.5-10.0 mg |
| --- | --- |
| Sodium Citrate | 5-50 mg |
| Citric Acid | 1-15 mg |
| Sodium Chloride | 1-8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopoeia/National Formulary for 1995, published by United States Pharmacopoeia Convention, Inc., Rockville, Md., copyright 1994).

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts (Kasten, B. L., "Specimen Collection," *Laboratory Test Handbook,* 2nd Edition, Lexi-Comp Inc., Cleveland pp. 16-17, Edits. Jacobs, D. S. et al. 1990). Such vacuum tubes may be free of clot-inhibiting additives, in which case, they are useful for the isolation of mammalian serum from the blood they may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The following examples are offered by way of illustration, not limitation.

EXAMPLES

Example 1

Synthesis of Representative β-Sheet Mimetic

This example illustrates the synthesis of a representative β-sheet mimetic of this invention.

Synthesis of Structure (1)

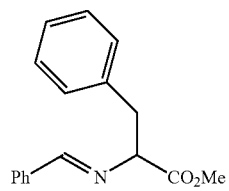

(1)

Phenylalanine benzaldimine, structure (1), was synthesized as follows. To a mixture of L-phenylalanine methyl ester hydrochloride (7.19 g, 33.3 mmol) and benzaldehyde (3.4 ml, 33.5 mmol) stirred in $CH_2Cl_2$ (150 ml) at room temperature was added triethylamine (7.0 ml, 50 mmol). Anhydrous magnesium sulfate (2 g) was added to the resulting solution and the mixture was stirred for 14 h then filtered through a 1 inch pad of Celite with $CH_2Cl_2$. The filtrate was concentrated under reduced pressure to ca. one half of its initial volume then diluted with an equal volume of hexanes. The mixture was extracted twice with saturated aqueous $NaHCO_3$, $H_2O$ and brine then dried over anhydrous $Na_2SO_4$ and filtered. Concentration of the filtrate under vacuum yielded 8.32 g (93% yield) of colorless oil. $^1$H NMR analysis indicated nearly pure (>95%) phenylalanine benzaldimine. The crude product was used without further purification.

Synthesis of Structure (2)

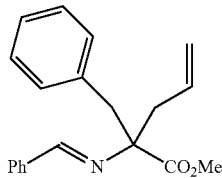

(2)

α-Allylphenylalanine benzaldimine, structure (2), was synthesized as follows. To a solution of diisopropylamine (4.3 ml, 33 mmol) stirred in THF (150 ml) at −78° C. was added dropwise a solution of n-butyllithium (13 ml of a 2.5 M hexane solution, 33 mmol). The resulting solution was stirred for 20 min. then a solution of phenylalanine benzaldimine (7.97 g, 29.8 mmol) in THF (30 ml) was slowly added. The resulting dark red-orange solution was stirred for 15 min. then allyl bromide (3.1 ml, 36 mmol) was added. The pale yellow solution was stirred for 30 min. at −78° C. then allowed to warm to room temperature and stirred an additional 1 h. Saturated aqueous ammonium chloride was added and the mixture was poured into ethyl acetate. The organic phase was separated and washed with water and brine then dried over anhydrous sodium sulfate and filtered. Concentration of the filtrate under vacuum yielded 8.54 g of a viscous yellow oil. Purification by column chromatography yielded 7.93 g (87%) of α-allylphenylalanine benzaldimine as a viscous colorless oil.

Synthesis of Structure (3)

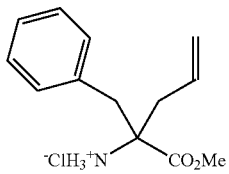

(3)

α-Allylphenylalanine hydrochloride, structure (3), was synthesized as follows. To a solution of α-allylphenylalanine benzaldimine (5.94 g, 19.3 mmol) stirred in methanol (50 ml) was added 5% aqueous hydrochloric acid (10 ml). The solution was stirred at room temperature for 2 h then concentrated under vacuum to an orange-brown caramel. The crude product was dissolved in $CHCl_3$ (10 ml) and the solution was heated to boiling. Hexanes (~150 ml) were added and the slightly cloudy mixture was allowed to cool. The liquid was decanted away from the crystallized solid then the solid was rinsed with hexanes and collected. Removal of residual solvents under vacuum yielded 3.56 g (72%) of pure α-allylphenylalanine hydrochloride as a white crystalline solid.

$^1$H NMR (500 MHz, $CDCl_3$) δ 8.86 (3H, br s), 7.32-7.26 (5H, m), 6.06 (1H, dddd, J=17.5, 10.5, 7.6, 7.3 Hz), 5.33 (1H, d, J=17.5 Hz), 5.30 (1H, d, J=10.5 Hz), 3.70 (3H, s), 3.41 (1H, d, J=14.1 Hz), 3.35 (1H, d, J=14.1 Hz), 2.98 (1H, dd, J=14.5, 7.3 Hz), 2.88 (1H, dd, J=14.5, 7.6 Hz).

Synthesis of Structure (4)

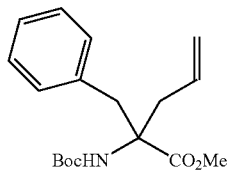

(4)

N-tert-butyloxycarbonyl-α-allylphenylalanine, structure (4) was synthesized as follows. To a solution of D,L α-allylphenylalanine hydrochloride (565 mg, 2.21 mmol) stirred in a mixture of THF (15 ml) and water (5 ml) was added di-tert-butyl dicarbonate followed by careful addition of solid sodium bicarbonate in small portions. The resulting two phase mixture was vigorously stirred at room temperature for 2 days then diluted with ethyl acetate. The organic phase was separated and washed with water and brine then dried over anhydrous sodium sulfate and filtered. Concentration of the filtrate under vacuum yielded a colorless oil that was purified by column chromatography (5 to 10% EtOAc in hexanes gradient elution) to yield 596 mg (86%) of N-tert-butyloxycarbonyl-α-allylphenylalanine.

TLC $R_f$=0.70 (silica, 20% EtOAc in hexanes); $^1$H NMR (500 MHz, $CDCl_3$) δ 7.26-7.21 (3H, m), 7.05 (2H, d, J=6.1 Hz), 5.64 (1H, dddd, J=14.8, 7.6, 7.2, 7.2 Hz), 5.33 (1H, br s), 5.12-5.08 (2H, m), 3.75 (3H, s), 3.61 (1H, d, J=13.5 Hz), 3.21 (1H, dd, J=13.7, 7.2 Hz), 3.11 (1H, d, J=13.5 Hz), 2.59 (1H, dd, J=13.7, 7.6 Hz), 1.47 (9H, s).

Synthesis of Structure (5)

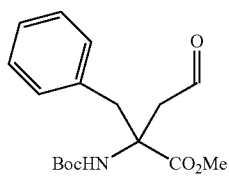

(5)

An aldehyde of structure (5) was synthesized as follows. Ozone was bubbled through a solution of 2.10 g (6.57 mmol) of the structure (4) olefin stirred at −78° C. in a mixture of $CH_2Cl_2$ (50 ml) and methanol (15 ml) until the solution was distinctly blue in color. The solution was stirred an additional 15 min. then dimethyl sulfide was slowly added. The resulting colorless solution was stirred at −78° C. for 10 min. then allowed to warm to room temperature and stirred for 6 h. The solution was concentrated under vacuum to 2.72 g of viscous pale yellow oil which was purified by column chromatography (10 to 20% EtOAc in hexanes gradient elution) to yield 1.63 g of pure aldehyde as a viscous colorless oil.

TLC $R_f$=0.3 (silica, 20% EtOAc in hexanes); $^1$H NMR (500 MHz, CDCl$_3$) δ 9.69 (1H, br s), 7.30-7.25 (3H, m), 7.02 (2H, m), 5.56 (1H, br s), 3.87 (1H, d, J=17.7 Hz), 3.75 (3H, s), 3.63 (1H, d, J=13.2 Hz), 3.08 (1H, d, J=17.7 Hz), 2.98 (1H, d, J=13.2 Hz), 1.46 (9H, s).

Synthesis of Structure (6)

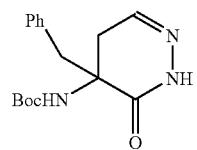

(6)

A hydrazone of structure (6) was synthesized as follows. To a solution of the aldehyde of structure (5) (1.62 g, 5.03 mmol) stirred in THF (50 ml) at room temperature was added hydrazine hydrate (0.32 ml, 6.5 mmol). The resulting solution was stirred at room temperature for 10 min. then heated to reflux for 3 days. The solution was allowed to cool to room temperature then concentrated under vacuum to 1.59 g (105% crude yield) of colorless foam. The crude hydrazone product, structure (6), was used without purification.

TLC $R_f$=0.7 (50% EtOAc in hexanes); $^1$H NMR (500 MHz, CDCl$_3$) δ 8.55 (1H, br s), 7.32-7.26 (3H, m), 7.17 (1H, br s), 7.09 (2H, m), 5.55 (1H, br s), 3.45 (1H, d, J=17.7 Hz), 3.29 (1H, d, J=13.5 Hz), 2.90 (1H, d, J=13.5 Hz), 2.88 (1H, dd, J=17.7, 1.3 Hz), 1.46 (9H, s); MS (CI+, NH$_3$) m/z 304.1 (M+H$^+$).

Synthesis of Structure (7)

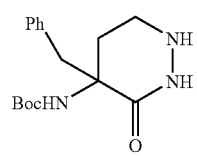

(7)

A cyclic hydrazide of structure (7) was synthesized as follows. The crude hydrazone of structure (6) (55 mg, 0.18 mmol) and platinum oxide (5 mg, 0.02 mmol) were taken up in methanol and the flask was fitted with a three-way stopcock attached to a rubber balloon. The flask was flushed with hydrogen gas three times, the balloon was inflated with hydrogen, and the mixture was stirred vigorously under a hydrogen atmosphere for 17 hours. The mixture was filtered through Celite with ethyl acetate and the filtrate was concentrated under vacuum to a white form. Purification of the white foam by flash chromatography yielded 44 mg of the pure cyclic hydrazide of structure (7) (80%).

$^1$H NMR (500 MHz, CDCl$_3$) δ 7.34-7.28 (3H, m), 7.21 (2H, m), 6.95 (1H, br s), 5.29 (1H, br s), 3.91 (1H, br s), 3.35 (1H, d, J=12.9 Hz), 3.00 (1H, ddd, J=13.9, 5.3, 5.0 Hz), 2.96 (1H, d, J=12.9 Hz), 2.67 (1H, br m), 2.38 (1H, br m), 2.30 (1H, ddd, J=13.9, 5.4, 5.0 Hz), 1.45 (9H, s); MS (CI+, NH$_3$) m/z 306.2 (M+H$^+$).

Synthesis of Structure (8)

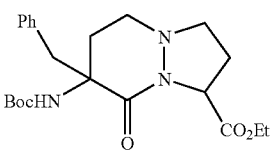

(8)

Structure (8) was synthesized as follows. To a solution of the cyclic hydrazide of structure (7) (4.07 g, 13.32 mmol) stirred in ethyl acrylate (200 ml) at 90° C. was added formaldehyde (1.2 mL of a 37% aqueous solution). The mixture was heated to reflux for 15 h then allowed to cool to room temperature and concentrated under vacuum to a white foam. The products were separated by column chromatography (5% then 10% acetone/chloroform) to yield 0.851 g of the least polar diastereomer of the bicyclic ester, structure (8b), and a more polar diastereomer (8a). The impure fractions were subjected to a second chromatography to afford more pure structure (8b), 25% combined yield.

$^1$H NMR (500 MHz, CDCl$_3$) δ 7.27-7.21 (3H, m), 7.09 (2H, d, J=6.5 Hz), 5.59 (1H, br s), 4.52 (1H, dd, J=9.1, 3.4 Hz), 4.21 (2H, m), 3.40 (1H, d, J=12.5 Hz), 3.32 (1H, d, J=12.5 Hz), 3.10 (2H, m), 2.79 (1H, br m), 2.66 (1H, br m), 2.79 (1H, br m), 2.66 (1H, br m), 2.54 (1H, br m), 2.46 (1H, m), 2.18 (1H, m), 1.44 (9H, s), 1.28 (3H, t, J=7.0 Hz); MS (CI+, NH$_3$) 418.4 (M+H$^+$).

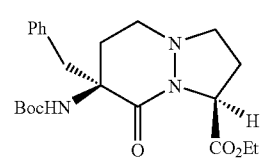

(8b)

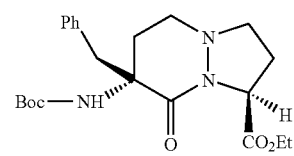

(8a)

Synthesis of Structure (9b)

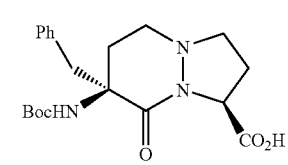

(9b)

Structure (9b) was synthesized as follows. To a solution of the least polar ethyl ester (i.e., structure (8b)) (31 mg, 0.074 mmol) stirred in THF (1 ml) was added aqueous lithium hydroxide (1 M, 0.15 ml). The resulting mixture was stirred at room temperature for 2 h then the reaction was quenched with 5% aqueous citric acid. The mixture was extracted with ethyl acetate (2×) then the combined extracts were washed with water and brine. The organic layer was dried over anhydrous sodium sulfate, filtered and concentrated under vacuum to a colorless glass. The crude acid, structure (9b), was used in subsequent experiments without further purification.

Synthesis of Structure (10b)

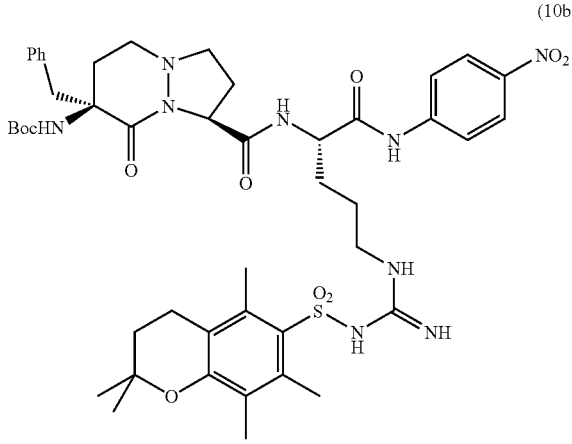

(10b)

Structure (10b) was synthesized as follows. The crude acid of structure (9b) (30 mg, 0.074 mmol), HArg(PMC)$_p$NA (41 mg, 0.074 mmol), and HOBt (15 mg, 0.098 mmol) were dissolved in THF (1 ml) then diisopropylethylamine (0.026 ml, 0.15 mmol) was added followed by EDC (16 mg, 0.084 mmol). The resulting mixture was stirred at room temperature for 4 h then diluted with ethyl acetate and extracted with 5% aqueous citric acid, saturated aqueous sodium bicarbonate, water and brine. The organic layer was dried over anhydrous sodium sulfate, filtered and concentrated under vacuum to 54 mg of pale yellow glass. The products were separated by column chromatography to yield 33 mg (50%) of a mixture of diastereomers of the coupled (i.e., protected) product, structure (10b). MS (CI+, NH$_3$) m/z 566.6 (M+H$^+$)

Synthesis of Structure (11b)

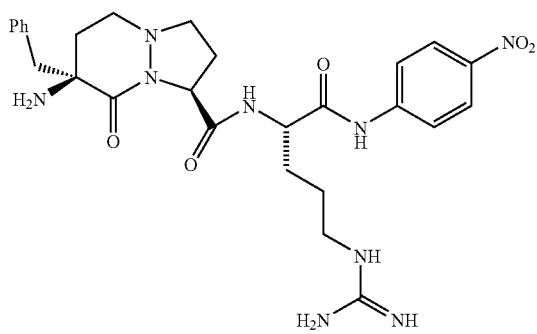

(11b)

A β-sheet mimetic of structure (11b) was synthesized as follows. A solution of 0.25 ml of H$_2$O, 0.125 ml of 1,2-ethanedithiol and 360 mg of phenol in 5 ml of TFA was prepared and the protected product of structure (10b) (33 mg, 0.035 mmol) was dissolved in 2 ml of this solution. The resulting solution was stirred at room temperature for 3 h then concentrated under reduced pressure. Ether was added to the concentrate and the resulting precipitate was collected by centrifugation. The precipitate was triturated with ether and centrifuged two more times then dried in a vacuum desiccator for 14 h. The crude product (14 mg) was purified by HPLC chromatography to yield the β-sheet mimetic of structure (11b). MS (CI+, NH$_3$) m/z 954.8 (M+Na$^+$).

Synthesis of Structure (12b)

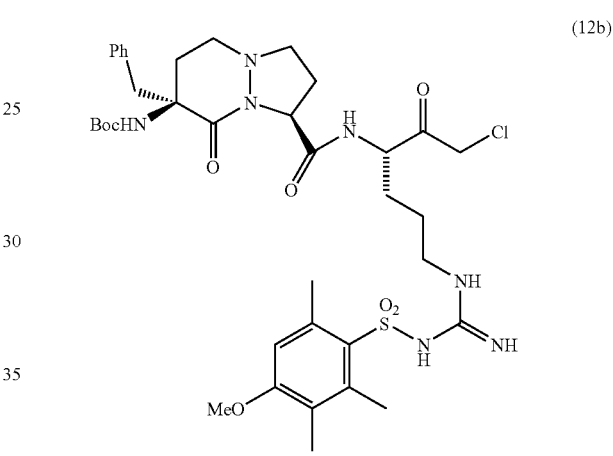

(12b)

Structure (12b) was synthesized as follows. To a solution of the crude acid of structure (9b) (24 mg, 0.062 mmol) and N-methylmorpholine (0.008 ml), stirred in THF (1 ml) at −50° C. was added isobutyl chloroformate. The resulting cloudy mixture was stirred for 10 min. then 0.016 ml (0.14 mmol) of N-methylmorpholine was added followed by a solution of HArg(Mtr)CH$_2$Cl (50 mg, 0.068 mmol) in THF (0.5 ml). The mixture was kept at −50° C. for 20 min. then was allowed to warm to room temperature during 1 h. The mixture was diluted with ethyl acetate and extracted with 5% aqueous citric acid, saturated aqueous sodium bicarbonate and brine. The organic layer was dried over anhydrous sodium sulfate, filtered and concentrated under vacuum to yield 49 mg of colorless glass, structure (12). Separation by column chromatography yielded 12 mg of a less polar diastereomer and 16 mg of a more polar diastereomer.

$^1$H NMR (500 MHz, CDCl$_3$) δ 7.93 (1H, br s), 7.39-7.31 (3H, m), 7.16 (2H, d, J=6.9 Hz), 6.52 (1H, s), 6.30 (1H, br s), 5.27 (1H, s), 4.74 (1H, dd, J=9.1, 6.9 Hz), 4.42 (1H, br d, J=6.8 Hz), 4.33 (1H, d, J=6.8 Hz), 3.82 (3H, s), 3.28 (1H, d, J=13.3 Hz), 3.26-3.12 (4H, m), 2.98 (1H, d, J=13.3 Hz), 2.69 (3H, s), 2.60 (3H, s), 2.59-2.33 (4H, m), 2.25-2.10 (3H, m), 2.11 (3H, s), 1.77 (1H, br m), 1.70-1.55 (3H, br m), 1.32 (9H, s).

Synthesis of Structure (13b)

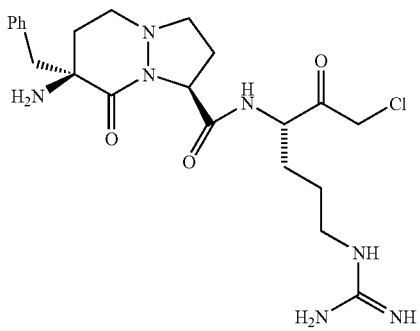

A β-sheet mimetic of structure (13b) was synthesized as follows. The more polar diastereomer of structure (12b) (16 mg, 0.021 mmol) was dissolved in 95% TFA/H$_2$O (1 ml) and the resulting solution was stirred at room temperature for 6 h then concentrated under vacuum to 11 mg of crude material. The crude product was triturated with ether and the precipitate was washed twice with ether then dried under high vacuum for 14 h. $^1$H NMR analysis indicated a 1:1 mixture of fully deprotected product and product containing the Mtr protecting group. The mixture was dissolved in 95% TFA/H$_2$O and stirred for 2 days and the product was recovered as above. Purification of the product by HPLC yielded 5 mg of the pure compound of structure (13b). MS (EI+) m/z 477.9 (M$^+$).

Example 2

Synthesis of Representative β-Sheet Mimetic

This example illustrates the synthesis of a further representative β-sheet mimetic of this invention.

Synthesis of Structure (14)

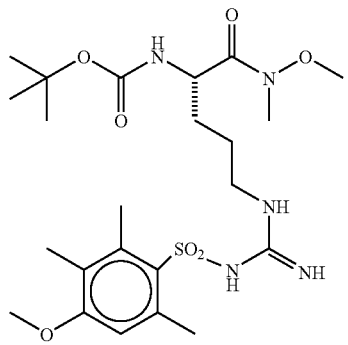

N,O-Dimethyl hydroxamate, structure (14), was synthesized as follows. To a mixture of Boc-N$^g$-4-methoxy-2,3,6-trimethylbenzenesulfonyl-L-arginine (8.26 g, 14.38 mmol), N,O-dimethylhydroxylamine hydrochloride (2.78 g, 28.5 mmol) and 1-hydroxybenzotriazole hydrate (2.45 g, 16.0 mmol) stirred in THF (150 ml) at ambient temperature was added N,N-diisopropylethylamine (7.5 ml, 43 mmol) followed by solid EDC (3.01 g, 15.7 mmol). The resulting solution was stirred for 16 h then diluted with ethyl acetate (200 ml) and extracted sequentially with 5% aqueous citric acid, saturated aqueous sodium bicarbonate, water and brine. The organic solution was dried over anhydrous sodium sulfate and filtered. Concentration of the filtrate under vacuum yielded 7.412 g of white foam.

$^1$H NMR (500 Mhz, CDCl$_3$): δ 6.52 (1H, s), 6.17 (1H, br s), 5.49 (1H, d, J=8.8 Hz), 4.64 (1H, br t), 3.82 (3H, s), 3.72 (3H, s), 3.36 (1H, br m), 3.18 (3H, s), 3.17 (1H, br m), 2.69 (3H, s), 2.61 (3H, s), 2.12 (3H, 2), 1.85-1.55 (5H, m), 1.41 (9H, s); MS (FB+): m/z 530.5 (M+H$^+$).

Synthesis of Structure (15)

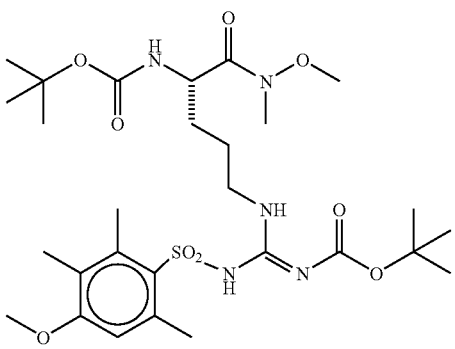

Structure (15) was synthesized as follows. To a solution of the arginine amide (7.412 g, 13.99 mmol) stirred in dichloromethane (150 ml) at room temperature was added N,N-diisopropylethylamine (2.9 ml, 17 mmol) followed by di-tert-butyldicarbonate (3.5 ml, 15.4 mmol) and N,N-dimethylaminopyridine (0.175 g, 1.43 mmol). The resulting solution was stirred for 1.5 h then poured into water. The aqueous layer was separated and extracted with two 100 ml portions of dichloromethane. The combine extracts were shaken with brine then dried over anhydrous sodium sulfate and filtered. Concentration of the filtrate under vacuum yielded a white foam that was purified by flash chromatography to yield 8.372 g of white foam.

$^1$H NMR (500 MHz, CDCl$_3$): δ 9.79 (1H, s), 8.30 (1H, t, J=4.96), 6.54 (1H, s), 5.18 (1H, d, J=9.16 Hz), 4.64 (1H, m), 3.83 (3H, s), 3.74 (3H, s), 3.28 (2H, dd, J=12.6, 6.9 Hz), 3.18 (3H, s), 2.70 (3H, s), 2.62 (3H, s), 2.14 (3H, s), 1.73-1.50 (5H, m), 1.48 (9H, s), 1.42 (9H, s); MS (FB+): m/z 630.6 (M+H$^+$).

Synthesis of Structure (16)

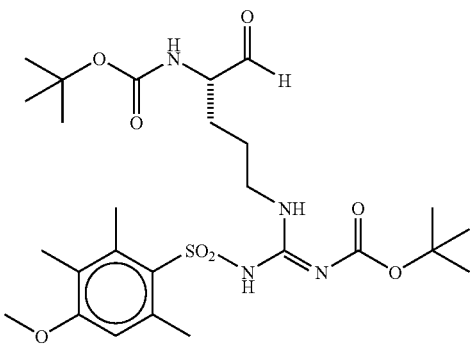

(16)

The arginal, structure (16), was synthesized as follows. To a solution of the arginine amide structure (15) stirred in toluene at −78° C. under a dry argon atmosphere was added a solution of diisobutylaluminum hydride in toluene (1.0 M, 7.3 ml) dropwise over a period of 15 minutes. The resulting solution was stirred for 30 minutes then a second portion of diisobutylaluminum hydride (3.5 ml) was added and stirring was continued for 15 minutes. Methanol (3 ml) was added dropwise and the solution was stirred at −78° C. for 10 minutes then allowed to warm to room temperature. The mixture was diluted with ethyl acetate (100 ml) and stirred vigorously with 50 ml of saturated aqueous potassium sodium tartrate for 2.5 h. The aqueous phase was separated and extracted with ethyl acetate (2×100 ml). The extracts were combined with the original organic solution and shaken with brine then dried over anhydrous sodium sulfate and filtered. Concentration of the filtrate under vacuum yielded a white foam that was separated by flash chromatography to yield 1.617 g of the aldehyde as a white foam.

$^1$H NMR (500 MHz, CDCl$_3$): δ 9.82 (1H, s), 9.47 (1H, s), 8.35 (1H, br t), 6.55 (1H, s), 5.07 (1H, d, J=6.9 Hz), 4.18 (1H, br m), 3.84 (3H, s), 3.25 (2H, m), 2.70 (3H, s), 2.62 (3H, s), 2.14 (3H, s), 1.89 (1H, m), 1.63-1.55 (4H, m), 1.49 (9H, s), 1.44 (9H, s); MS (FB+): m/z 571.6 (M+H$^+$).

Synthesis of Structure (17)

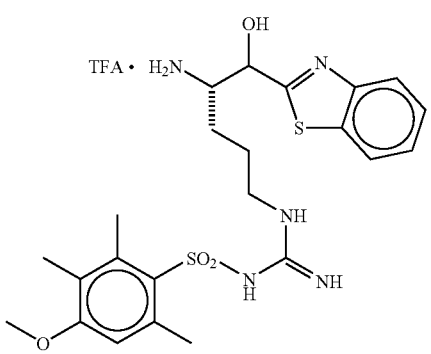

(17)

Hydroxybenzothiazole, structure (17), was synthesized as follows. To a solution of benzothiazole (1.55 ml, 14 mmol) stirred in anhydrous diethyl ether (60 ml) at −78° C. under a dry argon atmosphere was added a solution of n-butyllithium (2.5 M in hexane, 5.6 ml, 14 mmol) dropwise over a period of 10 minutes. The resulting orange solution was stirred for 45 minutes then a solution of the arginal structure (16) (1.609 g, 2.819 mmol) in diethyl ether (5 ml) was slowly added. The solution was stirred for 1.5 h then saturated aqueous ammonium chloride solution was added and the mixture was allowed to warm to room temperature. The mixture was extracted with ethyl acetate (3×100 ml) and the combined extracts were extracted with water and brine then dried over anhydrous sodium sulfate and filtered. Concentration of the filtrate under vacuum yielded a yellow oil that was purified by flash chromatography (30% then 40% ethyl acetate/hexanes eluent) to yield 1.22 g of the hydroxybenzothiazoles (ca. 2:1 mixture of diastereomers) as a white foam.

The mixture of hydroxybenzothiazoles (1.003 g, 1.414 mmol) was stirred in CH$_2$Cl$_2$ (12 ml) at room temperature and trifluoroacetic acid (3 ml) was added. The resulting solution was stirred for 1.5 h then concentrated under reduced pressure to yield 1.22 g of the benzothiazolylarginol trifluoroacetic acid salt as a yellow foam.

MS (EI+): m/z 506.2 (M+H$^+$).

Synthesis of Structure (18b)

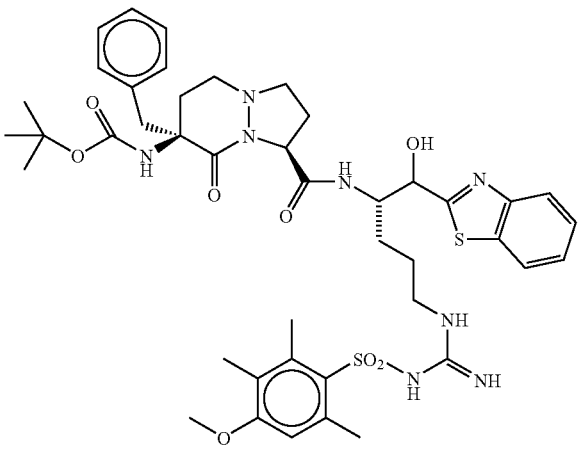

(18b)

The bicyclic compound, structure (18b) was synthesized as follows. The bicyclic acid of structure (9b) from Example 1 (151 mg, 0.387 mmol) and HOBt hydrate (71 mg, 0.46 mmol) were dissolved in THF (5 ml) and diisopropylethylamine (0.34 ml, 1.9 mmol) was added followed by EDC (89 mg, 0.46 mmol). After stirring for ten minutes a solution of the benzothiazolylarginol trifluoroacetic acid salt (structure (17) 273 mg, 0.372 mmol) in THF (1 ml) was added along with a THF (0.5 ml) rinse. The mixture was stirred at room temperature for 15 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 297 mg of a yellow glass. $^1$H NMR analysis indicated a mixture of four diastereomeric amides which included structure (18b)

MS (ES+): m/z 877 (M$^+$). .

Synthesis of Structure (19b)

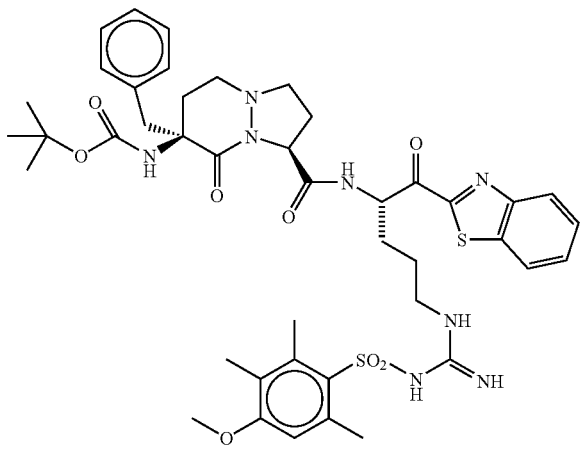

(19b)

Structure (19b) was synthesized as follows. The crude hydroxybenzothiazole (247 mg, 0.282 mmol) was dissolved in $CH_2Cl_2$ (5 ml) and Dess-Martin periodinane (241 mg, 0.588 mmol) was added. The mixture was stirred at room temperature for 6 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 252 mg of yellow glass. $^1H$ NMR analysis indicated a mixture of two diastereomeric ketobenzothiazoles which included structure (19b).

Synthesis of Structure (20b)

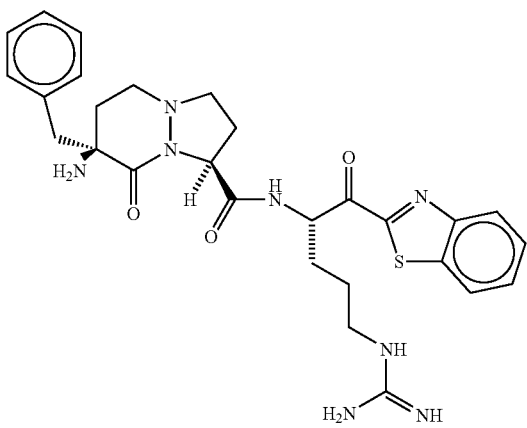

(20b)

The ketobenzothiazole, structure (20), was synthesized as follows. Ketobenzothiazole (19) (41 mg, 0.047 mmol) was dissolved in 95% aqueous trifluoroacetic (0.95 ml) acid and thioanisole (0.05 ml) was added. The resulting dark solution was stirred for 30 hours at room temperature then concentrated under vacuum to a dark brown gum. The gum was triturated with diethyl ether and centrifuged. The solution was removed and the solid remaining was triturated and collected as above two more times. The yellow solid was dried in a vacuum desiccator for 2 hours then purified by HPLC (Vydac reverse phase C-4 column (22×250 mm ID). Mobile phase: A=0.05% TFA in water; B=0.05% TFA in acetonitrile. The flow rate was 10.0 mL/min. The gradient used was 8% B to 22% B over 25 min, and isochratic at 22% thereafter. The peak of interest (structure (20b)) eluted at 42 minutes) to give 2.5 mg of the deprotected product, structure (20b).

MS (ES+): 563.5 ($M+H^+$).

Example 3

Activity of a Representative β-Sheet Mimetic as a Proteolytic Substrate

This example illustrates the ability of a representative β-sheet mimetic of this invention to selectively serve as a substrate for thrombin and Factor VII. The β-sheet mimetic of structure (11b) above was synthesized according the procedures disclosed in Example 1, and used in this experiment without further modification.

Both the thrombin and Factor VII assays of this experiment were carried out at 37° C. using a Hitachi UV/Vis spectrophotometer (model U-3000). Structure (11b) was dissolved in deionized water. The concentration was determined from the absorbance at 342 nm. Extinction coefficient of 8270 liters/mol/cm was employed. The rate of structure (11b) hydrolysis was determined from the change in absorbance at 405 nm using an extinction coefficient for p-nitroaniline of 9920 liters/mol/cm for reaction buffers. Initial velocities were calculated from the initial linear portion of the reaction progress curve. Kinetic parameters were determined by unweighted nonlinear least-squares fitting of the simple Michaelis-Menten equation to the experimental data using GraFit (Version 3.0, Erithacus Software Limited).

For the thrombin assay, experiments were performed in pH 8.4 Tris buffer (Tris, 0.05M; NaCl, 0.15M). 6.4 NIH units of bovine thrombin (from Sigma) were dissolved into 10 ml of the assay buffer to yield 10 nM thrombin solution. In a UV cuvette, 130 to 148 μl of the buffer and 100 μl of the thrombin solutions were added, preincubated at 37° C. for 2 minutes, and finally 2 to 20 microliters (to make the final volume at 250 μl) of 0.24 mM structure (11b) solution was added to initiate the reaction. The first two minutes of the reactions were recorded for initial velocity determination. Eight structure (11b) concentration points were collected to obtain the kinetic parameters. $k_{cat}$ and $K_M$ were calculated to be 50 $s^{-1}$ and 3 μM, respectively. $k_{cat}/K_M$ was found to be $1.67 \times 10^7$ $M^{-1} s^{-1}$.

For the Factor VII assay, pH 8.0 Tris buffer (0.05 M Tris, 5 mM $CaCl_2$, 0.15 M NaCl, 0.1% TWEEN 20, 0.1% BSA) was used. 10 μl of 20 μM human Factor VIIa (FVIIa) and 22 μM of human tissue factor (TF) was brought to assay buffer to make 160 nM FVIIa and TF solutions, respectively. 40 to 48 μl of buffer, 25 μl of FVIIa and 25 μl TF solution were added to a cuvette, and incubated at 37° C. for 5 minutes, then 2 to 10 μl of 2.4 mM structure (11b) solution was added to the cuvette to initiate reaction (final volume was 100 ml). The initial 3 minutes reaction progress curves were recorded. Five structure (11b) concentration points were collected. The initial rates were linear least-square fitted against the concentrations of structure (11b) with GraFit. The $k_{cat}/K_M$ was calculated from the slope and found to be 17,500 $M^{-1} s^{-1}$.

In both the thrombin and Factor VII assay of this experiment, (D)FPR—PNA was run as a control. Activity of structure (11b) compared to the control was 0.76 and 1.38 for thrombin and Factor VII, respectively (Factor VII: $K_{cat}/K_M$=1.27×10$^4$ M$^{-1}$ s$^{-1}$; thrombin: $K_{cat}/K_M$=2.20×10$^7$ M$^{-1}$ s$^{-1}$).

Example 4

Activity of a Representative β-Sheet Mimetic as a Protease Inhibitor

This example illustrates the ability of a representative β-sheet mimetic of this invention to function as a protease inhibitor for thrombin, Factor VII, Factor X, urokinase, tissue plasminogen activator (t-PA), protein C, plasmin and trypsin. The β-sheet mimetic of structure (13b) above was synthesized according to the procedures disclosed in Example 1, and used in this experiment.

All inhibition assays of this experiment were performed at room temperature in 96 well microplates using a Bio-Rad microplate reader (Model 3550). 0.29 mg of structure (13b) was dissolved into 200 ml of 0.02 N hydrochloric acid deionized water solution. This solution (2.05 mM) served as the stock solution for all the inhibition assays. The hydrolysis of chromogenic substrates was monitored at 405 nm. The reaction progress curves were recorded by reading the plates typically 90 times with 30 seconds to 2 minute intervals. The initial rate were determined by unweighted nonlinear least-squares fitting to a first order reaction in GraFit. The determined initial velocities were then nonlinear least-square fitted against the concentrations of structure (13b) using GraFit to obtain $IC_{50}$. Typically, eight structure (13b) concentration points were employed for $IC_{50}$ determination.

For the thrombin assay, N-p-tosyl-Gly-Pro-Arg-pNA (from Sigma) was used at 0.5 mM concentration in 1% DMSO (v/v) pH 8.4 Tris buffer as substrate. From structure (13b) stock solution two steps of dilution were made. First, 1:2000 dilution into 0.02 N hydrochloride solution, then 1:100 dilution into pH 8.4 Tris buffer. The final dilution of structure (13b) served as the first point (10 nM). Seven sequential dilutions were made from the first point with a dilution factor of 2. Into each reaction well, 100 μl of 10 nM thrombin solution and 50 μl of structure (13b) solution were added. The mixture of the enzyme and inhibitor was incubated for 20 minutes, then 100 μl of 0.5 mM substrate solution was added to initiate the reaction. The $IC_{50}$ of structure (13b) against thrombin was found to be 1.2±0.2 nM.

In the Factor VII assay, S-2288 (from Pharmacia), D-Ile-Pro-Arg-pNA was used at 20 μM in deionized water as substrate. From the stock of structure (13b), a 1:100 dilution was made into pH 8.0 Tris buffer. This dilution served as the first point of the inhibitor (20 μM). From this concentration point 6 more sequential dilutions were made with a dilution factor of 2. 50 μl of 16 nM FVIIa and TF complex solution and 40 μl of the inhibitor solutions were added into each well, the mixtures were incubated for 20 minutes before 10 μl of 20 mM S-2288 was added. $IC_{50}$ of structure (13b) against factor VII was found to be 140±3 nM.

In the Factor X assay, buffer and substrate are the same as used for thrombin assay. A 1:100 dilution was made into pH 8.4 Tris buffer to serve as the first point. Seven dilutions with a dilution factor of 2 were made. The assay protocol is the same as for thrombin except 25 nM of bovine factor Xa (from Sigma) in pH 8.4 Tris buffer was used instead of thrombin. $IC_{50}$ of structure (13b) against factor X was found to be 385±17 nM.

In the urokinase assay, buffer was pH 8.8 0.05 M Tris and 0.05 M NaCl in deionized water. S-2444 (from Sigma), pyro-Glu-Gly-Arg-pNA at 0.5 mM in water was utilized as substrate. The same dilution procedure was used as for Factor VII and Factor X. Assay protocol is the same as for thrombin except 18.5 nM of human urokinase (from Sigma) was utilized. $IC_{50}$ was found to be 927±138 nM.

Tissue Plasminogen Activator (t-PA): Buffer, substrate and the dilution scheme of structure (13b) were the same as utilized for Factor VII assay.

Activated Protein C (aPC): Buffer was the same as used in thrombin assay. 1.25 mM S-2366 in the assay buffer was utilized as substrate. Dilutions of structure (13b) were the same as in urokinase assay.

Plasmin: Buffer (see thrombin assay); S-2551 (from Pharmacia), D-Val-Leu-Lys-pNA at 1.25 mM in assay buffer was utilized as substrate. For dilutions of structure (13b) (see urokinase assay).

In the trypsin assay, pH 7.8 Tris (0.10 M Tris and 0.02 M CaCl$_2$) was utilized as the buffer. BAPNA (from Sigma) was used at 1 mg/ml in 1% DMSO (v/v) deionized water solution as substrate. The same dilutions of structure (13b) were made as for Factor VII assay. 40 μl of 50 μg/ml bovine trypsin (from Sigma) and 20 μl of structure (13b) solution were added to a reaction well, the mixture was incubated for 5 minutes before 40 μl of 1 mg/ml BAPNA was added to initiate the reaction. The $IC_{50}$ of structure (13b) against trypsin was found to be 160±8 nM.

In the above assays, (D)FPR-CH$_2$Cl ("PPACK") was run as a control. Activity of structure (13b) compared to the control was enhanced (see Table 4).

TABLE 4

| | $IC_{50}$ (nM) | |
|---|---|---|
| Enzymes | PPACK | Structure (13b) |
| Thrombin | 1.5 | 1.2 |
| Factor VII | 200 | 140 |
| Factor X | 165 | 385 |
| Protein C | 281 | 528 |
| Plasmin | 699 | 978 |
| Trypsin | 212 | 16 |
| Urokinase | 508 | 927 |
| t-PA | 106 | 632 |

With respect to prothrombin time (PT), this was determined by incubating (30 minutes at 37° C.) 100 μl of control plasma (from Sigma) with 1-5 μl of buffer (0.05 M Tris, 0.15 M NaCl, pH=8.4) or test compound (i.e., PPACK or structure (13b)) in buffer. Then 200 μl of prewarmed (at 37° C. for ~10 minutes) thromboplastin with calcium (from Sigma) was rapidly added into the plasma sample. The time required to form clot was manually recorded with a stop watch (see Table 5), and was found to be comparable with PPACK.

TABLE 5

| | PT (second) | |
|---|---|---|
| Concentration | PPACK | Structure (13b) |
| 0 (Control) | 13 | 13 |
| 1 pM | — | 13 |
| 10 pM | — | 17 |
| 50 pM | — | 18 |
| 100 pM | — | 23 |
| 200 pM | — | 24 |
| 500 pM | 15 | 27 |
| 1 nM | 18 | 30 |
| 10 nM | 22 | 31 |
| 20 nM | 25 | — |

TABLE 5-continued

| | PT (second) | |
|---|---|---|
| Concentration | PPACK | Structure (13b) |
| 30 nM | — | 31 |
| 40 nM | 28 | — |
| 50 nM | — | 30 |
| 60 nM | 30 | — |
| 80 nM | 31 | 33 |

Example 5

Activity of a Representative β-Sheet Mimetic as a Protease Inhibitor

This example illustrates the ability of a further representative β-sheet mimetic of this invention to function as an inhibitor for thrombin, Factor VII, Factor X, urokinase, Tissue Plasminogen Activator, Activated Protein C, plasmin, tryptase and trypsin. The β-sheet mimetic of structure (20b) above was synthesized according to the procedures disclosed in Example 2, and used in this experiment.

All inhibition assays were performed at room temperature in 96 well microplates using Bio-Rad microplate reader (Model 3550). A 1 mM solution of structure (20b) in water served as the stock solution for all the inhibition assays. The hydrolysis of chromogenic substrates was monitored at 405 nm. The reaction progress curves were recorded by reading the plates, typically 60 times with 30 second to 2 minute intervals. Initial rates were determined by unweighted non-linear least-squares fitting to a first order reaction in GraFit (Erithacus Software Limited, London, England). The determined initial velocities were then nonlinear least-square fitted against the concentrations of structure (20b) using GraFit to obtain Ki. The general format of these assays are: 100 ml of a substrate solution and 100 ml of structure (20b) solution were added in a microplate well, then 50 ml of enzyme solution was added to initiate the reaction. Typically, eight structure (20b) concentration points were employed for Ki determination. The values of Ki of structure (20b) against nine serine proteases are tabulated in Table 6.

Thrombin: N-p-tosyl-Gly-Pro-Arg-pNA (from Sigma) was used at 0.5 mM concentration in 1% DMSO (v/v) pH8.0 tris buffer (tris, 50 mM, TWEEN 20, 0.1%, BSA, 0.1%, NaCl, 0.15 M, $CaCl_2$, 5 mM) as substrate. From structure (20b) stock solution two steps of dilution were made, first, 1:100 dilution in water, then 1:50 dilution in the pH8.0 tris buffer to serve as the first point (200 nM). Seven sequential dilutions were made from the first point for the assay.

Factor VII: S-2288 (from Pharmacia), D-Ile-Pro-Arg-pNA was used at 2.05 mM in the pH 8.0 tris buffer (see thrombin assay). From the stock of structure (20b), a 1:100 dilution was made in the tris buffer. From this concentration point seven more sequential dilutions were made for the assay.

Factor X: Buffer and substrate were the same as used for thrombin assay. A 1:100 dilution was made in the pH8.0 tris buffer to serve as the first point. Seven more dilutions from the first were made for the assay.

Urokinase: Buffer, 50 mM tris, 50 mM NaCl, pH=8.8. S-2444 (from Sigma), pyroGlu-Gly-Arg-pNA at 0.25 mM in buffer was utilized as substrate. 1:10 dilution in buffer was made from the stock of structure (20b) as the first point, then seven more dilutions from the first point were made for the assay.

Tissue Plasminogen Activator (t-PA): Buffer, substrate and the dilution scheme of structure (20b) were the same as utilized for Factor VII assay.

Activated Protein C (aPC): Buffer was the same as used in thrombin assay. 1.25 mM S-2366 in the assay buffer was utilized as substrate. Dilutions of structure (20b) were the same as in urokinase assay.

Plasmin: Buffer (see thrombin assay); S-2251 (from Pharmacia), D-Val-Leu-Lys-pNA at 1.25 mM in assay buffer was utilized as substrate. For dilutions of structure (20b) (see urokinase assay).

Tryptase: 0.1 M tris, 0.2 M NaCl, 0.1 mg/ml heparin, pH=8.0 was utilized as buffer. 0.5 mM S-2366 (from Pharmacia), L-pyroGlu-Pro-Arg-pNA in buffer was used as substrate. From the 1 mM stock of structure (20b), 10 mM solution was made in water, then 1 mM solution was made in buffer from the 10 mM solution to serve as the first concentration point. From this point seven more dilutions were made for the assay.

Trypsin: Buffer, substrate and the dilution scheme of structure (20b) were the same as used for thrombin.

TABLE 6

| | | $K_i$ (nM) | |
|---|---|---|---|
| Enzyme | Source | Assay Conc. (nM) | Structure (20b) |
| thrombin | bovine plasma | 2 | 0.66 |
| factor VII | human | 4 | 270 |
| factor X | bovine plasma | 8 | 966 |
| urokinase | human kidney | 3.7 | 600 |
| t-PA | human | 10 | 495 |
| APC | human plasma | 1 | 3320 |
| plasmin | bovine plasma | 4 | 415 |
| tryptase | human lung | 2 | 12.4 |
| trypsin | bovine pancreas | 5 | 0.64 |

As illustrated by the data presented in Table 6 above, structure (20b) functioned as a good thrombin inhibitor, with good specificity against fibrinolytic enzymes.

Example 6

Synthesis of Representative β-Sheet Mimetic

This example illustrates the synthesis of a representative β-sheet mimetic of this invention having the following structure (21):

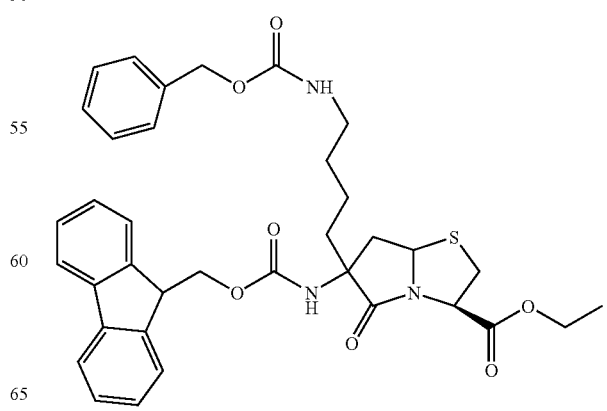

Structure (21) was synthesized as follows. A solution of 48 mg (0.859 mmol) N$^a$-FMOC-N$^e$-Cbz-a-ethanal-Lys-Ome [synthesized from N$^e$-Cbz-Lys-Ome by the same method used for the preparation of structure (5) from Phe-OMe], 15.9 mg (0.0859 mmol) Cys-OEt.HCl, and 13.2 µL (0.0945 mmol) TEA were in 0.43 mL CH$_2$Cl$_2$ were stirred under Ar for 2 hr at room temperature. Bis(bis(trimethylsilyl)amino)tin(II) (39.8 µL) was added and the reaction stirred overnight. The reaction solution was diluted with 10 mL EtOAc and washed with 6 mL each 10% citrate, water, and brine. The organic layer was dried over Na$_2$SO$_4$, filtered, and concentrated. The resulting residue was purified by flash chromatography on silica gel using 40% EtOAc/hexanes to give, after drying in vacuo, 12.9 mg of colorless oil (23%) as a mixture of diastereomers by $^1$H NMR (CDCl$_3$). MS ES(+) m/z 658.2 (MH$^+$, 30), 675.3 (M+Na$^+$, 100), 696.1 (M+K$^+$, 45).

Example 7

Synthesis of Representative β-Sheet Mimetic

This example illustrates the synthesis of a further representative β-sheet mimetic of this invention.

Synthesis of Structure (22)

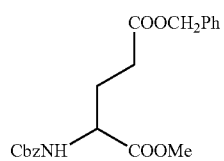
(22)

Structure (22) was synthesized as follows. To a stirred solution of Cbz-Glu(OBn)-OH (5 g, 13.5 mmol) with DMAP (270 mg) and methanol (3 ml) in dichloromethane (100 ml) was added EDCl (3 g) at 0° C. After stirring at 0° C. for 3 h, the solution was stirred at room temperature (rt) overnight. After concentration, the residue was taken up into EtOAc (100 ml) and 1N HCl (100 ml). The aqueous phase was separated and extracted with EtOAc (100 ml). The combined organic extracts were washed with sat. NaHCO$_3$ (100 ml), brine (100 ml), dried (MgSO$_4$), passed through a short pad of silica gel, and concentrated to provide 4.95 g an oil (95%). The product was pure enough to use for the next reaction without any further purification. $^1$H NMR (CDCl$_3$) δ 2.00 (m, 1H), 2.25 (m, 1H), 2.50 (m, 2H), 3.74 (s, 3H, OCH$_3$), 4.42 (m, 1H, CHNH), 5.10 and 5.11 (two s, 4H, CH$_2$Ph), 5.40 (d, 1H, NH), 7.35 (s, 10H, phenyls); MS CI(isobutane) m/z 386 (M+H$^+$).

Synthesis of Structure (23)

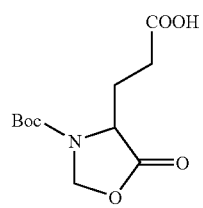
(23)

Structure (23) was synthesized as follows: To a stirred solution of L-Glu-OH (4.41 g, 30 mmol) with triethylamine (8.4 ml, 60 mmol) in 1,4-dioxane (40 ml) and H$_2$O (20 ml) was added Boc$_2$O (7 g, 32 mmol) at rt. After stirring for 1.5 h, the solution was acidified with 6N HCl (pH 2), and extracted with EtOAc (3×100 ml). The combined organic extracts were washed with H$_2$O (100 ml), brine (50 ml), dried (Na$_2$SO$_4$), and concentrated to provide an oil (9.5 g). Without further purification, the oil was used in the next reaction.

A mixture of above oil (9.5 g) with paraformaldehyde (5 g) and p-TsOH.H$_2$O (400 mg) in 1,2-dichloroethane (200 ml) was heated at reflux with a Dean-Stark condenser, which was filled with molecular sieve 4A, for 6 h. After addition of EtOAc (100 ml) and sat. NaHCO$_3$ (50 ml), the solution was extracted with sat. NaHCO$_3$ (3×50 ml). The combined aqueous extracts were acidified with 6N HCl (pH 2), and extracted with EtOAc (3×100 ml). The combined organic extracts were washed with brine (100 ml), dried (Na$_2$SO$_4$), and concentrated to provide an oil. The crude oil was purified by flash chromatography (hexane:EtOAc=80:20 to 70:30 to 60:40) to provide an oil (4.04 g, 52%) which solidified slowly upon standing. $^1$H NMR (CDCl$_3$) δ 1.49 (s, 9H, C(CH$_3$)$_3$), 2.18 (m, 1H, —CH$_2$CH$_2$), 2.29 (m, 1H, CH$_2$CH$_2$), 2.52 (m, 2H, —CH$_2$CH$_2$—), 4.33 (m, 1H, NHCHCH$_2$), 5.16 (d, 1H, J=4.5 Hz, NCH$_2$O), 5.50 (br, 1H, NCH$_2$O); $^{13}$C NMR (CDCl$_3$) δ 25.85, 28.29, 29.33, 54.16, 79.10, 82.69, 152.47, 172.37, 178.13; MS (ES+) m/z 260 (M+H$^+$), 282 (M+Na$^+$), 298 (M+K$^+$).

Synthesis of Structure (24)

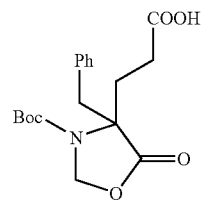
(24)

Structure (24) was synthesized as follows. To a stirred solution of 1,1,1,3,3,3-hexamethyldisilazane (2.1 ml, 10 mmol) in THF (10 ml) was added n-BuLi (4 ml of 2.5M in hexane, 10 mmol) at 0° C. The resulting solution was stirred at the same temperature for 30 min. After cooling to −78° C., to this stirred solution was added a solution of carboxylic acid (23) (1.02 g, 3.94 mmol) in THF (10 ml) followed by rinsings of the addition syringe with 5 ml THF. The resulting solution was stirred at −78° C. for 1 h, and PhCH$_2$Br (0.46 ml, 3.9 mmol) was added. After stirring at −30° C. for 3 h, to this solution was added 1N HCl (50 ml) and the resulting solution was extracted with EtOAc (100 ml). The organic extract was washed with brine (50 ml), dried (Na$_2$SO$_4$), and concentrated to provide an oil. The crude product was purified by flash chromatography (hexane:EtOAc=80:20 to 60:40 to 50:50) to provide a foamy solid (1.35 g, 98%): $^1$H NMR (CDCl$_3$) δ 1.55 and 1.63 (two s, 9H, ratio 1.5:1 by rotamer, OC(CH$_3$)$_3$), 2.2-2.4 (m, 3H, —CH$_2$CH$_2$—), 2.6-2.9 (set of m, 1H, —CH$_2$CH$_2$—), 3.04 (d, 1H, J=13.5 Hz, —CH$_2$Ph), 3.33 and 3.58 (two d, 1H, J=13 Hz, ratio 2:1, —CH$_2$Ph), 4.03 (two d, 1H, J=4 Hz, A of ABq, —NCH$_2$O—), 4.96 (two d, 1H, J=4 Hz, B of ABq, —NCH$_2$O—); MS (ES−) m/z 348 (M−H+).

Synthesis of Structure (25)

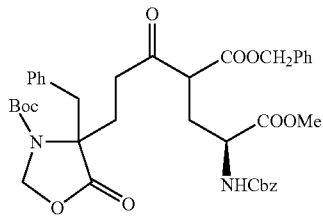

(25)

Synthesis of structure (25) was carried out as follows. To a stirred solution of carboxylic acid (24) (1.05 g, 3.0 mmol) in dry THF (5 ml) was added 1,1'-carbonyldiimidazole (500 mg, 3.1 mmol) at rt. The resulting solution was stirred at rt for 30 min. The solution of acyl imidazole was used for the next reaction without purification.

Meanwhile, to a stirred solution of 1,1,1,3,3,3-hexamethyldisilazane (1.6 ml, 7.5 mmol) in THF (5 ml) was added n-BuLi (3 ml of 2.5 M solution in hexane, 7.5 mmol) at 0° C. After stirring at the same temperature for 30 min, the solution was cooled to −78° C. To the stirred solution was added a solution of Cbz-Glu(OBn)-OMe (1.16 g, 3 mmol) in THF (5 ml) followed by rinsings of the addition syringe with 2 ml THF. The resulting solution was stirred at the same temperature for 15 min. To this stirred solution was added the above acyl imidazole in 3 ml THF. After stirring 30 min. at −78° C., to this solution was added sat. NH$_4$Cl (50 ml) and extracted with EtOAc (2×75 ml). The combined organic extracts were washed with sat. NaHCO$_3$ (50 ml), brine (50 ml), dried (Na$_2$SO$_4$), passed through a short pad of silica gel, and concentrated to provide an oil. The crude product was purified by flash chromatography (hexane: EtOAc=90:10 to 80:20 to 70:30 to 60:40) to provide an oil (1.48 g, 69%): MS (ES+) m/z 734.4 (M+NH$_4^+$).

Synthesis of Structure (26a)

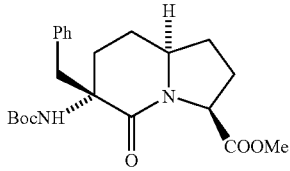

(26a)

Structure (26a) was synthesized as follows. A stirred solution of above starting keto ester (25) (530 mg, 0.7 mmol) in EtOH/AcOH (10/1 ml) was treated with 10% Pd/C (ca. 100 mg) under 20 atm pressure of H$_2$ for 2 days. After filtration through a short pad of Celite, the filtrate was concentrated and dissolved in EtOAc (50 ml). The solution was washed with 1N HCl (30 ml), sat. NaHCO$_3$ (30 ml), brine (30 ml), dried (Na$_2$SO$_4$), and concentrated to provide an oil. The crude product was purified by flash chromatography (hexane: EtOAc=80:20 to 60:40 to 50:50 to 20:80 to 0:100) to provide a foamy solid (95 mg, 34%). TLC (EtOAc) R$_f$ 0.68; NMR (CDCl$_3$) δ 1.38 (two s, 9H, OC(CH$_3$)$_3$), 1.63 (s, 1H), 1.75 (m, 2H), 2.05 (m, 5H), 2.1-2.3 (set of m, 1H), 3.00 (d, 1H, J=14 Hz, CH$_2$Ph), 3.21 (d, 1H, J=13.5 Hz, CH$_2$Ph), 3.74 (collapsed two s, 4H, OCH$_3$ and NCH), 4.53 (d, 1H, J=9.5 Hz), 5.01 (br, 1H, NH); MS (ES+) m/z 403 (M+H$^+$), 425 (M+Na$^+$). Stereochemistry was assigned by 2D NMR.

Synthesis of Structure (27a)

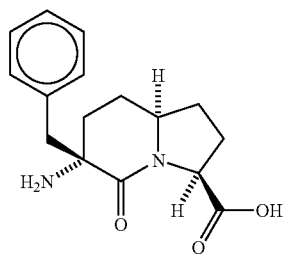

(27a)

Structure (27a) was synthesized as follows. To a solution of 28 mg (0.070 mmol) of the bicyclic ester (26a) stirred in 1 ml THF at room temperature was added 0.14 ml 1.0 M aqueous lithium hydroxide solution. The mixture was stirred vigorously for 20 h then quenched with 5% aqueous citric acid (1 ml). The mixture was extracted with ethyl acetate (3×25 ml) then the combined extracts were washed with water and brine and dried over anhydrous sodium sulfate. Filtration and concentration of the filtrate under vacuum gave 26 mg of white foam, used without further purification.

Synthesis of Structure (28a)

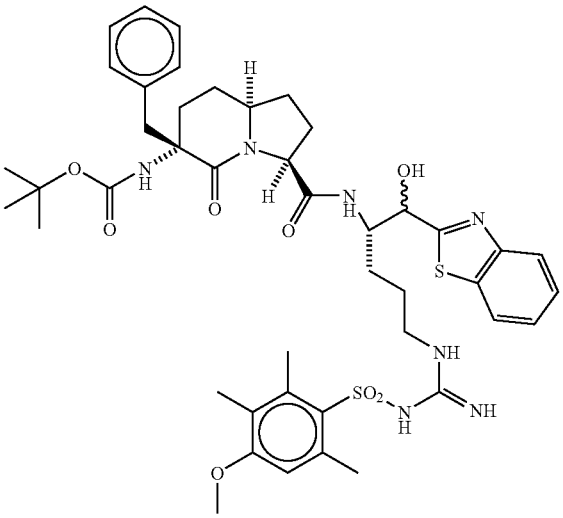

(28a)

Structure (28a) was synthesized as follows. The bicyclic acid (27a) (26 mg, 0.067 mmol), benzothiazolylarginol trifluoroacetic acid salt (structure (17) 61 mg, 0.083 mmol) EDC (21 mg, 0.11 mmol) and HOBt hydrate (16 mg, 0.10 mmol) were dissolved in THF (5 ml) and diisopropylethylamine (0.34 ml, 1.9 mmol) was added. The mixture was stirred at room temperature for 15 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 60 mg of a yellow glass.

¹H NMR analysis indicated a mixture of four diastereomeric amides. MS (ES+): m/z 898 (M+Na⁺).

Synthesis of Structure (29a)

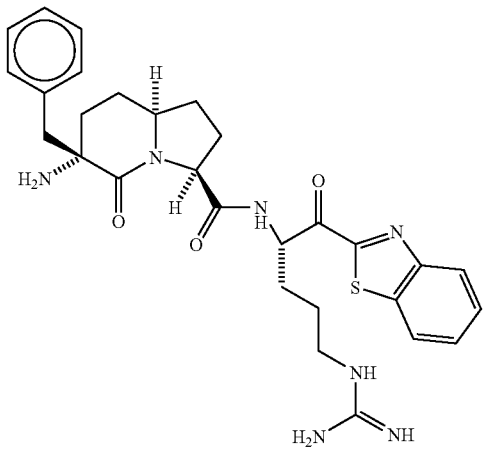

(29a)

A β-sheet mimetic of structure (29a) was synthesized as follows. The crude hydroxybenzothiazole (28a) (60 mg, 0.068 mmol) was dissolved in CH₂Cl₂ (2 ml) and Dess-Martin periodinane (58 mg, 0.14 mmol) was added. The mixture was stirred at room temperature for 6 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 42 mg of yellow glass. ¹H NMR analysis indicated a mixture of two diastereomeric ketobenzothiazoles.

The ketobenzothiazole (42 mg, 0.048 mmol) was dissolved in 95% aqueous trifluoroacetic (0.95 ml) acid and thioanisole (0.05 ml) was added. The resulting dark solution was stirred for 18 hours at room temperature then concentrated under vacuum to a dark brown gum. The gum was triturated with diethyl ether and centrifuged. The solution was removed and the solid remaining was triturated and collected as above two more times. The yellow solid was dried in a vacuum desiccator for 2 hours then purified by HPLC to give 1.4 mg of the deprotected product. MS (ES+): 562.4 (M+H⁺). HPLC: (t$_R$=21.17 min.)

Synthesis of Structure (26b)

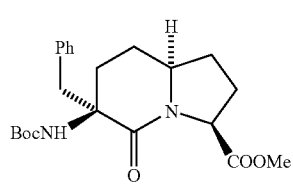

(26b)

Structure (26b) was synthesized as follows. A stirred solution of above starting keto ester (25) (615 mg, 0.86 mmol) in MeOH/AcOH (10/1 ml) was treated with 10% Pd/C (ca. 60 mg) under 20 atm pressure of H₂ for 3 days. After filtration through a short pad of Celite, the filtrate was concentrated to provide an oil. The crude product was purified by flash chromatography (hexane:EtOAc=80:20 to 60:40 to 50:50 to 0:100) to collect the more polar fraction (50 mg). Rf 0.12 (hexane: EtOAc=60:40); MS (ES+) m/z 433 (M+H⁺).

Above oil was treated with p-TsOH.H₂O (5 mg) in 1,2-dichloroethane (10 ml) at reflux temperature for 2 days. After concentration, the oily product was purified by preparative TLC (hexane: EtOAc=80:20 to 60:40) to give an oil (10 mg). TLC Rf 0.36 (hexane:EtOAc=60:40); ¹H NMR (CDCl₃) δ 1.43 (s, 9H), 1.66 (m, 3H), 1.89 (m, 3H), 2.14 (m, 1H), 2.75 (m, 1H), 2.98 (m, 1H, CHN), 3.72 (s, 3H, Me), 4.30 (m, 1H), 5.59 (d, 1H, NH), 7.1-7.3 (m, 5H, phenyl); MS CI(NH₃) 403.2 (M+H⁺). Stereochemistry was assigned by 2D NMR.

Synthesis of Structure (28b)

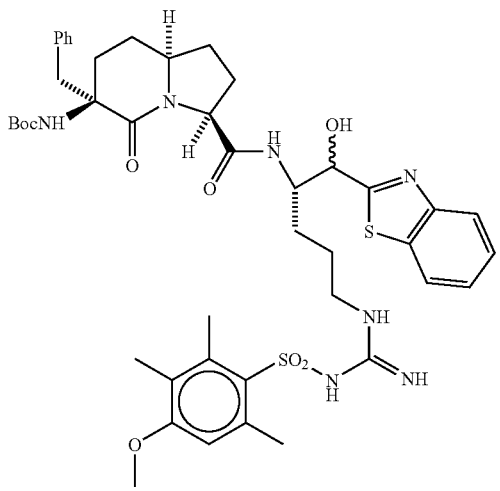

(28a)

Structure (28b) was synthesized as follows. To a solution of 12 mg (0.030 mmol) of the bicyclic ester (26b) stirred in THF 1 ml at room temperature was added 0.060 ml 1.0 M aqueous lithium hydroxide solution. The mixture was stirred vigorously for 25 h then quenched with 5% aqueous citric acid (1 ml). The mixture was extracted with ethyl acetate (3×25 ml) then the combined extracts were washed with water and brine and dried over anhydrous sodium sulfate. Filtration and concentration of the filtrate under vacuum gave 19 mg of white foam.

The foam, benzothiazolylarginol trifluoroacetic acid salt (30 mg, 0.041 mmol) EDC (10 mg, 0.052 mmol) and HOBt hydrate (9 mg, 0.059 mmol) were dissolved in THF (2 ml) and diisopropylethylamine (0.026 ml, 0.15 mmol) was added. The mixture was stirred at room temperature for 30 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 28 mg of a yellow glass. $^1$H NMR analysis indicated a mixture of four diastereomeric amides. MS (ES+): m/z 898 (M+Na$^+$).

Synthesis of Structure (29b)

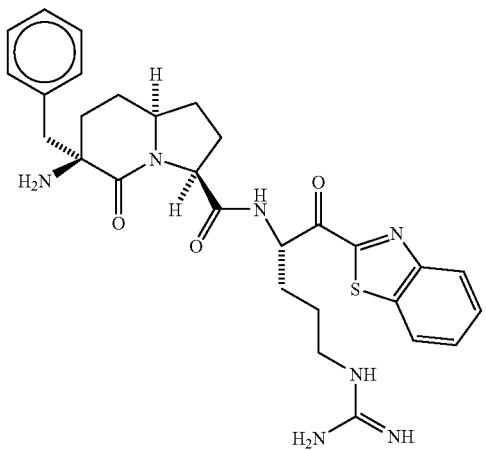

(29b)

Structure (29b) was synthesized as follows. The crude hydroxybenzothiazole (28b) (28 mg) was dissolved in CH$_2$Cl$_2$ (2 ml) and Dess-Martin periodinane (29 mg, 0.071 mmol) was added. The mixture was stirred at room temperature for 18 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 32 mg of yellow glass. $^1$H NMR analysis indicated a mixture of two diastereomeric ketobenzothiazoles.

The ketobenzothiazole (32 mg) was dissolved in 95% aqueous trifluoroacetic (0.95 ml) acid and thioanisole (0.05 ml) was added. The resulting dark solution was stirred for 20 hours at room temperature then concentrated under vacuum to a dark brown gum. The gum was triturated with diethyl ether and centrifuged. The solution was removed and the remaining solid was triturated and collected as above two more times. The yellow solid was dried in a vacuum desiccator for 2 hours then purified by HPLC to give 1.3 mg of the deprotected product. MS (FB+): 562.36 (M+H$^+$); HPLC: $t_R$=21.51 min. (Gradient 0 to 90% 0.1% TFA in CH$_3$CN/0.1% TFA in H$_2$O over 40 min.)

Example 8

Activity of Representative β-Sheet Mimetic as a Protease Inhibitor

This example illustrates the ability of a further representative β-sheet mimetic of this invention to function as an inhibitor for thrombin, Factor VII, Factor X, Factor XI, and trypsin. The β-sheet mimetics of structures (29a) and (29b) above were synthesized according to the procedures disclosed in Example 7, and used in this experiment.

The proteinase inhibitor assays were performed as described in Example 5 except as described below for Factor XI. The results are presented in Table 7.

Factor XI. The same buffer was utilized in this assay as in the thrombin assay. 1 mM S-2366 (from Pharmacia), L-pyroGlu-Pro-Arg-pNA, solution in water was used as substrate. From a 1 mM stock solution of structure (29a) or (29b) in water, a 1:10 dilution was made in buffer. From this 100 μM solution, seven serial 1:5 dilutions were made in buffer for assay.

TABLE 7

| | $K_i$ (nM) | |
|---|---|---|
| Enzymes | Structure (29a) | Structure (29b) |
| Thrombin | 10.4 | 0.085 |
| Trypsin | 0.54 | 0.20 |
| Factor VII | 1800 | — |
| Factor X | 4600 | 17 |
| Factor XI | 391 | — |

Example 9

Activities of Representative β-Sheet Mimetics as a Protease Inhibitor

This example illustrates the ability of further representative β-sheet mimetics of this invention to function as an inhibitor for thrombin, Factor VII, Factor X, Factor XI, tryptase, aPC, plasmin, tPA, urokinase and trypsin. The β-sheet mimetics of structures (20) and (29b) above were synthesized according to the procedures disclosed in Examples 2 and 7, respectively, and used in this experiment.

The proteinase inhibitor assays were performed as described in Example 5 except as described in Example 8 for Factor XI. The results are presented in Table 8.

TABLE 8

| | Structure (20b) | | Structure (29b) | |
|---|---|---|---|---|
| 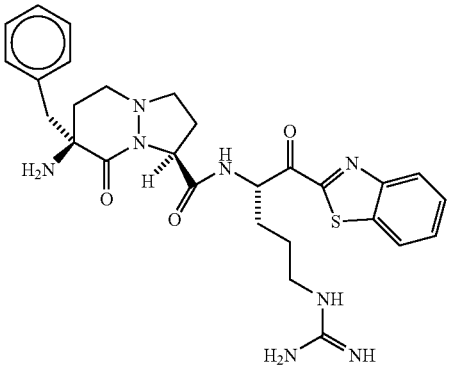 | | | 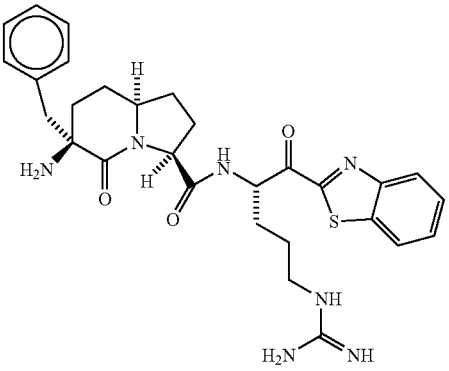 | |
| | Ki (nM) | Selectivity* | Ki (nM) | Selectivity* |
| Thrombin | 0.65 | 1 | 0.085 | 1 |
| Trypsin | 0.62 | 0.95 | 0.23 | 2.7 |
| Factor VII | 270 | 415 | 200 | 2353 |
| Factor X | 222 | 342 | 19.3 | 227 |
| Factor XI | 27.0 | 42 | 75.3 | 886 |
| Tryptase | 12.3 | 18.9 | 9.0 | 106 |
| aPC | 3320 | 5108 | 1250 | 14706 |
| Plasmin | 415 | 638 | 251 | 2953 |
| tPA | 495 | 762 | 92.9 | 1093 |
| Urokinase | 600 | 923 | 335 | 3941 |

*selectivity is the ratio of Ki of an enzyme to the Ki of thrombin

Example 10

Synthesis of Representative β-Sheet Mimetics

This example illustrates the synthesis of a further representative β-sheet mimetic of this invention.

Synthesis of Structure (30)

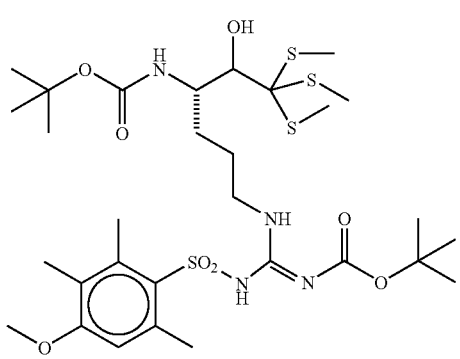

(30)

Structure (30) was synthesized as follows. n-Butyllithium (700 µL, 1.75 mmol, 2.5M in hexanes) was added over 5 min to a solution of tris(methylthio)methane (256 µL, 1.95 mmol) in THF (1 ml) at −78° C. The mixture was stirred for 40 min then treated with a solution of bis-Boc-argininal (structure (16) from Example 2) (100 mg, 1.75 mmol) in 2 ml THF, dropwise, over a period of 5 min. After stirring for 1.5 h, the reaction was quenched with saturated NH$_4$Cl solution and allowed to warm to room temperature. The layers were separated and the aqueous layer extracted with EtOAc (3×), washed with brine (1×), dried (Na$_2$SO$_4$) and concentrated. Purification by flash chromatography (EtOAc:Hexane 1:4) yielded 93 mg (73%) of the orthothiomethyl ester (structure (30)) and 8 mg of recovered aldehyde (structure (16)). $^1$H NMR (500 MHz, CDCl$_3$.) δ 9.80 (s, 1H), 8.32 (t, J=5.0 Hz, 1H), 6.54 (s, 1H), 5.23 (d, J=9.0 Hz, 1H), 4.0 (m, 1H), 3.84 (s, 3H), 3.64 (br s, 1H), 3.38 (br s, 1H), 3.31 (m, 2H), 2.70 (s, 3H), 2.62 (s, 3H), 2.19 (s, 9H), 2.14 (s, 3H), 1.68-1.50 (m, 4H), 1.49 (s, 9H), 1.43 (s, 9H).

Synthesis of Structure (31)

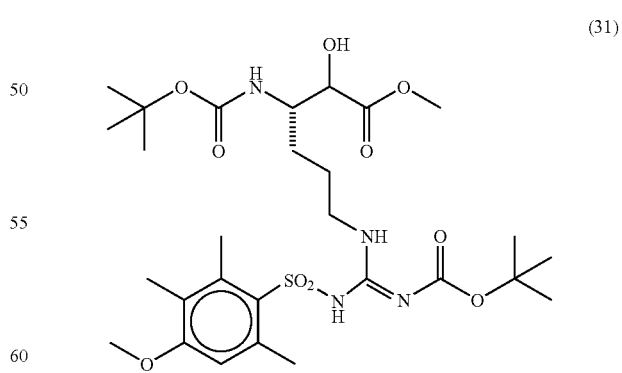

(31)

Structure (31) was synthesized as follows. A mixture of 77 mg (0.11 mmol) of the orthothiomethyl ester (structure (30)), 117 mg (0.43 mmol) of mercuric chloride, and 39 mg (0.18 mmol) of mercuric oxide in 2.5 ml of 12:1 methanol/water was stirred at rt for 4 h. The mixture was filtered through Celite and the residue washed with EtOAc (3×). The filtrate was diluted with water and extracted with EtOAc (3×). The organic layer was washed twice with 75% NH$_4$OAc/NH$_4$Cl, then with NH$_4$Cl and dried (Na$_2$SO$_4$). The solvent was removed in vacuo and the residue purified by flash chromatography (EtOAc/Hex, 1:3) to give 48 mg (72%) of the two diastereomers of structure (31) in a 1:2.7 ratio. $^1$H NMR (500 MHz, CDCl$_3$) (major diastereomer) δ 9.80 (s, 1H), 8.33 (t, J=5.0 Hz, 1H), 6.54 (s, 1H), 4.66 (d, J=10.5 Hz, 1H), 4.08 (dd, J=5.0, 2.0 Hz, 1H), 3.97 (m, 1H), 3.84 (s, 3H), 3.77 (s, 3H), 3.30 (m, 2H), 3.06 (d, J=5.0 Hz, 1H), 2.70 (s, 3H), 2.63 (s, 3H), 2.14 (s, 3H), 1.68-1.50 (m, 4H), 1.49 (s, 9H), 1.40 (s, 9H); MS (ES+) m/z 631.5 (M+H$^+$).

Synthesis of Structure (32)

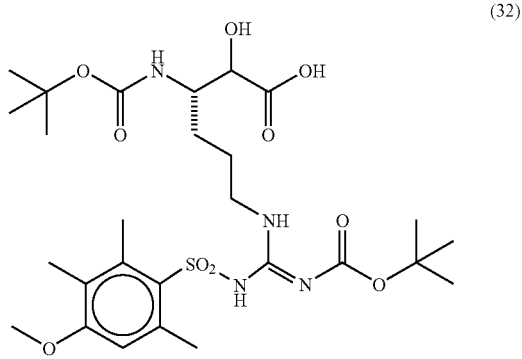

(32)

Structure (32) was synthesized as follows. A solution of 32 mg of the methyl ester (structure (31)) (0.051 mmol) in THF/water (4 ml, 1:3) was treated with 5 mg (0.119 mmol) of LiOH.H$_2$O. After stirring for 45 min, the reaction was diluted with 5% citric acid and extracted with ethyl acetate (3×). The combined extracts were washed with brine, dried over Na$_2$SO$_4$ and concentrated to give 30 mg (96%) of structure (32) as a white solid. The product was used without further purification. $^1$H NMR 500 MHz, CDCl$_3$) δ 9.80 (br s, 1H), 8.29 (br s, 1H), 6.54 (s, 1H), 5.62 (br s, 1H), 4.08 (m, 1H), 3.82 (s, 3H), 3.27 (br s, 3H), 2.69 (s, 3H), 2.62 (s, 3H), 2.13 (s, 3H), 1.65-1.50 (m, 4H), 1.48 (s, 9H), 1.37 (s, 9H); MS (ES−) m/z 615.5 (M−H+).

Synthesis of Structure (33)

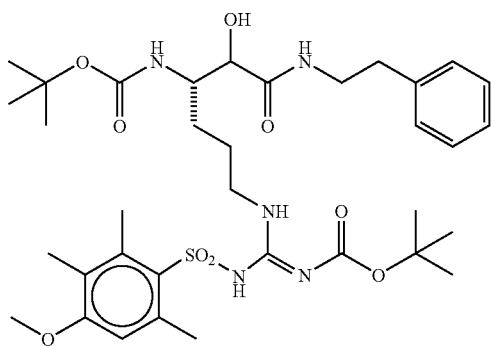

(33)

Structure (33) was synthesized as follows. To a solution of the compound of structure (32) (29 mg, 0.047 mmol), HOBt (8 mg, 0.056 mmol) and EDC (11 mg, 0.056 mmol) in THF (5 ml), phenethylamine (7 ml, 0.056 mmol) was added followed by diisopropylethylamine (12 µL, 0.071 mmol). The reaction mixture was stirred at rt overnight and diluted with 5% citric acid. The organic layer was separated and the aqueous phase extracted with EtOAc (3×). The combined extracts were washed with a saturated solution of NaHCO$_3$, brine, dried over Na$_2$SO$_4$, and filtered. After concentration the crude product was purified by chromatography (EtOAc/Hex, 1:1) to give 26 mg (77%) of structure (33) over two steps. $^1$H NMR (500 MHz, CDCl$_3$) δ 9.84 (s, 1H), 8.34 (t, J=5 Hz, 1H), 7.28 (m, 3H), 7.21 (m, 2H), 7.04 (m, 1H), 6.55 (s, 1H), 5.16 (d, J=8.5 Hz, 1H), 4.56 (d, J=5 Hz, 1H), 4.11 (dd, J=5.0, 3.0 Hz, 1H), 3.98 (m, 1H), 3.84 (s, 3H), 3.66 (m, 1H), 3.51 (m, 2H), 3.17 (m, 1H), 2.81 (t, J=7.5 Hz, 2H), 2.71 (s, 3H), 2.65 (s, 3H), 2.14 (s, 3H), 1.68-1.52 (m, 4H), 1.49 (s, 9H), 1.39 (s, 9H); MS (FAB+) m/z 720.6 (M+H$^+$) (FAB−) m/z 718.5 (M−H$^+$).

Synthesis of Structure (34)

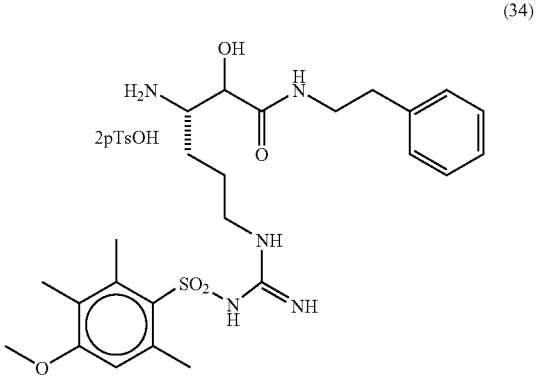

(34)

Structure (34) was synthesized as follows. To a solution of phenethylamide (structure (33), 25 mg, 0.035 mmol) in THF (5 ml) was added 18 mg of p-toluenesulfonic acid monohydrate (0.093 mmol). The reaction mixture was stirred at rt overnight to give a baseline spot by TLC. The solution was concentrated in vacuo, and the residue washed twice with ether removing excess pTsOH to give structure (34) as a yellowish-white solid, which was used without further purification. $^1$H NMR (500 MHz, CDCl$_3$) was consistent with the expected product, however, individual peak assignment was difficult due to broadening. MS (ES+) m/z 520.4 (M+H$^+$).

Structure (34) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (35) as identified in Table 9 below.

Example 11

Synthesis of Representative β-Sheet Mimetics

This example illustrates the synthesis of a further representative β-sheet mimetic of this invention.

Synthesis of Structure (36)

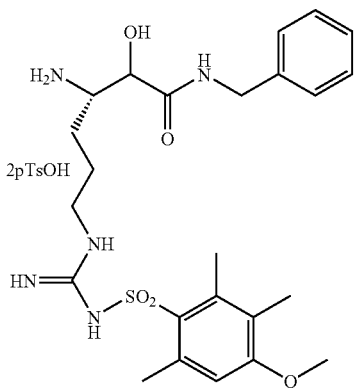
(36)

Structure (36) was synthesized in an analogous fashion to compound (34) starting with benzylamine and structure (32). $^1$H NMR (500 MHz, CDCl$_3$) was consistent with the expected product, however, individual peak assignment was difficult due to broadening. MS (FAB+) m/z 506.4 (M+H$^+$).

Structure (36) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (37) as identified in Table 9 below.

Example 12

Synthesis of Representative β-Sheet Mimetics

This example illustrates the synthesis of a further representative β-sheet mimetic of this invention.

Synthesis of Structure (38)

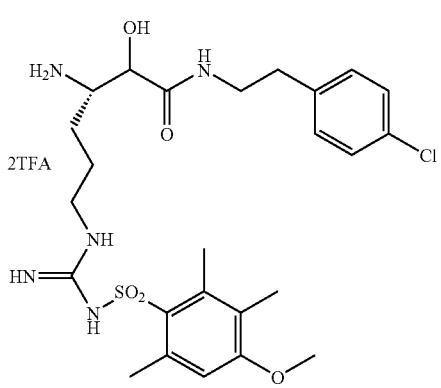
(38)

Structure (38) was synthesized in an analogous fashion to structure (34) starting with p-chlorophenethylamine and structure (32). $^1$H NMR (500 MHz, CDCl$_3$) was consistent with the expected product, individual peak assignment was difficult due to broadening. MS (ES+) m/z 554.5 (M+H$^+$).

Structure (38) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (39) as identified in Table 9 below.

Example 13

Synthesis of Representative β-Sheet Mimetics

This example illustrates the synthesis of a further representative β-sheet mimetic of this invention.

Synthesis of Structure (40)

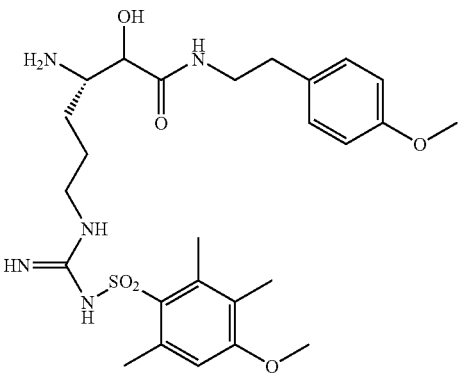
(40)

Structure (40) was synthesized in an analogous fashion to compound (34) using p-methoxyphenethylamine and structure (32). $^1$H NMR (500 MHz, CDCl$_3$) was consistent with the expected product, however, individual assignment was difficult due to broadening. MS (ES+) m/z 550.5 (M+H$^+$).

Structure (40) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (41) as identified in Table 9 below.

Example 14

Synthesis of Representative β-Sheet Mimetics

This example illustrates the synthesis of a further representative β-sheet mimetic of this invention.

Synthesis of Structure (42)

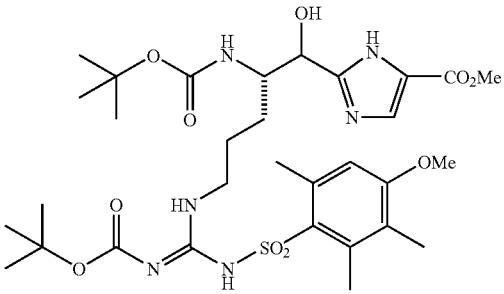
(42)

Structure (42) was prepared as follows. In a 10 ml round-bottomed flask were added CH$_2$Cl$_2$ (10 ml), methyl 2,3-dimethylaminopropionate dihydrochloride (19.9 mg, 0.103 mmol, 1.5 eq), and diisopropylethylamine (53 ml, 0.304 mmol, 4.4 eq). This suspension was stirred magnetically at room temperature for 1 h at which time was added the compound of structure (30) (50 mg, 0.068 mmol, 1 eq), mercury (II)chloride (82.4 mg, 0.304 mmol, 4.4 eq), and mercury(II) oxide (25.7 mg, 0.120 mmol, 1.7 eq). The resulting yellow suspension was stirred for 16.5 h during which time the suspension turned gray. The reaction was diluted with CH$_2$Cl$_2$ (50 ml), washed with saturated aqueous NH$_4$Cl (5 ml), saturated aqueous NaCl (5 ml) and dried over Na$_2$SO$_4$. The cloudy suspension was filtered and the solvent removed in vacuo. The white solid was purified on preparative thin-layer chromatography to produce the imidazoline structure (42) (25.3 mg, 52% yield) as a clear amorphous solid: R$_f$ 0.11 (10% MeOH/CHCl$_3$); $^1$H NMR (500 MHz, CDCl$_3$) δ 9.82 (s, 0.6H, N'H, mixture of tautomers), 9.78 (s, 0.4H, N"H), 8.35 (dd, J=4.3, 11 Hz, $^1$H, N-5), 6.54 (s, 1H, ArH), 5.08 (d, J=11 Hz, 1H, CHOH), 4.52 (m, 1H, imidazoline CH$_2$), 4.38 (d, J=21 Hz, 1H), 3.8-4.0 (m, 2H), 3.86 (S, 3H, CO$_2$CH$_3$), 3.767 (s, 3H, ArOCH$_3$), 3.5-3.7 (m, 2H, C-5 CH$_2$), 3.16-3.27 (m, C-5 CH$_2$), 2.70 (s, 3H, ArCH$_3$), 2.63 (s, 3H, ArCH$_3$), 2.14 (s, 3H, ArCH$_3$), 1.5-1.7 (m, 4H, C-3 and C-4 CH2), 1.49 (s, 9H, Boc), 1.46 (s, 9H, Boc); IR (film) 1725.56, 1685.68, 1618.36, 1585.45, 1207.09, 1148.85 cm$^{-1}$; MS (ES+) m/e 699.4 (M+H$^+$)

Synthesis of Structure (43)

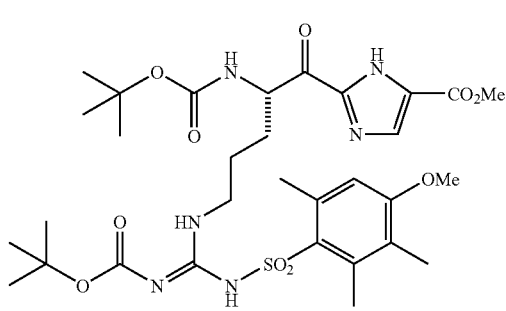

Structure (43) was synthesized as follows. In a 25 ml round-bottomed flask was placed the compound of structure (42) (230 mg, 0.33 mmol), CHCl$_3$ (5 ml) and MnO$_2$ (500 mg, 5.75 mmol, 17.4 eq). After stirring for 5 h the suspension was filtered and the solid washed with methanol. The solvent was removed in vacuo and the residue was dissolved in ethyl acetate (5 ml) and methanol (1 ml) and a fresh portion of MnO$_2$ (500 mg) was introduced and the reaction stirred for 15 h at room temperature. The solid was filtered and the solvent removed in vacuo. The residue was purified via column chromatography on silica gel, eluting with 1:1 ethyl acetate:hexane, then pure ethyl acetate, then 1:9 methanol:ethyl acetate to obtain the desired product (structure (43), 190 mg, 83% yield) as an amorphous solid: R$_f$ 0.64 (70:30-ethyl acetate: hexane); $^1$H NMR (500 MHz, CDCl$_3$) δ 10.70 (bs, 1H, imidazole NH), 9.70 (s, 1H), 8.28 (s, 1H), 7.84 (s, 1H), 6.54 (s, 1H, ArH), 5.35 (m, 1H, aH), 5.25 (s, 1H, BocNH), 3.926 (s, 3H), 3.840 (s, 3H), 3.15-3.40 (m, 2H), 2.682 (s, 3H), 2.133 (s, 3H), 1.52-1.70 (m, 4H), 1.470 (s, 9H), 1.424 (s, 9H); IR (film) 1724.68, 1619.03, 1277.72, 1151.93, 1120.61 cm$^{-1}$; MS (ES+) m/e 695.2 (M+H+, 22), 717.2 (M+Na$^+$, 100).

Synthesis of Structure (44)

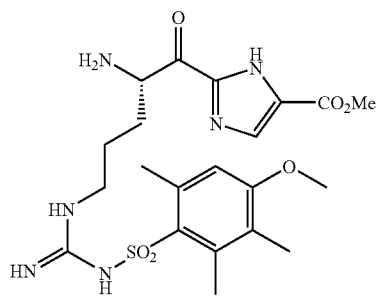

Structure (44) was synthesized by the same method used to construct structure (33) to structure (34). The product was used in the coupling without further purification.

Structure (44) was reacted with structure (9a) of Example 1 (in an analogous manner to the procedure described in Example 2 for the synthesis of structure (18)), followed by deprotection (in an analogous manner as described with respect to the deprotection of structure (19) respectively) to provide structure (45) as identified in Table 9 below. In the preparation of structure (45), the coupling step was performed with the carbonyl compound of structure (44), rather than with the analogous hydroxy compound.

Example 15

Synthesis of Representative β-Sheet Mimetics

This example illustrates the synthesis of a further representative β-sheet mimetic of this invention.

Synthesis of Structure (46)

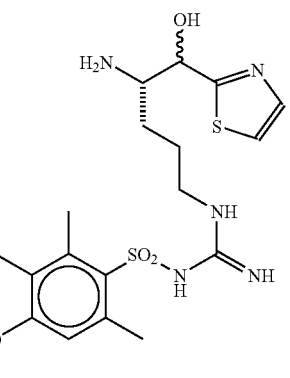

Structure (46) was synthesized in an analogous fashion to structure (17) starting from structure (16) and thiazole. This compound was used in the coupling step without further purification.

Structure (46) was reacted with structure (9a) of Example 1 (in an analogous manner to the procedure described in Example 2 for the synthesis of structure (18)), followed by oxidation and deprotection (in an analogous manner as

99 described with respect to the oxidation and deprotection of structures (18) and (19), respectively) to provide structure (47) as identified in Table 9 below.

Example 16

Synthesis of Representative β-Sheet Mimetics

This example illustrates the synthesis of a further representative β-sheet mimetic of this invention.

Synthesis of Structure (48)

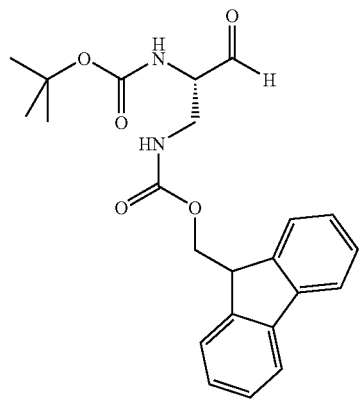

To a solution of α-Boc-β-Fmoc-2,3-diaminopropionic acid (818 mg, 1.92 mmol) stirred in THF (5 ml) at −25° C. was added 4-methylmorpholine (0.23 ml, 2.1 mmol) followed by isobutylchloroformate (0.25 ml, 1.9 mmol). The resulting suspension was stirred for 5 minutes and then filtered with the aid of 5 ml of THF. The filtrate was cooled in an ice/water bath then sodium borohydride (152 mg, 0.40 mmol) dissolved in water (2.5 ml) was added dropwise. The mixture was stirred for 15 minutes then water (50 ml) was added and the mixture was extracted with $CH_2Cl_2$ (3×50 ml). The combined extracts were washed with brine, dried over anhydrous sodium sulfate and filtered. Concentration of the filtrate under vacuum yielded a pale yellow solid that was purified by flash chromatography (50% ethyl acetate/hexanes eluent) to give 596 mg of the alcohol as a white solid.

The alcohol (224 mg, 0.543 mmol) was dissolved in methylene chloride and Dess-Martin periodinane (262 mg, 0.64 mmol) was added. The mixture was stirred at room temperature for 1 h then diluted with ethyl acetate (50 ml) and extracted sequentially with 10% aqueous $Na_2S_2O_3$, saturated aqueous $NaHCO_3$, and brine. The organic solution was dried over anhydrous sodium sulfate, filtered and concentrated under vacuum to a white solid. Purification of the solid by flash chromatography yielded 169 mg of the aldehyde structure (48) as a white solid.

100

Synthesis of Structure (49)

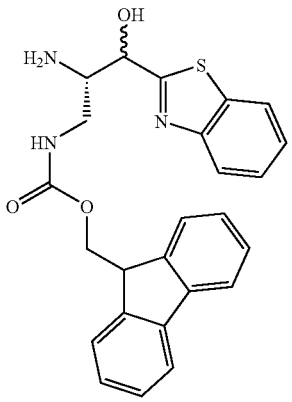

Structure (49) was synthesized in an analogous fashion to structure (17) starting from structure (48) and benzothiazole. This compound was used as a 1:1 mixture of diastereomers in the coupling step (described below) without further purification. MS (EI+): m/z 446.4 (M+H$^+$).

Synthesis of Structure (50)

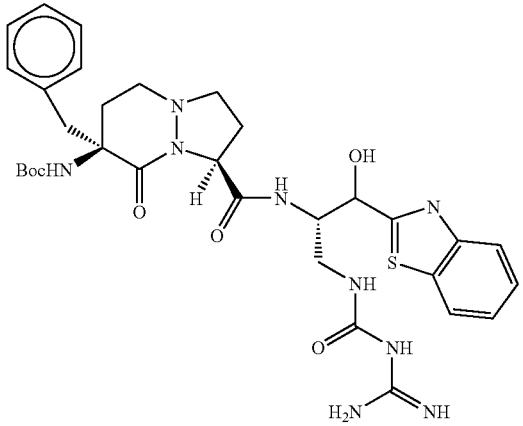

Structure (49) and bicyclic acid structure (9a) (27 mg, 0.069 mmol) and HOBt hydrate (71 mg, 0.46 mmol) were dissolved in THF (1 ml) and diisopropylethylamine (0.0.059 ml, 0.34 mmol) was added followed by EDC (19 mg, 0.099 mmol). The mixture was stirred at room temperature for 20 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 61 mg of a yellow foam. $^1$H NMR analysis indicated a mixture of diastereomeric amides.

The foam was dissolved in $CH_3CN$ and diethylamine was added. The solution was stirred at room temperature for 30 minutes then concentrated under vacuum to a yellow foam. The foam was rinsed with hexanes and dissolved in DMF (0.5 ml). In a separate flask, carbonyldiimidazole (16 mg, 0.99 mmol) and guanidine hydrochloride (10 mg, 0.10 mmol) were dissolved in DMF (1 ml) and diisopropylethylamine (0.035 ml, 0.20 mmol) was added followed by DMAP (1 mg). The solution was stirred for 1.5 h at room temperature then the solution of amine was added and stirring was continued for 16 h. The solution was concentrated under vacuum then water was added to the residue and the mixture was extracted with ethyl acetate (3×25 ml). The combined extracts were washed with brine, dried over anhydrous sodium sulfate and filtered. Concentration of the filtrate under vacuum yielded 58 mg of structure (50) as a yellow foam. MS (ES+): m/z 680.6 (M+H$^+$).

Structure (50) was oxidized to provide the corresponding ketone of structure (51).

Example 17

Activities of Representative β-Sheet Mimetics as a Protease Inhibitor

This example illustrates the ability of further representative β-sheet mimetics of this invention to function as an inhibitor for thrombin, Factor VII, Factor X, Factor XI, tryptase, aPC, plasmin, tPA, urokinase thrombin thrombomodulin complex and trypsin. The β-sheet mimetics of the structures listed in Table 9 had the inhibition activities shown in Table 10.

The proteinase inhibitor assays were performed as described in Example 9. The assay for thrombin-thrombomodulin complex was conducted as for thrombin except that prior to the addition of inhibitor and substrate, thrombin was preincubated with 4 nM thrombomodulin for 20 minutes at room temperature.

TABLE 9

Structures, Synthetic Precursors, and Physical Data for Various Serine Protease Inhibitors

| Structure Number | B$^\delta$ | R$_4$ | R$_5$ | Precursor | M.S. (ES+) | HPLC* R.T. (min) |
|---|---|---|---|---|---|---|
| (47) | N | (CH$_2$)$_3$NHC(NH)NH$_2$ | thiazolyl | (46) | 513.5 (M + H$^+$) | 15.9 |
| (20b) | N | (CH$_2$)$_3$NHC(NH)NH$_2$ | benzothiazolyl | (17) | 563.5 (M + H$^+$) | 17.9 |
| (37) | N | (CH$_2$)$_3$NHC(NH)NH$_2$ | C(O)NHCH$_2$Ph | (36) | 563.6 (M + H$^+$) | 16.9 |

TABLE 9-continued

Structures, Synthetic Precursors, and Physical Data for Various Serine Protease Inhibitors

| Structure Number | B[b] | R_4 | R_5 | Precursor | M.S. (ES+) | HPLC* R.T. (min) |
|---|---|---|---|---|---|---|
| (39) | N | (CH_2)_3-NH-C(=NH)-NH_2 (guanidinopropyl) | -C(=O)-NH-CH_2CH_2-(4-Cl-C_6H_4) | (38) | 611.3 (M + H+) | 19.8 |
| (29a)[e] | CH | (CH_2)_3-NH-C(=NH)-NH_2 | benzothiazol-2-yl | (17) | 562.4 (M + H+) | 21.2 |
| (35) | N | (CH_2)_3-NH-C(=NH)-NH_2 | -C(=O)-NH-CH_2CH_2-C_6H_5 | (34) | 577.4 (M + H+) | 18.1 |
| (45) | N | (CH_2)_3-NH-C(=NH)-NH_2 | methyl imidazole-carboxylate | (44) | 554.2 (M + H+) | 15.7 |
| (51) | N | -CH_2-NH-C(=O)-NH-C(=NH)-NH_2 | benzothiazol-2-yl | (49) | 578.3 (M + H+) | 22.3 |

TABLE 9-continued

Structures, Synthetic Precursors, and Physical Data for
Various Serine Protease Inhibitors

| Structure Number | B[b] | R$_4$ | R$_5$ | Precursor | M.S. (ES+) | HPLC* R.T. (min) |
|---|---|---|---|---|---|---|
| (29b) | CH | (3-guanidinopropyl) | benzothiazol-2-yl | (17) | FAB 562.4 (M + H$^+$) | 21.5 |
| (41) | N | (3-guanidinopropyl) | —C(O)NH-CH$_2$CH$_2$-(4-methoxyphenyl) | (40) | 607.4 (M + H$^+$) | 18.2 |
| (13) | N | (3-guanidinopropyl) | —CH$_2$Cl | Arg(Mtr)—CH$_2$Cl | 477.9 (M + H$^+$) | 14.9 |

[b]the stereochemistry of the template for B = CH is (3R, 6R, 9S) except where noted (see footnote e).
[e]Template stereochemistry is (3S, 6R, 9S).
*HPLC was performed on a reverse phase C-18 column using a gradient of 0-90% acetonitrile/water, 0.1% TFA.

TABLE 10

Ki (M) Inhibition Activity of Various Compounds Against Serine Proteases

| Structure Number | Thrombin | Factor VII | Factor X | Factor XI | Urokinase | T.T.C.[a] | aPC[b] | Plasmin | tPA[c] | Trypsin | Tryptase |
|---|---|---|---|---|---|---|---|---|---|---|---|
| 35 | 7.10E−11 | 1.64E−08 | 3.45E−07[e] | | | | | | | 2.70E−11 | |
| 37 | 7.32E−11 | | | | | | | | | 7.73E−11 | |
| 29b | 8.50E−11 | 2.00E−07 | 1.93E−08 | 7.53E−08 | 3.35E−07 | 8.80E−11 | 1.25E−06 | 2.51E−07 | 9.29E−08 | 2.30E−10 | 9.00E−09 |
| 39 | 3.10E−10 | | | | | | | | | | |
| 41 | 4.50E−10 | | | | | | | | | | |
| 20b | 6.50E−10 | 2.70E−07 | 2.22E−07 | 2.70E−08 | 6.00E−07 | | 3.32E−06 | 4.15E−07 | 4.95E−07 | 6.20E−10 | 1.24E−08 |
| 47 | 2.40E−09 | 9.68E−08 | 1.50E−0.6[e] | | | | | | | 1.90E−09 | |
| 45 | 5.40E−09 | 2.96E−05 | 3.80E−05 | 1.24E−06 | | 6.90E−09 | 2.56E−05 | 2.38E−05 | 1.72E−05 | 5.24E−08 | 1.65E−06 |
| 51 | 7.25E−09 | 4.26E−06 | 5.70E−05 | 1.73E−06 | | | | | | 3.79E−08 | |
| 29a | 1.04E−08 | 1.77E−06 | 4.65E−06[e] | 3.91E−07 | | | | | | 5.40E−10 | |
| 13[d] | 1.20E−09 | 1.40E−07 | 3.86E−07[e] | | 9.27E−07 | | 5.28E−07 | 9.78E−07 | 6.32E−07 | 1.60E−07 | |

[a]Thrombin thrombomodulin complex,
[b]activated Protein C,
[c]tissue Plasminogen Activator,
[d]IC50,
[e]bovine plasma

Example 18

Figure 2:
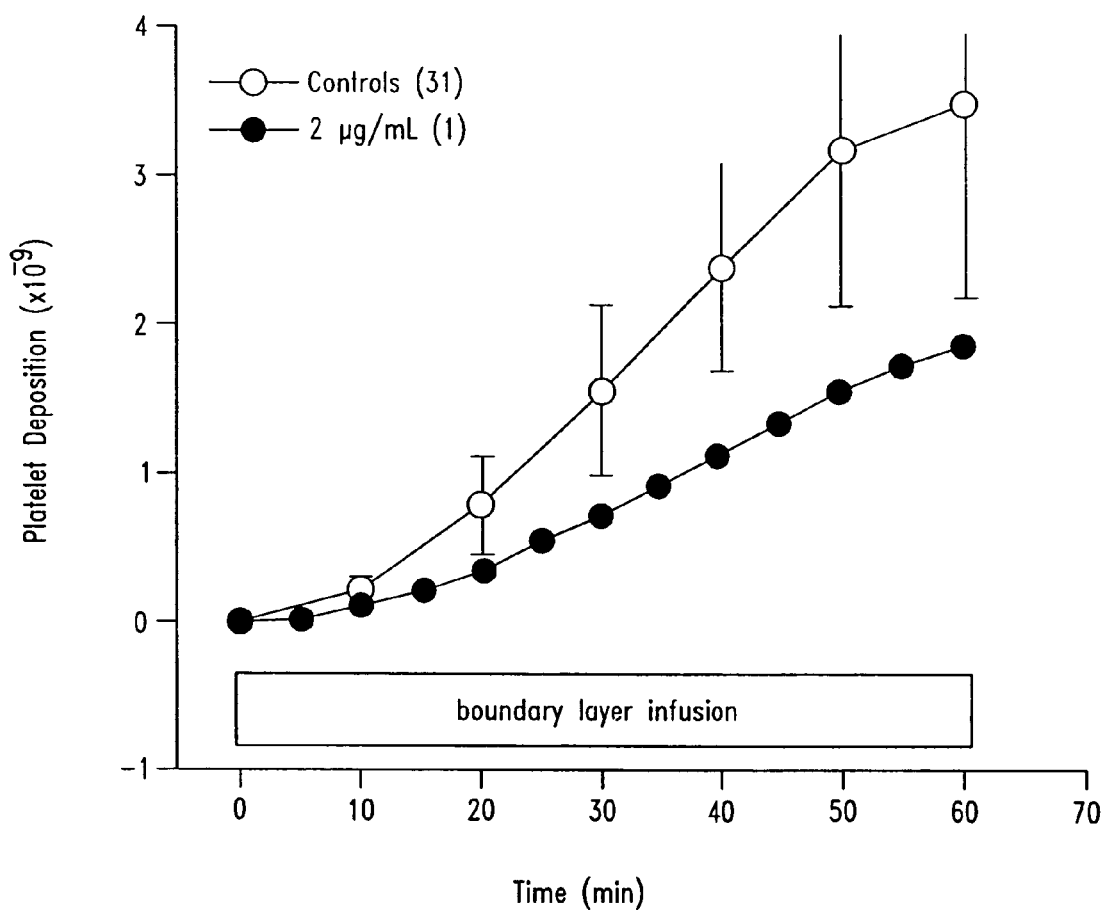
FIG. 2 is a plot showing the effect of various concentrations of structure (39) on platelet deposition in a vascular graft.
Figure 3:
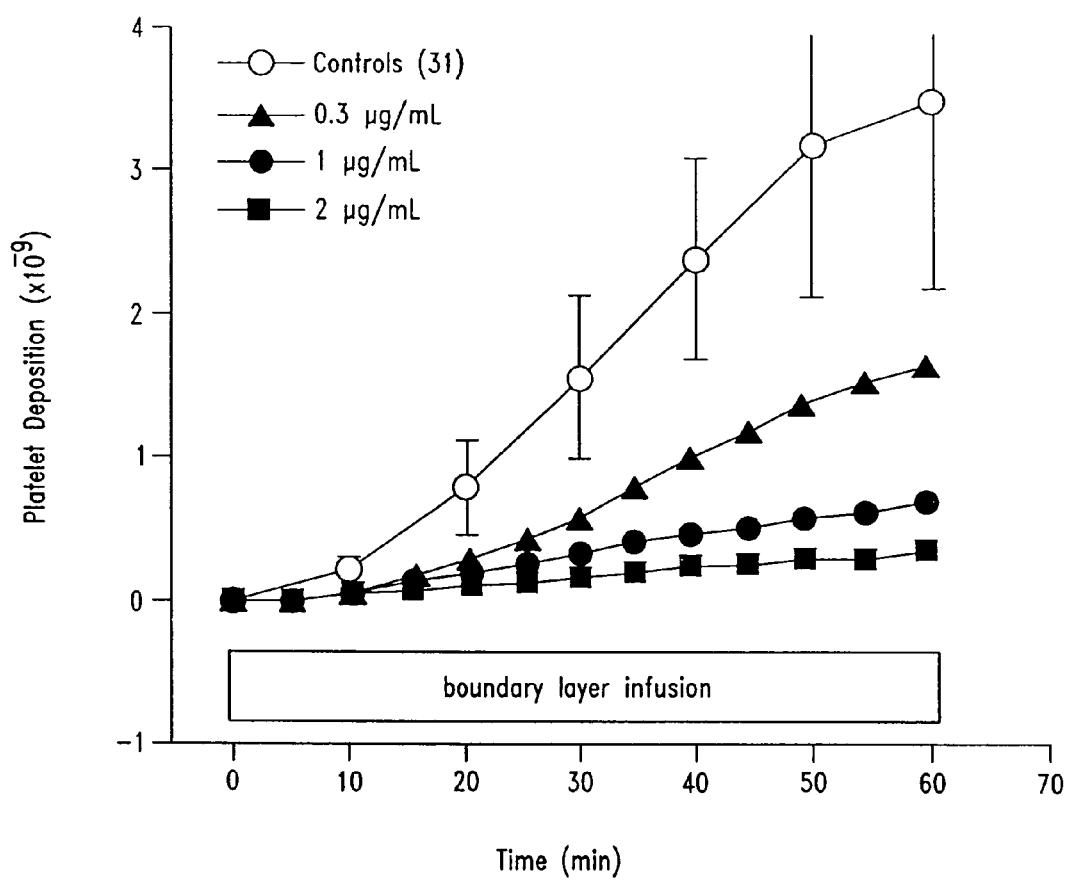
FIG. 3 is a plot showing the effect of various concentrations of structure (29b) on platelet deposition in a vascular graft.

Effect of Representative β-Sheet Mimetics on Platelet Deposition in a Vascular Graft The effect of compounds of the invention on platelet deposition in a vascular graft, was measured according to the procedure of Hanson et al. "Interruption of acute platelet-dependent thrombosis by synthetic antithrombin D-phenylalanyl-L-prolyl-L-arginyl chloromethylketone" *Proc. Natl. Acad. Sci., USA* 85:3148-3188, (1988), except that the compound was introduced proximal to the shunt as described in Kelly et al., *Proc. Natl. Acad. Sci., USA* 89:6040-6044 (1992). The results are shown in FIGS. 1, 2 and 3 for structures (20b), (39) and (29b), respectively.

Example 19

Synthesis of Representative β-Sheet Mimetics

This example illustrates the synthesis of a further representative β-sheet mimetic of this invention having the structure shown below.

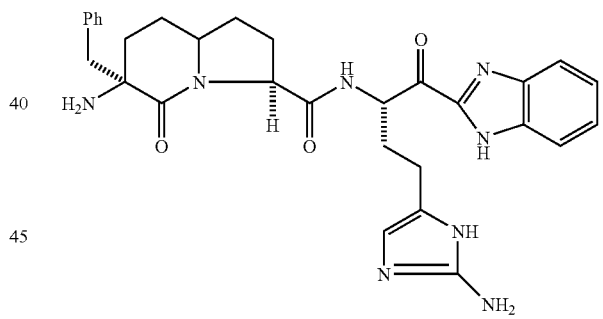

(52)

Structure (52) may be synthesized employing the following intermediate (53) in place of intermediate (16) in Example 2:

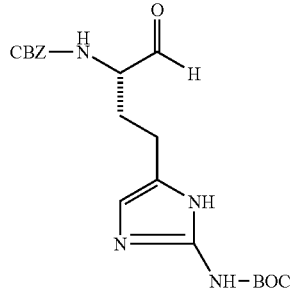

(53)

Intermediate (53) may be synthesized by the following reaction scheme:
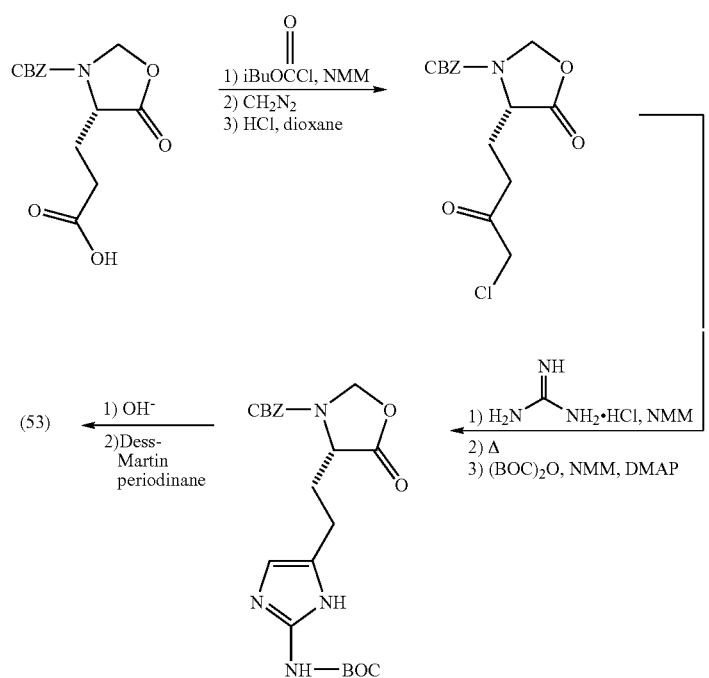
Alternatively, intermediate (53) may be synthesized by the following reaction scheme:
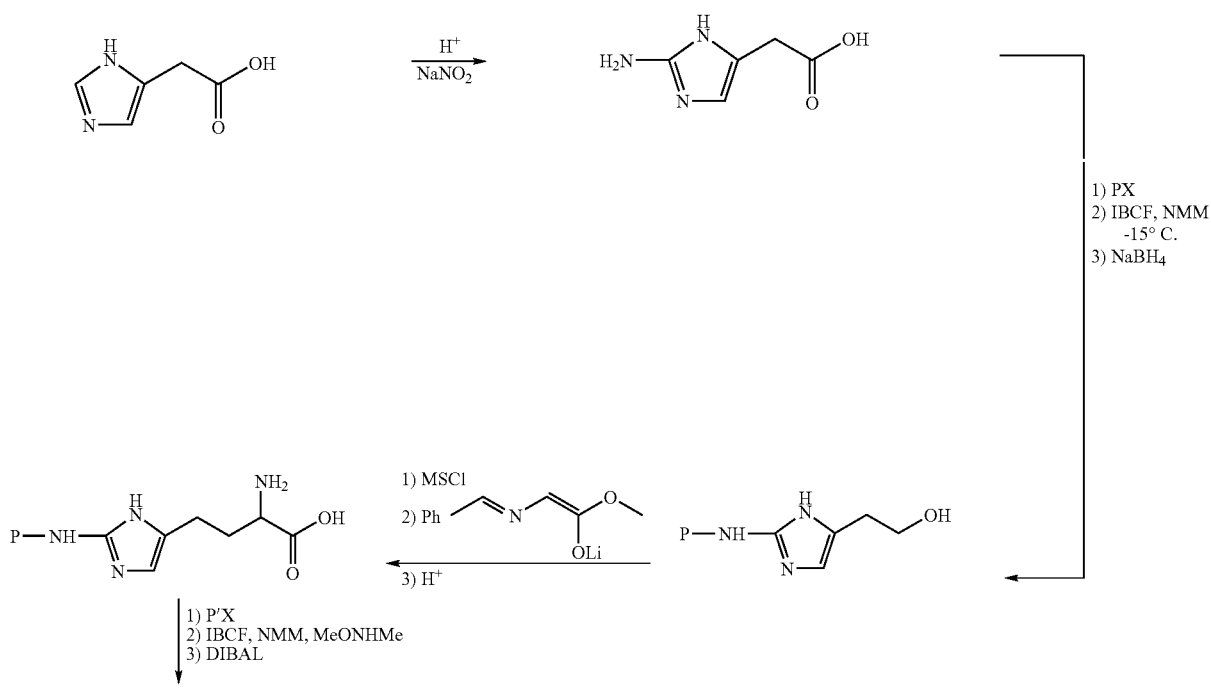

Example 20

Representative β-Sheet Mimetics Which Bind to MHC I and MHC II

The following structures (54), (55) and (56) were synthesized by the techniques disclosed herein.

The ability of structures (54) and (55) to bind to MHC I molecules can be demonstrated essentially as described by Elliot et al. (*Nature* 351:402-406, 1991). Similarly, the ability of structure (56) to bind to MHC II molecules can be demonstrated by the procedure of Kwok et al. (*J. Immunol.* 155: 2468-2476, 1995).

(54)

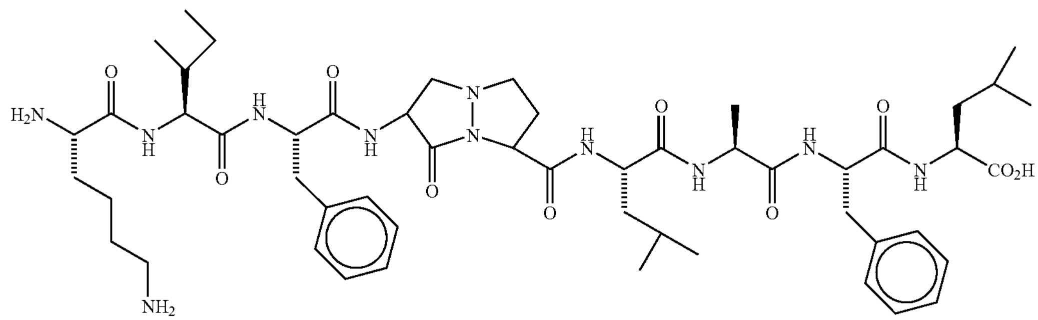

-

MS ES(+) 510 $(M+2H+)^{2+}$; HPLC $R_t$ 22.10° (0-90% acetonitrile/$H_2O$, 0.1% TFA)

(55)

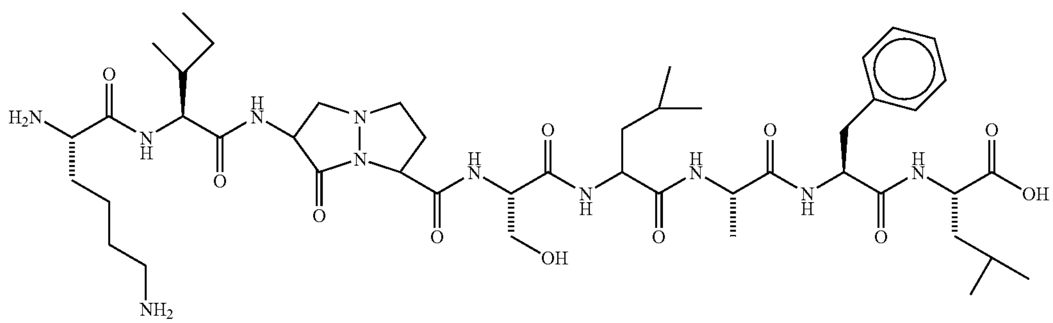

-

MS ES(+) 510 $(MH^+)^+$; HPLC $R_t$ 22.37° (0-90% acetonitrile/$H_2O$, 0.1% TFA)

(56)

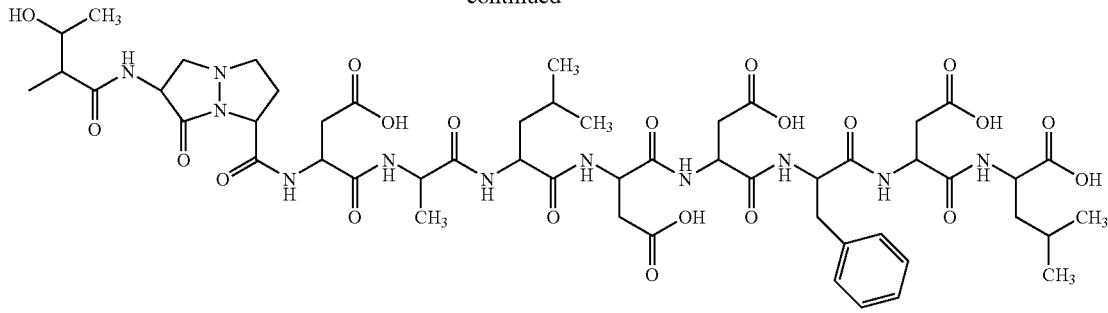

MS ES(−) 704.9 (M−3H⁺)³; HPLC R_t 22.39° (0-90% acetonitrile/H₂O, 0.1% TFA)

Example 21

Representative β-Sheet Mimetics Which Bind the SH2 Domain

The following structure (57) was synthesized, and structure (58) may be synthesized, by the techniques disclosed herein.

SH-PTP1

(57)

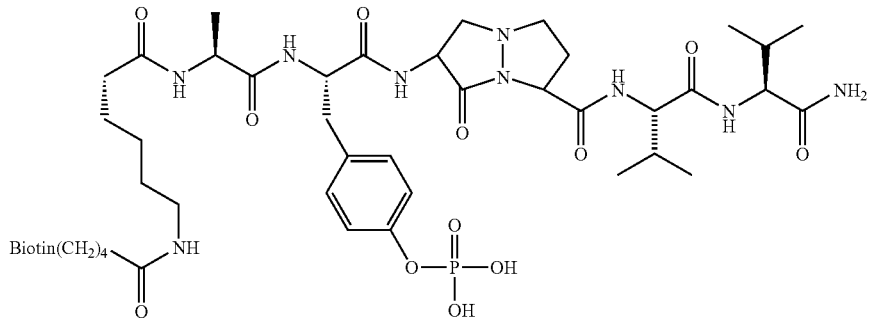

MS ES(−) 104.3 (M−H⁺)⁻; HPLC R_t 17.28° (0-90% acetonitrile/H₂O, 0.1% TFA)

STAT6

(58)

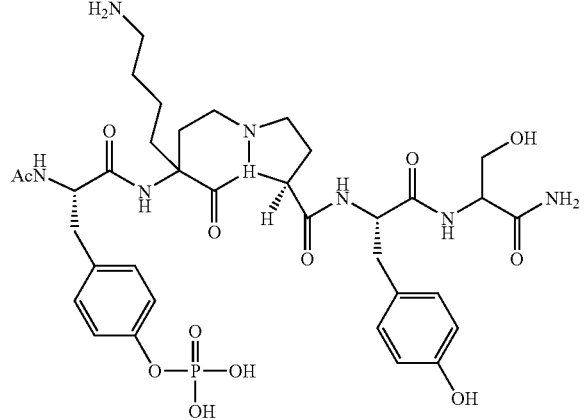

The ability of structure (58) to bind to the SH2 domain of STAT6, or of structure (57) to bind the SH2 domain of the protein tyrosine phosphatase SH-PTP1 can be demonstrated by the procedures disclosed by Payne et al. (*PNAS* 90:4902-4906, 1993). Libraries of SH2 binding mimetics may be screened by the procedure of Songyang et al. (*Cell* 72:767-778, 1993).

Example 22

Representative β-Sheet Mimetics Which Bind Protein Kinases

The following structure (59) may be synthesized by the techniques disclosed herein.

(59)

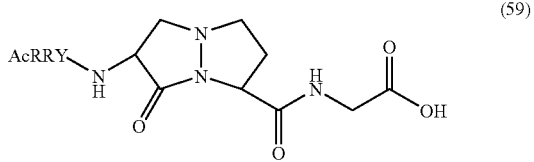

The ability of structure (59) to act as a substrate or inhibitor of protein kinases may be demonstrated by the procedure of Songyang et al. (*Current Biology* 4:973-982, 1994).

Example 23

Synthesis of Representative β-Sheet Mimetics

This example illustrates the synthesis of representative β-sheet mimetics of this invention having the following structures (60) through (63), wherein B is N or CH:

(60)

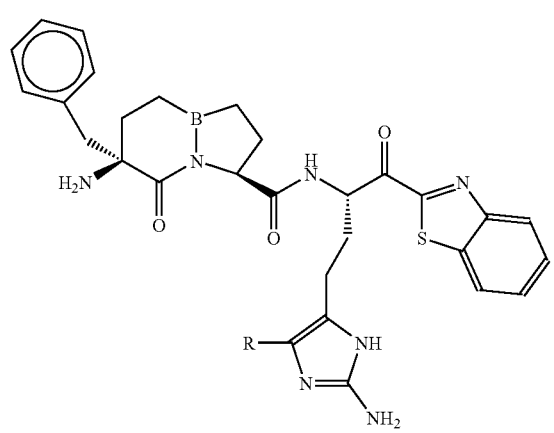

(61)

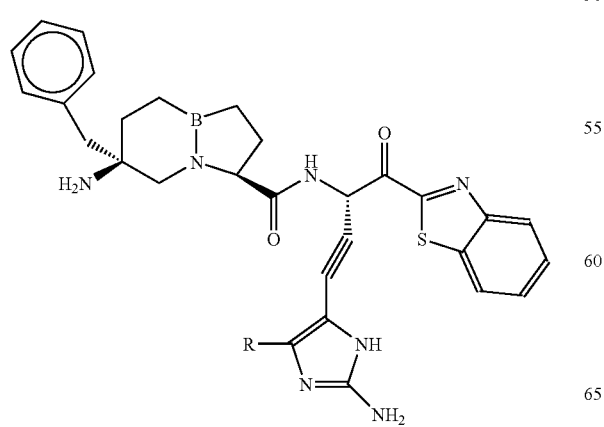

(62)

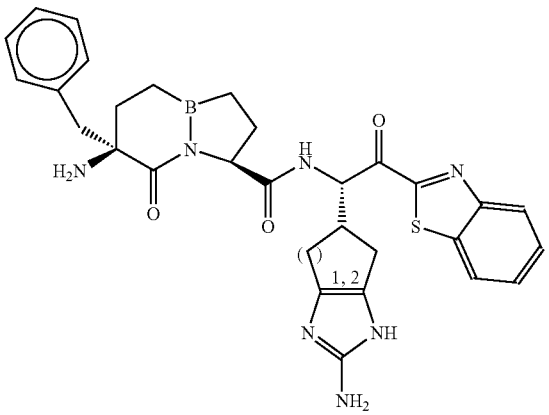

(63)

Synthesis of Structure (60)

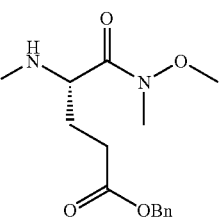

1. H₂, Pd-C MeOH
2. a) IBCF, NMM b) RCHN₂
3. HBr

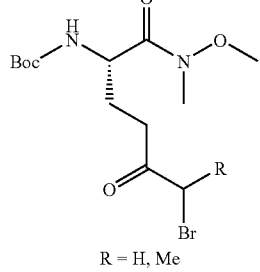

R = H, Me

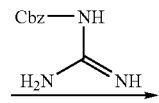

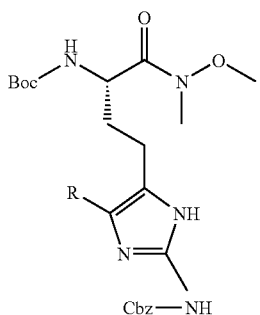

1. <image structure>
2. Cbz-Cl, NaHCO₃

117
-continued
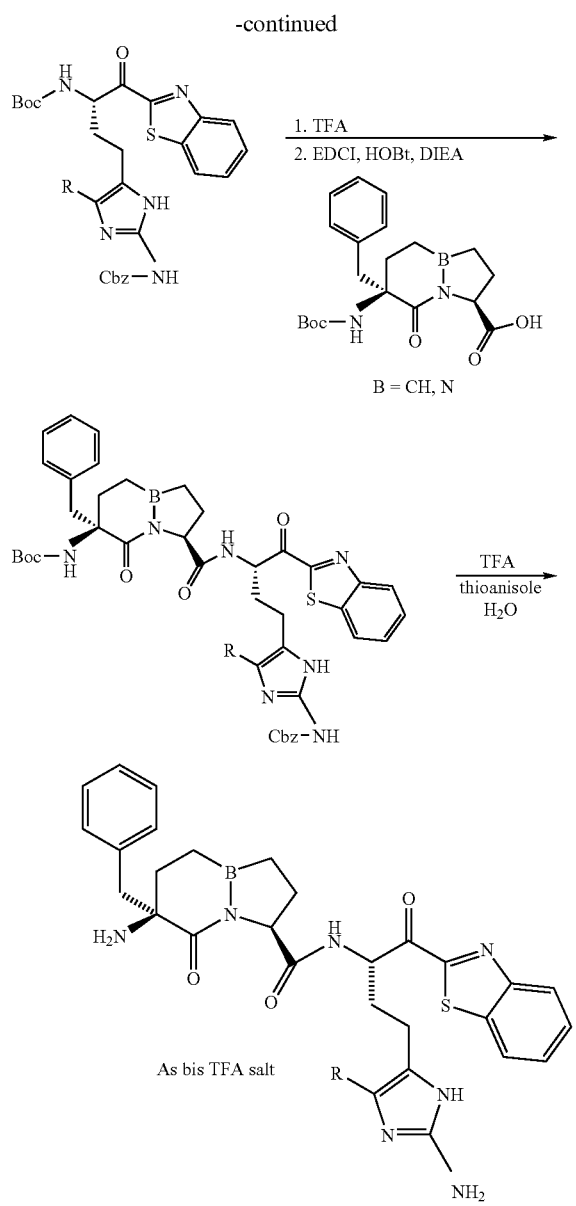
Synthesis of Structure (61)
118
-continued
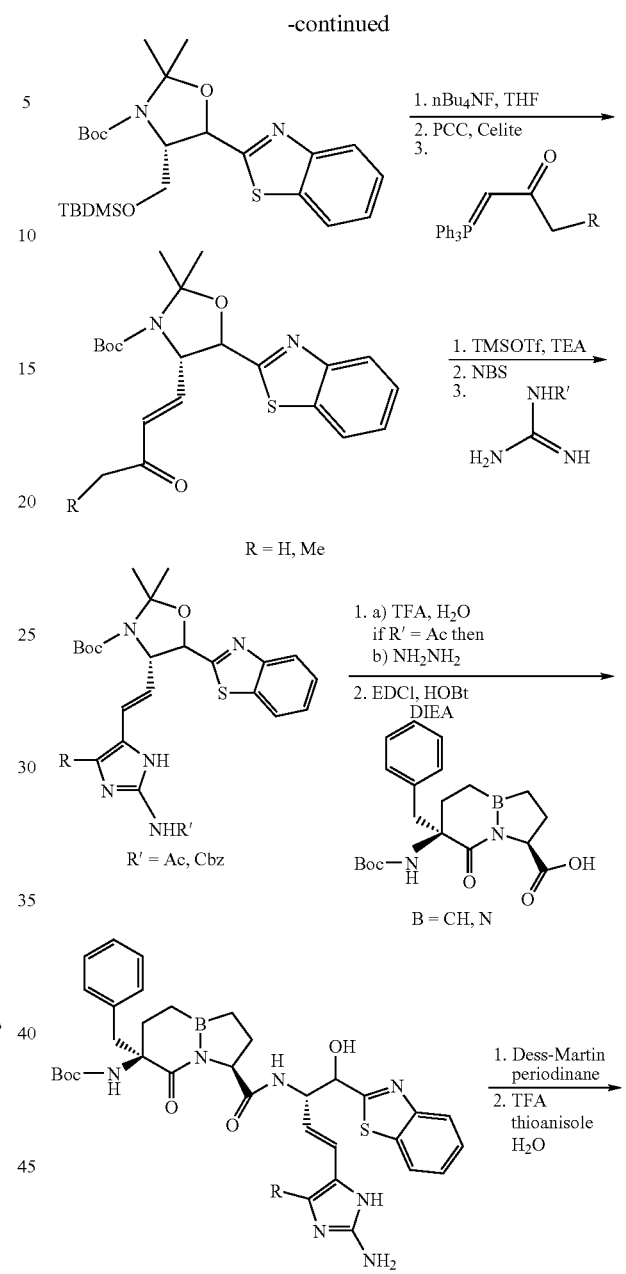
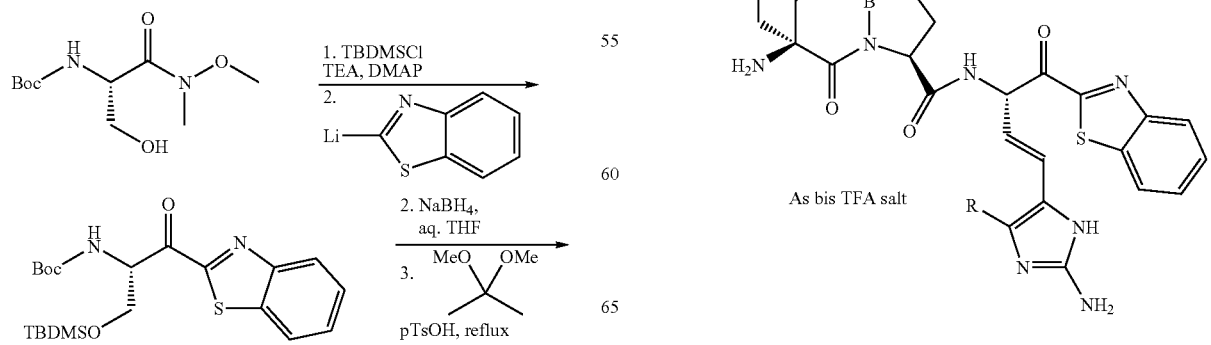

119
Alternative Synthesis of Structure (61)
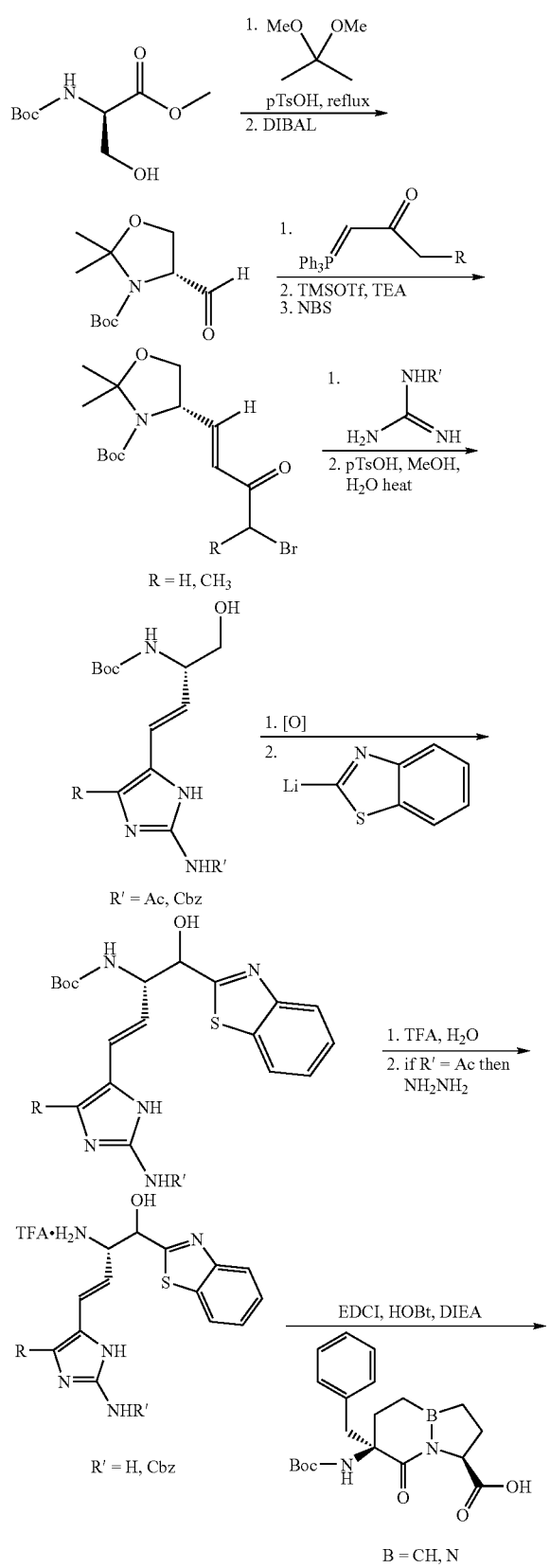
120
-continued
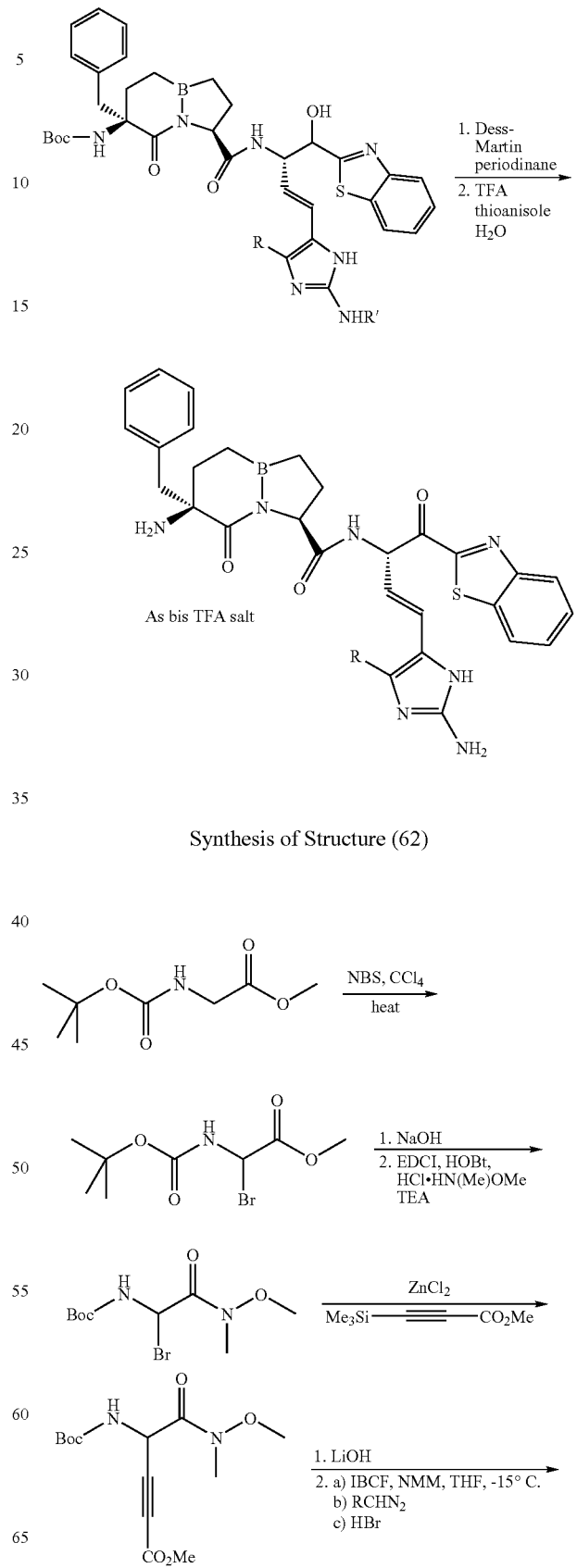
Synthesis of Structure (62)

-continued
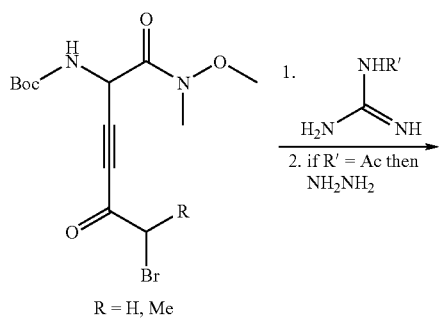
R = H, Me
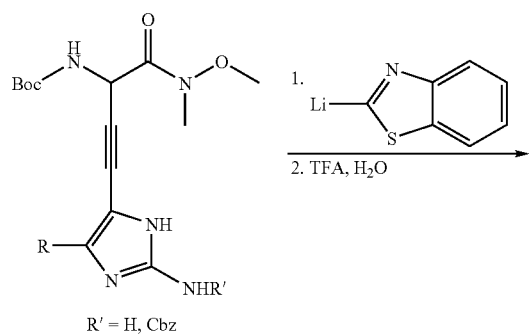
R' = H, Cbz
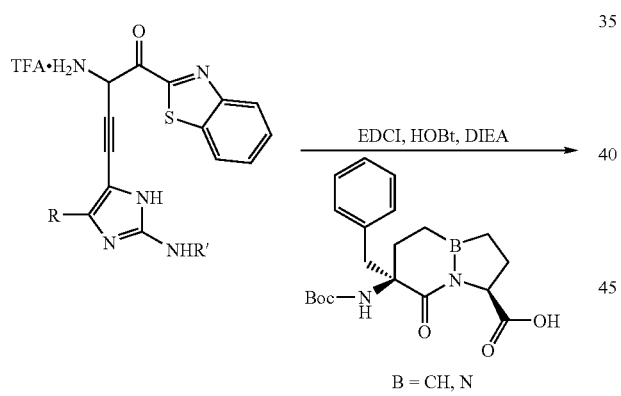
B = CH, N
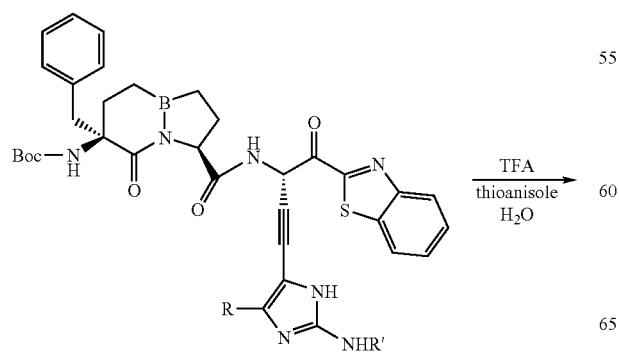
-continued
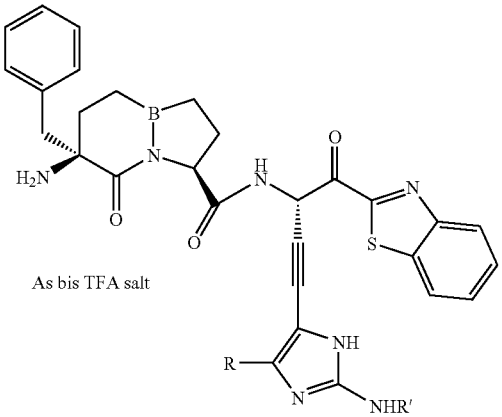
As bis TFA salt
Alternative Synthesis of Structure (62)
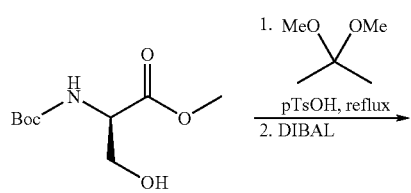
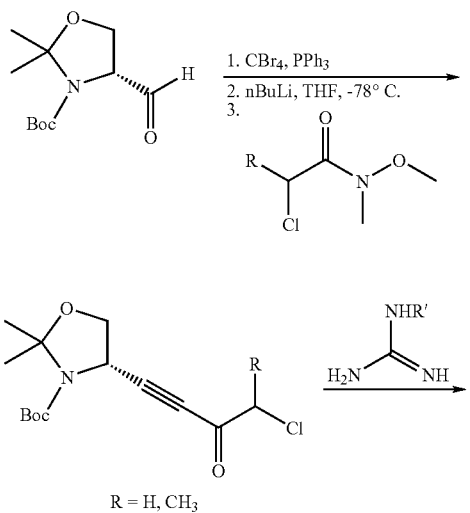
R = H, CH₃
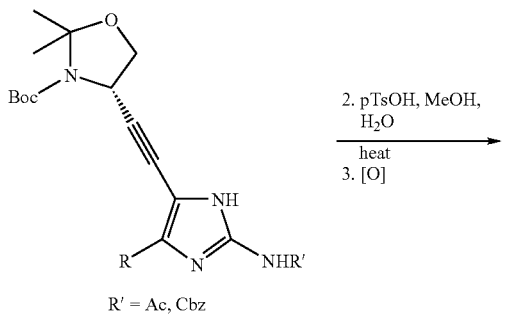
R' = Ac, Cbz

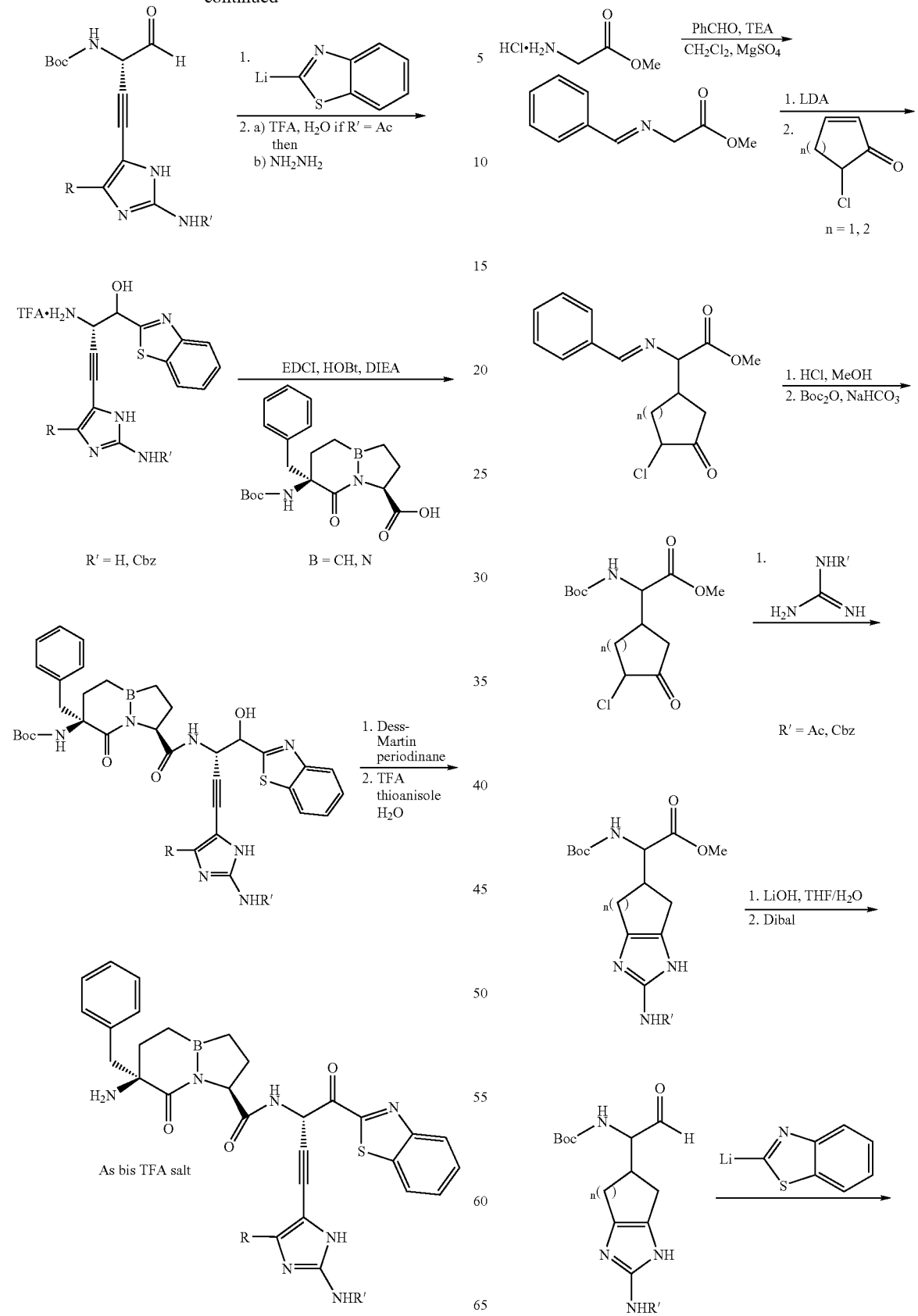

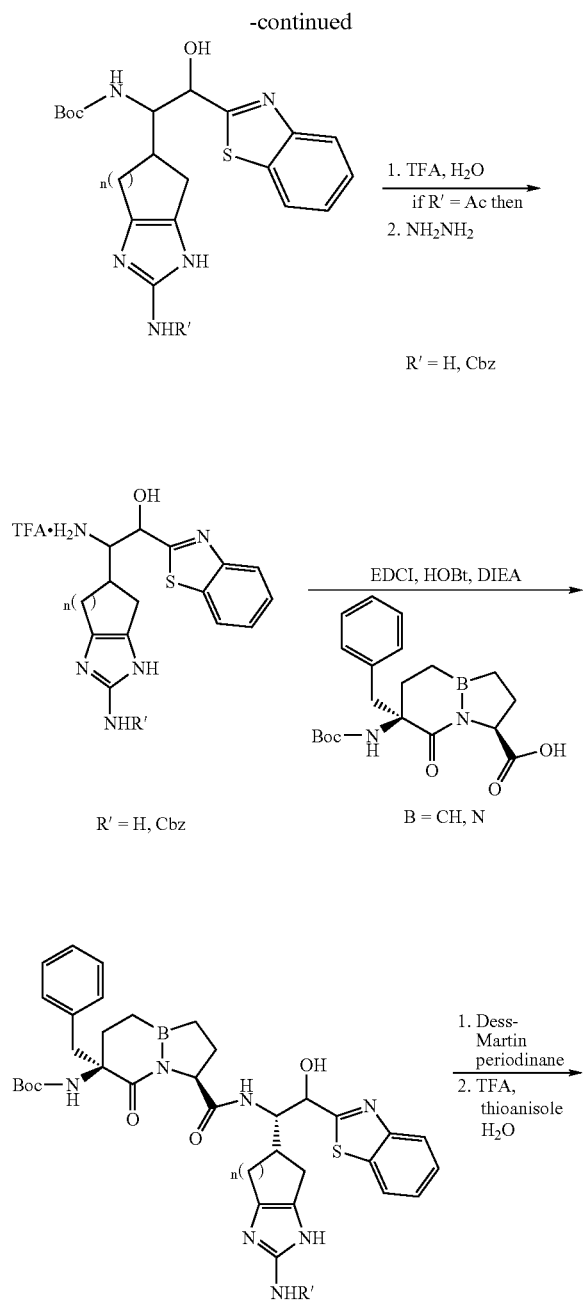

Example 24

Bioavailability of Representative β-Sheet Mimetics

This example illustrates the bioavailability of the compound of structure (20b) as synthesized in Example 2 above, and having the biological activity reported in Example 9 above.

Figure 4A:
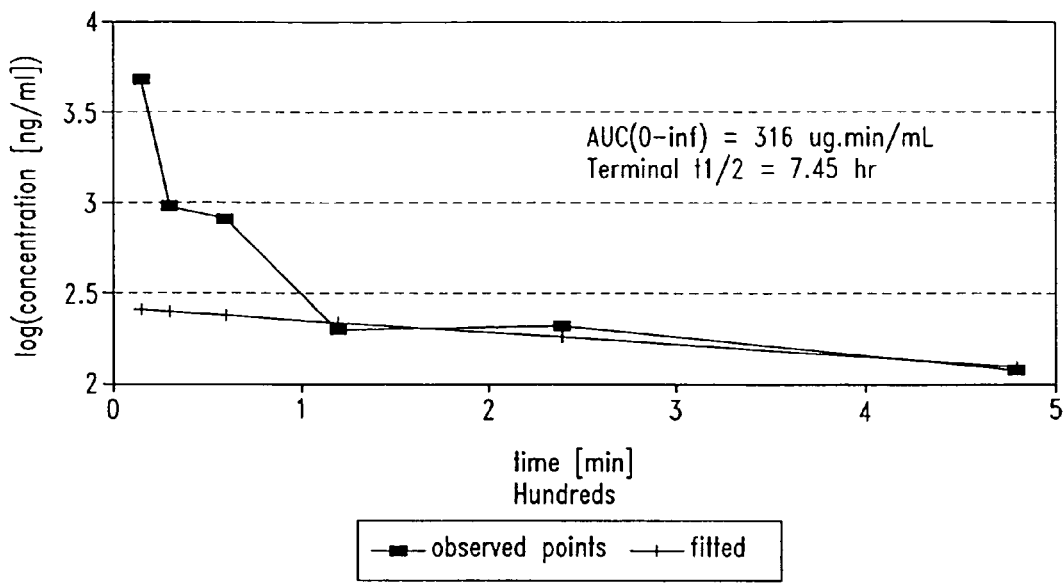
FIGS. 4A and 4B are plots showing the in vivo efficacy of structure (20b) for dosing of 4 mg/kg IV and 10 mg/kg PO, respectively.
Figure 4B:
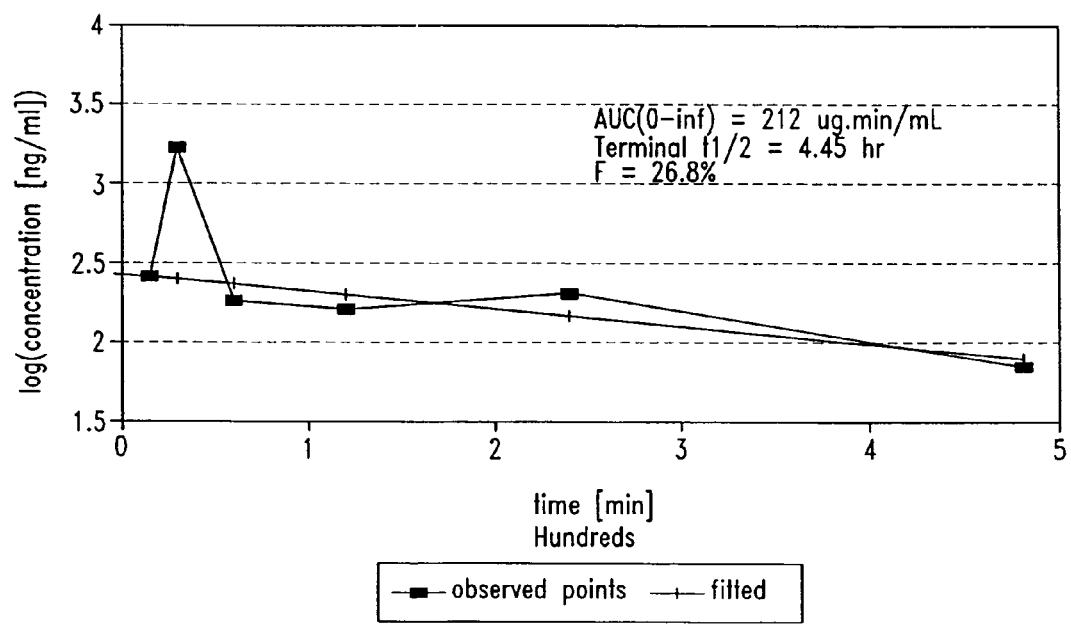

Specifically, a pharmacodynamic and pharmacokinetic study of structure (20b) was conducted in male Sprague Dawley rats. Rats were administered a saline solution of structure (20b) at 4 mg/kg intravenously (IV) or 10 mg/kg orally (PO). Groups of rats (n=3 or 4) were sacrificed and exsanguinated at 0.25, 0.5, 1, 2, 4 and 8 hours following dosing. Efficacy parameters, aPTT and TT, were measured for each plasma sample. Concentrations of structure (20b) in plasma were determined by a trypsin inhibition assay. The results of this experiment are presented in FIGS. 4A and 4B for dosing of 4 mg/kg IV and 10 mg/kg PO, respectively. The data presented in FIGS. 4A and 4B illustrate in vivo efficacy of structure (20b) via both IV and PO administration. Non-compartmental pharmacokinetic analysis of mean structure (20b) concentration values demonstrate terminal halflives of 7.5 hr (IV) and 4.5 hr (PO). The bioavailability of orally administered structure (20b) is approximately 27%.

From the foregoing, it will be appreciated that, although specific embodiments of this invention have been described herein for purposes of illustration, various modifications may be made without deviating from the spirit and scope of the invention. Accordingly, the invention is not limited except by the appended claims.

---

What is claimed is:

1. A compound having either a first structure:

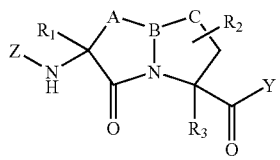

or a pharmaceutically acceptable salt thereof, wherein $R_1$, $R_2$ and $R_3$ are independently selected from amino acid side chain moieties and derivatives thereof; A is selected from —$(CH_2)_{1-2}$O— and —$(CH_2)_{1-2}$S—; B is N; C is selected from —C(=O)—, —$(CH_2)_{1-3}$—, —O—, —S—, —O—$(CH_2)_{1-2}$— and —S$(CH_2)_{1-2}$; Y and Z represent the remainder of the molecule; and any two adjacent CH groups of the bicyclic ring may form a double bond, or a second structure:

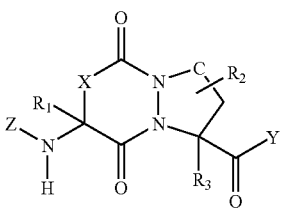

or a pharmaceutically acceptable salt thereof, wherein X has the structure —$(CH_2)_n$—, where "n" is an integer of 0-3, wherein any two adjacent CH groups of the bicyclic ring may form a double bond, wherein $R_1$, $R_2$, $R_3$, C, Y, and Z are as defined above, except with the proviso that when X has the structure —$(CH_2)_{0-2}$—, C has the structure —$(CH_2)_{1-2}$—, and $R_2$ is H, then $R_1$ is not H.

2. The compound of claim 1 wherein the bicyclic ring of either the first structure or the second structure is saturated.

3. The compound of claim 2 having the structure

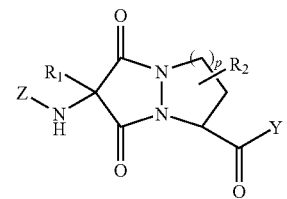

wherein p is an integer from 1 to 3.

4. The compound of claim 3 having the structure

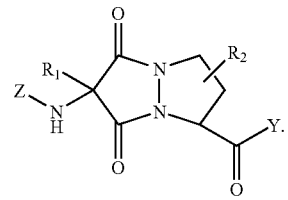

5. The compound of claim 3 having the structure

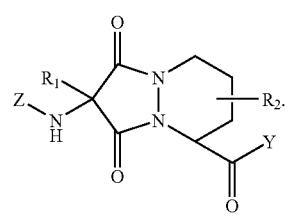

6. The compound of claim 1 wherein $R_1$ is selected from a lower chain alkyl moiety, a lower chain aryl moiety and a lower chain aralkyl moiety.

7. The compound of claim 6 wherein $R_1$ is a lower chain aralkyl moiety.

8. The compound of claim 7 wherein the lower chain aralkyl moiety is selected from —$CH_2$phenyl and —CH(phenyl)$_2$.

9. The compound of claim 1 wherein Y and Z are independently chosen from amino acids, β-sheet mimetics, suitable terminating moieties, amino acid side chain moieties, and amino acid side chain derivatives.

10. The compound of claim 1 wherein $R_1$, Y, and Z are independently chosen from straight chain or branched, cyclic or noncyclic, substituted or unsubstituted, saturated or unsaturated lower chain alkyl, aryl or aralkyl moieties.

11. The compound of claim 1 wherein $R_1$, Y, and Z are independently chosen from:
   (i) the side chain moieties of 3,5-dibromotyrosine, 3,5-diiodotyrosine, hydroxylysine, naphthylalanine, thienylalanine, γ-carboxyglutamate, phosphotyrosine, phosphoserine; and
   (ii) —H, —$CH_3$, —$CH(CH_3)_2$, —$CH_2CH(CH_3)_2$, —$CH(CH_3)CH_2CH_3$, —$(CH_2)_3NHC(NH_2)NH_2^+$,

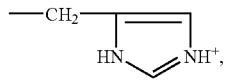

—$CH_2COO-$, —$CH_2CH_2COO-$, —$CH_2CONH_2$, —$CH_2CH_2CONH_2$,

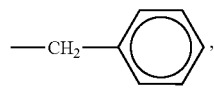

—$CH_2SH$, —$CH_2CH_2SCH_3$, —$CH_2OH$, —$CH(OH)CH_3$.

12. The compound of claim 1 wherein Y is chosen from —H, —OH, —R, —NHOH, —NHNHR, —C(=O)OR, —C(=O)NHR, —$CH_2Cl$, —$CF_3$, —$C_2F_5$, —$CHN_2$,

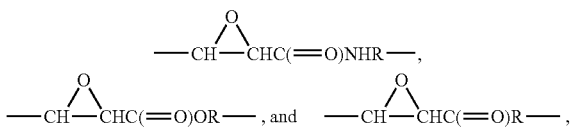

wherein R is a $C_1$-$C_8$ alkyl moiety, aryl moiety, or a heterocyclic moiety.

13. The compound of claim 1 wherein Y groups have the structure:

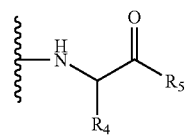

wherein
$R_4$ groups are organoamine moieties having from about 2 to about 10 carbon atoms and at least one nitrogen atom; and
$R_5$ is selected from (a) alkyl of 1 to about 12 carbon atoms, optionally substituted with 1-4 of halide, $C_{1-5}$alkoxy and nitro, (b) —C(=O)NH—$C_{1-5}$alkyl, wherein the alkyl group is optionally substituted with halide or $C_{1-5}$alkoxy, (c) —C(=O)NH—$C_{1-10}$aralkyl where the aryl group may be optionally substituted with up to five groups independently selected from nitro, halide, —NH—(C=O)$C_{1-5}$alkyl, —NH—(C=O)$C_{6-10}$aryl, $C_{1-5}$alkyl and $C_{1-5}$alkoxy, and (d) monocyclic and bicyclic heteroaryl of 4 to about 11 ring atoms, where the ring atoms are selected from carbon and the heteroatoms oxygen, nitrogen and sulfur, and where the heteroaryl ring may be optionally substituted with up to about 4 of halide, $C_{1-5}$alkyl, $C_{1-5}$alkoxy, —C(=O)NH$C_{1-5}$alkyl, —C(=O)NH$C_{6-10}$aryl, amino, —C(=O)O$C_{1-5}$alkyl and —C(=O)O$C_{6-10}$aryl.

14. The compound of claim 13 wherein $R_4$ is:

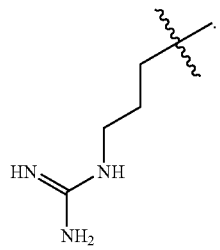

15. The compound of claim 13 wherein $R_4$ is selected from:

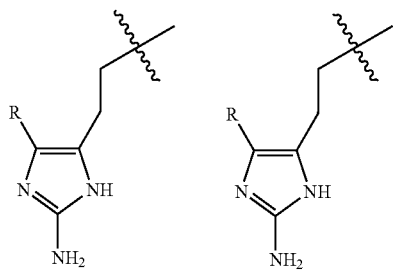

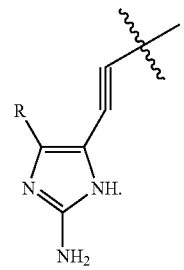

wherein R is selected from hydrogen, methyl, halogen and hydroxymethyl.

16. The compound of claim 13 wherein $R_4$ is:

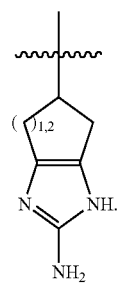

17. The compound of claim 13, wherein $R_5$ is chosen from:

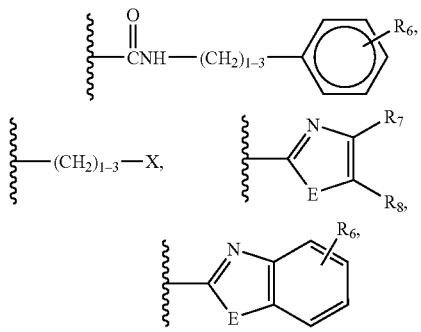

wherein $R_6$ is chosen from hydrogen, nitro, halide, NH—C(=O)—$C_{1-5}$alkyl,
NH—C(=O)—$C_{6-10}$aryl, $C_1C_5$alkyl and $C_1$-$C_5$ alkoxy;
X is halide; and
E is —O—, —NH— or —S— and $R_7$ and $R_8$ are independently selected from hydrogen, $C_{1-5}$alkyl, —C(=O)OC$_{1-5}$alkyl, —C(=O)OC$_{6-10}$aryl, —C(=O)NHC$_{1-5}$alkyl and —C(=O)NHC$_{6-10}$aryl.

18. The compound of claim 13 wherein $R_5$ is a heterocyclic moiety selected from pyridine, pyran, pyrrole, furan, thiophene, thiazole, benzothiazole, oxazole, benzoxazole, imidazole and benzimidazole.

19. The compound of claim 18 wherein the heterocyclic moiety is benzothiazole.

20. The compound of claim 13 wherein Z is chosen from —H, —OH, —R, —C(=O)R and —SO$_2$R, wherein R is a $C_1$-$C_8$ alkyl moiety or an aryl moiety.

21. The compound of claim 20 wherein Z is selected from —H and —SO$_2$phenyl.

22. A composition comprising a compound of claim 1 and a pharmaceutically acceptable carrier.

23. A method for inhibiting a serine protease in a warm-blooded animal, comprising administering to the animal an effective amount of the compound of claim 1.

24. The compound of claim 1 wherein A is —(CH$_2$)$_{1-2}$O— or —(CH$_2$)$_{1-2}$S—.

25. The compound of claim 1 wherein C is C(=O)—, —O—, or —S—.

26. The compound of claim 1 wherein C is —O—(CH$_2$)$_{1-2}$— or —S(CH$_2$)$_{1-2}$—.

27. The compound of claim 1 having stereochemistry chosen from:

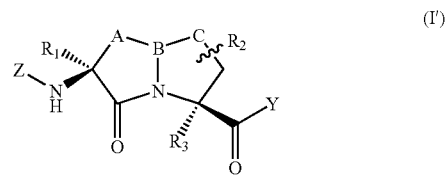

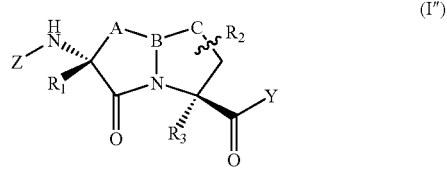

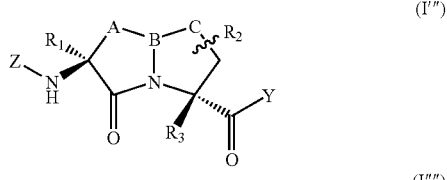

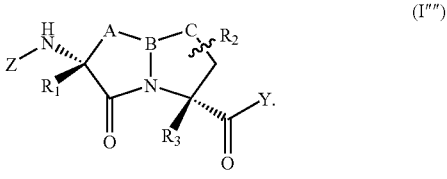

28. The compound of claim 1, wherein when the compound has the second structure and when C has the structure —(CH$_2$)$_{1-2}$— and $R_2$ is H, then $R_1$ is not H.

* * * * *